(12) United States Patent
Bhatia et al.

(10) Patent No.: US 9,347,102 B2
(45) Date of Patent: May 24, 2016

(54) GENE SIGNATURES FOR PREDICTION OF THERAPY-RELATED MYELODYSPLASIA AND METHODS FOR IDENTIFICATION OF PATIENTS AT RISK FOR DEVELOPMENT OF THE SAME

(71) Applicants: CITY OF HOPE, Duarte, CA (US); FRED HUTCHINSON CANCER RESEARCH CENTER, Seattle, WA (US)

(72) Inventors: Ravi Bhatia, Arcadia, CA (US); Smita Bhatia, Arcadia, CA (US); Stephen Forman, Duarte, CA (US); Jerald P. Radich, Seattle, WA (US); Liang Li, Duarte, CA (US); Min Li, Duarte, CA (US); Lue Ping Zhao, Seattle, WA (US)

(73) Assignees: CITY OF HOPE, Duarte, CA (US); FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 13/913,077

(22) Filed: Jun. 7, 2013

(65) Prior Publication Data
US 2013/0274138 A1 Oct. 17, 2013

Related U.S. Application Data

(63) Continuation of application No. PCT/US2011/064040, filed on Dec. 8, 2011.

(60) Provisional application No. 61/421,200, filed on Dec. 8, 2010.

(51) Int. Cl.
*C07H 21/04* (2006.01)
*C12Q 1/68* (2006.01)
*C07H 21/02* (2006.01)

(52) U.S. Cl.
CPC ............ *C12Q 1/6886* (2013.01); *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2004/0018513 A1* | 1/2004 | Downing et al. | 435/6 |
| 2007/0099209 A1* | 5/2007 | Clarke et al. | 435/6 |
| 2007/0198198 A1 | 8/2007 | Burczynski et al. | |
| 2008/0305965 A1* | 12/2008 | Moorhouse et al. | 506/16 |

OTHER PUBLICATIONS

Li et al., "Altered Expression in CD34+ Cells from PBSC Grafts from Patients Developing t-MDS Following Autologous Transplatation for Lymphoma" 108 Blood Abstract 2326 (Nov. 2006).*
Li et al., "Gene Expression Changes in CD34+ Cells Precede Development of Therapy-Related Leukemia (t-MDS/AML) After Autologous Hematopoietic Cell Transplantation (aHCT) for Hodgkin (HL) or Non-Hodgkin Lymphoma (NHL)" 114 Blood Abstract 677 (Nov. 2009).*
Li et al., Altered Hematopoietic Cell Gene Expression Identifies Patients at Risk for Development of Therapy-Related Leukemia (t-MDS/AML) (Nov. 2010).*
Ding et al., "Genetic Susceptibility to Therapy-Related Leukemia (t-MDS/AML) After Hodgkin Lymphoma (HL) or Non-Hodgkin Lymphoma (NHL)" 114 Blood Abstract 199 (Nov. 2009).*
Yamashita et al., "Analysis of chromosome copy number in leukemic cells by different microarray platforms" 21 Leukemia 1333-1337 (2007).*
Ben-Yehuda, D., et al., "Microsatellite Instability and p. 53 Mutations in Therapy-Related Leukemia Suggest Mutator Phenotype," Blood 88:4296-4303 (1996).
Bhatia, R., et al., "Longitudinal Assessment of Hematopoietic Abnormalities After Autologous Hematopoietic Cell Transplantation for Lymphoma," J. Clin. Oncol. 23:6699-6711 (2005).
Bhatia, S., et al., "Malignant Neoplams Following Bone Marrow Transplantation," Blood 87:3633-3639 (1996).
Bullinger, L., et al., "Gene-Expression Profiling Identifies Distinct Subclasses of Core Binding Factor Acute Myeloid Leukemia," Blood 110:1291-1300 (2007).
Chakraborty, S., et al., "Accelerated Telomere Shortening Precedes Development of Therapy-Related Myelodysplasia or Acute Myelogenous Leukemia After Autologous Transplantation for Lymphoma," J. Clin. Oncol. 27:791-798 (2009).
Chen, H.Z., et al., "Emerging Roles of E2Fs in Cancer: An Exit from Cell Cycle Control," Nat. Rev. Cancer 9 (11):785-797 (2009).
Cheung, A. M. S., et al., "A Comparitive Study of Bone Marrow and Peripheral Blood CD34+ Myeloblasts in Acute Myeloid Leukaemia," Br. J. Haematol. 144:484-491 (2008).
Colburn, N. H., et al., "Targeting Transcription Factors for Cancer Prevention—The Case of Nrf2," Cancer Prev. Res.1:153-155 (2008).
Ebert, B. L., et al., "Identification of RPS14 as a 5q-Syndrome Gene by RNA Interference Screen," Nature 451 (7176):335-339 (2008).
Feldser, D. M., et al., "Short Telomeres Limit Tumor Progression in Vivo by Inducing Senescence," Cancer cell 11 (5):461-469 (2007).
Fumagalli, S., et al., "Absence of Nucleolar Disruption After Impairment of 40S Ribosome Biogenesis Reveals an rpL11-Translation-Dependent Mechanism of p. 53 Induction," Nat. Cell Biol. 11(4):501-508 (2009).

(Continued)

*Primary Examiner* — Nancy J Leith
(74) *Attorney, Agent, or Firm* — Perkins Coie LLP; Lara Dueppen

(57) ABSTRACT

In one embodiment, a gene expression signature for predicting risk of developing therapy-related myelodysplasia or acute myeloid leukemia (t-MDS/AML) after autologous hematopoietic cell transplantation (aHCT) is provided. In another embodiment, a method for predicting a risk for development of t-MDS/AML after aHCT is provided. Such a method may include providing a biological sample that contains CD34 cells from a subject; detecting a test expression level of a set of two or more genes of a gene expression signature; comparing the test expression level of a set of corresponding training expression levels that include a training case expression level and a training control expression level; and predicting a high risk of developing t-MDS/AML when the test expression level is at or about the training case expression level or predicting a low risk of developing t-MDS/AML when the test expression level is at or about the training control expression level.

1 Claim, 56 Drawing Sheets

(56) References Cited

OTHER PUBLICATIONS

Gupta, R., et al., "Myelodysplastic Syndrome with Isolated Deletion of Chromosome 20q: An Indolent Disease with Minimal Morphological Dysplasia and Frequent Thrombocytopenic Presentation," Br. J. Haematol. 139:265-268 (2007).

Han, J.Y., et al., "Karyotypic Identification of Abnormal Clones Preceding Morphological Changes or Occurring with No Definite Morphological Features of Myelodysplastic Syndrome: A Preliminary Study," Lab. Hematol. 13:17-21 (2007).

Harper, J. W., et al., "The DNA Damage Response: Ten Years After," Mol. Cell 28:739-745 (2007).

Hock, H., et al., "Zinc-Finger Transcription Factor Gfi-1: Versatile Regulator of Lymphocytes, Neutrophils and Hematopoietic Stem Cells," Curr. Opin. Hematol. 13:1-6 (2006).

Ito, K., et al., "Regulation of Oxidative Stress by ATM is Required for Self-Renewal of Haematopoietic Stem Cells," Nature 431:997-1002 (2004).

Kalaycio, M., et al., "Risk Factors Before Autologous Stem-Cell Transplantation for Lymphoma Predict for Secondary Myelodysplasia and Acute Myelogenous Leukemia," J. Clin. Oncol. 24:3604-3610 (2006).

Kastan, M. B., et al., "Cell-Cycle Checkpoints and Cancer," Nature 432:316-323 (2004).

Kowaltowski, A. J., et al., "Mitochondria and Reactive Oxygen Species," Free Radical Biol. Med. 47:333-343 (2009).

Krishnan, A., et al, "Predictors of Therapy-Related Leukemia and Myelodysplasia Following Autologous Transplantation for Lymphoma: An Assessment of Risk Factors," Blood 95:1588-1593 (2000).

Lenka, N., et al., "Structural Organization and Transcription Regulation of Nuclear Genes Encoding the Mammalian Cytochrome c Oxidase Complex," Prog. Nucleic Acids Res. Mol. Biol. 61:309-344 (1998).

Li, L. et al "Altered Hematopoietic Cell Gene Expression Precedes Development of Therapy-Related Myelodysplasia/Acute Myeloid Leukemia and Identifies Patients at Risk," Cancer Cell 20:591-605 (2011).

Liu, J. M., et al., "Ribosomes and Marrow Failure: Coincidental Association or Molecular Paradigm?" Blood 107:4583-4588 (2006).

Miller, J. S., et al., "Myelodysplastic Syndrome After Autologous Bone Marrow Transplantation: An Additional Late Complication of Curative Cancer Therapy," Blood 83(12):3780-3786 (1994).

Nguyen, T., et al., "The Nrf2-Antioxidant Response Element Signaling Pathway and Its Activation by Oxidative Stress," J. Biol. Chem. 284:13291-13295 (2009).

Pedersen-Bjergaard, J., et al., "Therapy-Related Acute Myeloid Leukemia and Myelodysplasia After High-Dose Chemotherapy and Autologous Stem Cell Transplantation," Blood 95:3273-3279 (2000).

Pedersen-Bjergaard, J., "Insights into Leukemogenesis from Therapy-Related Leukemia," N. Engl. J. Med. 352 (15):1591-1594 (2005).

Qian, Z., et al., "Expression Profiling of CD34+ Hematopoietic Stem/Progenitor Cells Reveals Distinct Subtypes of Therapy-Related Acute Myeloid Leukemia," PNAS 99(23):14925-14930 (2002).

Rassool, F. V., et al., "Reactive Oxygen Species, DNA Damage, and Error-Prone Repair: A Model for Genomic Instability with Progression in Myeloid Leukemia?," Cancer Res. 67:8762-8771 (2007).

Shimizu, R., et al., "GATA1-Related Leukaemias," Nat. Rev. Cancer 8:279-287 (2008).

Smith, S. M., et al., "Clinical-Cytogenetic Associations in 306 Patients with Therapy-Related Myelodysplasia and Myeloid Leukemia: the University of Chicago Series," Blood 102:43-52 (2003).

Sole, F., et al., "Incidence, Characterization and Prognostic Significance of Chromosomal Abnormalities in 640 Patients with Primary Myelodysplastic Syndromes," Br. J. Haematol. 108:346-356 (2000).

Stone, R. M., et al., "Myelodysplastic Syndrome as a Late Complication Following Autologous Bone Marrow Transplantation for Non-Hodgkin's Lymphoma," J. Clin. Oncol. 12:2535-2542 (1994).

Subramanian, A., et al., "Gene Set Enrichment Analysis: A Knowledge-Based Approach for Interpreting Genome-Wide Expression Profile," PNAS 102(43):15545-15550 (2005).

United States Patent and Trademark Office, International Search Report and Written Opinion dated Jun. 20, 2012 for PCT/US11/64040.

* cited by examiner

Figure 6

| Gene ID | Description |
|---|---|
| NR4A2 | nuclear receptor subfamily 4, group A, member 2 |
| FOS | v-fos FBJ murine osteosarcoma viral oncogene homolog |
| EGR1 | early growth response 1 |
| CARD6 | caspase recruitment domain family, member 6 |
| PEX11B | peroxisomal biogenesis factor 11 beta |
| EGR3 | early growth response 3 |
| EGR4 | early growth response 4 |
| MRPL15 | mitochondrial ribosomal protein L15 |
| SLC7A11 | solute carrier family 7, (cationic amino acid transporter, y+ system) member 11 |
| REEP1 | receptor accessory protein 1 |
| FOSB | FBJ murine osteosarcoma viral oncogene homolog B |
| GOLGA5 | golgi autoantigen, golgin subfamily a, 5 |
| ACTL6A | actin-like 6A |
| GOLPH3L | golgi phosphoprotein 3-like |
| CCDC99 | coiled-coil domain containing 99 |
| SMAD7 | SMAD family member 7 |
| SHMT2 | serine hydroxymethyltransferase 2 (mitochondrial) |
| LRPPRC | leucine-rich PPR-motif containing |
| CDCA4 | cell division cycle associated 4 |
| PDIA4 | protein disulfide isomerase family A, member 4 |
| GOT1 | glutamic-oxaloacetic transaminase 1, soluble (aspartate aminotransferase 1) |
| RTN3 | reticulon 3 |
| KLF2 | Kruppel-like factor 2 (lung) |
| JUN | jun oncogene |
| STK17B | serine/threonine kinase 17b |
| PSMC2 | proteasome (prosome, macropain) 26S subunit, ATPase, 2 |
| LRBA | LPS-responsive vesicle trafficking, beach and anchor containing |
| XPOT | exportin, tRNA (nuclear export receptor for tRNAs) |
| ZYG11B | zyg-11 homolog B (C. elegans) |
| ZNF137 | zinc finger protein 137 |
| GEM | GTP binding protein overexpressed in skeletal muscle |
| PGRMC2 | progesterone receptor membrane component 2 |
| ARL6IP6 | ADP-ribosylation-like factor 6 interacting protein 6 |
| SLC2A3P1 | Solute carrier family 2 (facilitated glucose transporter), member 3 pseudogene 1 |
| NR4A3 | nuclear receptor subfamily 4, group A, member 3 |
| RGS2 | regulator of G-protein signaling 2, 24kDa |
| NRIP3 | nuclear receptor interacting protein 3 |
| SLC26A2 | solute carrier family 26 (sulfate transporter), member 2 |

| Serial No. | Primary Dx | Age at HCT | Sex | Race/ ethnicity | Stem cell mobilization | Stem cell dose infused | Conditioning regimen | Time from aHCT to t-MDS/AML (days) | Cytogenetics | Morphology | WBC | HGB | PLT | Cytopenias |
|---|---|---|---|---|---|---|---|---|---|---|---|---|---|---|
| 5538 | HD | 49 | F | W | GCSF, VP-16 | 2 | BCNU, VP-16, cytoxan | 1782 days | -7, inv(9) | MDS | 5.78 | 9.9 | 53 | anemia, thrombocytopenia |
| 5535 | NHL | 50 | F | W | GCSF | 1.98 | TBI, VP-16, cytoxan | 2134 days | add(3q), t(1;2), t(12;15), -3, -4, -7 | MDS | 1.3 | 8.9 | 48 | pancytopenia |
| 5396 | HD | 46 | M | W | GCSF, CTX | 4.8 | TBI, VP-16, cytoxan | 2996 days | del(7q, 18q, 1q) monosomy 7, 13) | MDS | 6.9 | 7.9 | 49 | anemia, thrombocytopenia |
| 95001 | HD | 54 | M | B | GCSF | 2.79 | BCNU, VP-16, cytoxan | 149 days | Monosomy 7, del (13q) | MDS | 7 | 11.4 | 71 | anemia, thrombocytopenia |
| 95002 | NHL | 66 | M | W | GCSF | 2.83 | Ara-C, BCNU, Melphalan, VP-16 | 756 days | t(1;3), (p13;q13), -Y | AML | 4 | 10.2 | 82 | anemia, thrombocytopenia |
| 95003 | HD | 57 | M | H | GCSF | 4.96 | TBI, VP-16, cytoxan | 1827 days | NA | RAEB | 0.8 | 8.4 | 29 | pancytopenia |
| 95005 | HD | 64 | M | W | GCSF | 0.24 | TBI, VP-16, cytoxan | 560 days | -7, del(8q), del(17q) | MDS | 3.1 | 11 | 55 | pancytopenia |
| 95006 | NHL | 66 | M | W | GCSF, CTX | 2.74 | Cytoxan, BCNU, VP-16 | 1065 days | del (3), -5, -7, 11;q23 | RAEB/AML | 4 | 10 | 213 | anemia |
| 95007 | NHL | 35 | M | W | GCSF, VP-16 | 3.89 | TBI, VP-16, cytoxan | 3363 days | -5, -7A, -20, del (13q), add(7), del(5q) | RAEB | 2.3 | 9.1 | 25 | pancytopenia |
| 95008 | HD | 40 | M | W | GCSF | 4.45 | TBI, VP-16, cytoxan | 1746 days | del(5q, 10q, 17p), t(1;8), 45;X,Y | MDS | 1.3 | 7.8 | 91 | anemia, thrombocytopenia |
| 95009 | NHL | 63 | M | B | GCSF | 5.57 | BCNU, VP-16, cytoxan | 3411 days | (+13) | MDS | 4.2 | 9.9 | 88 | leukopenia, thrombocytopenia |
| 95010 | NHL | 29 | F | W | GCSF, VP-16 | 16.07 | BCNU, VP-16, Cytoxan | 583 days | t(8;21), add(4), del(5), del(6), add(12) | AML | 2.8 | 13.1 | 70 | pancytopenia |
| 95011 | HD | 48 | M | W | GCSF, CTX | 3.4 | TBI, VP-16, cytoxan (2nd) | 854 days | add(5), del(7q), -2, -9 | AML | 1.2 | 13.0 | 12 | pancytopenia |
| 211 | NHL | 19 | M | W | GCSF | 2 | melphalan (1st) BCNU, VP-16, cytoxan (2nd) | 333 days | monosomy 7 | RAEB | 6 | 15.9 | 173 | normal |
| 5860 | NHL | 62 | M | W | GCSF | 9.75 | BCNU, VP-16, Cytoxan | 3059 days | NA | MDS | 6.4 | 10.6 | 135 | anemia, thrombocytopenia |
| 95009 | HD | 34 | M | W | GCSF | 3.09 | TBI, VP-16, cytoxan | 1481 days | | AML | 3.3 | 8.5 | 70 | pancytopenia |

Abbreviations: HL=Hodgkins lymphoma; NHL=Non-Hodgkins lymphoma; HCT= hematopoietic cell transplantation, PBSC=peripheral blood stem cells; SD=standard deviation, G-CSF=granulocyte colony stimulating factor; TBI=total body irradiation, NA=not available

Figure 14

| Gene set | Training set | | Test Set | |
|---|---|---|---|---|
| | NES | FDR q-val | NES | FDR q-val |
| *Enriched in Cases* | | | | |
| G-Protein coupled receptors | | | | |
| HSA04080_NEUROACTIVE_LIGAND_RECEPTOR_INTERACTION | 2.83 | <0.001 | 3.89 | <0.001 |
| GPCRDB_CLASS_A_RHODOPSIN_LIKE | 2.60 | <0.001 | 3.35 | <0.001 |
| GPCRS_CLASS_A_RHODOPSIN_LIKE | 2.52 | <0.001 | 2.83 | <0.001 |
| MONOAMINE_GPCRS | 2.32 | 0.003 | 2.62 | <0.001 |
| PEPTIDE_GPCRS | 2.21 | 0.005 | 2.86 | <0.001 |
| Hematopoietic regulation | | | | |
| HALMOS_CEBP_DN | 2.33 | 0.003 | 1.73 | 0.079 |
| HOX_GENES | 1.89 | 0.036 | 1.06 | 0.738 |
| HSA04340_HEDGEHOG_SIGNALING_PATHWAY | 1.76 | 0.058 | 2.15 | 0.005 |
| Cell adhesion/communication | | | | |
| HSA01430_CELL_COMMUNICATION | 2.05 | 0.009 | 2.86 | <0.001 |
| CELL_ADHESION | 1.63 | 0.108 | 1.82 | 0.061 |
| Xenobiotic metabolism | | | | |
| GAMMA_HEXACHLOROCYCLOHEXANE_DEGRADATION | 2.04 | 0.009 | 2.01 | 0.018 |
| | | | | |
| *Enriched in controls (reduced in cases)* | | | | |
| Mitochondria and oxidative phosphorylation | | | | |
| HUMAN_MITODB_6_2002 | -2.92 | <0.001 | -3.93 | <0.001 |
| HSA00190_OXIDATIVE_PHOSPHORYLATION | -2.88 | <0.001 | -3.01 | <0.001 |
| ELECTRON_TRANSPORT_CHAIN | -2.85 | <0.001 | -3.17 | <0.001 |
| MITOCHONDRIA | -2.84 | <0.001 | -3.85 | <0.001 |
| MOOTHA_VOXPHOS | -2.74 | <0.001 | -3.08 | <0.001 |
| OXIDATIVE_PHOSPHORYLATION | -2.58 | <0.001 | -2.67 | <0.001 |
| Ribosomes | | | | |
| HSA03010_RIBOSOME | -3.02 | <0.001 | -4.06 | <0.001 |
| RIBOSOMAL_PROTEINS | -3.01 | <0.001 | -3.77 | <0.001 |
| tRNA biosynthesis | | | | |
| TRNA_SYNTHETASES | -2.68 | <0.001 | -2.71 | <0.001 |
| AMINOACYL_TRNA_BIOSYNTHESIS | -2.41 | <0.001 | -2.74 | <0.001 |
| HSA00970_AMINOACYL_TRNA_BIOSYNTHESIS | -2.27 | <0.001 | -2.76 | <0.001 |
| Proteasomal pathway | | | | |
| PROTEASOMEPATHWAY | -2.47 | <0.001 | -3.14 | <0.001 |
| HSA03050_PROTEASOME | -2.47 | <0.001 | -2.69 | <0.001 |
| PROTEASOME_DEGRADATION | -2.32 | <0.001 | -2.52 | <0.001 |
| Cell cycle regulation | | | | |
| DNA_REPLICATION_REACTOME | -2.37 | <0.001 | -2.64 | <0.001 |
| P21_P53_MIDDLE_DN | -2.26 | <0.001 | -1.45 | 0.107 |
| P21_P53_ANY_DN | -2.16 | 6.79E-04 | -2.33 | <0.001 |
| SERUM_FIBROBLAST_CELLCYCLE | -2.14 | 0.014456 | -1.74 | 0.029 |
| CELL_CYCLE_KEGG | -1.91 | 0.005942 | -1.97 | 0.008 |
| Metabolism | | | | |
| KREBS_TCA_CYCLE | -2.46 | <0.001 | -2.46 | <0.001 |
| HSA00020_CITRATE_CYCLE | -2.23 | 2.31E-04 | -2.55 | <0.001 |
| PENG_LEUCINE_DN | -2.22 | 4.46E-04 | -3.65 | <0.001 |
| HSA00252_ALANINE_AND_ASPARTATE_METABOLISM | -2.05 | 0.001727 | -1.00 | 0.535 |
| PROPANOATE_METABOLISM | -1.98 | 0.003869 | -2.82 | <0.001 |
| Hematopoietic stem cells | | | | |
| HSC_INTERMEDIATEPROGENITORS_ADULT | -2.42 | <0.001 | -3.15 | <0.001 |
| HSC_LATEPROGENITORS_ADULT | -2.36 | <0.001 | -3.73 | <0.001 |
| HSC_INTERMEDIATEPROGENITORS_SHARED | -2.35 | <0.001 | -3.19 | <0.001 |
| HSC_LATEPROGENITORS_FETAL | -2.31 | <0.001 | -3.61 | <0.001 |
| HSC_LATEPROGENITORS_SHARED | -2.28 | <0.001 | -3.87 | <0.001 |
| DNA repair | | | | |
| BRENTANI_REPAIR | -2.23 | <0.001 | -1.68 | 0.039 |

| Enriched in cases | | | Enriched in controls | | |
|---|---|---|---|---|---|
| TF | | FDR | TF | | FDR |
| POU2F1 (OCT1) | 2.625117 | 0 | ELK1 | -2.32 | 0.000 |
| GFI1 | 2.573659 | 0 | NFE2L2 | -2.19 | 0.000 |
| ONECUT1 | 2.465438 | 0 | SREBP1 | -2.13 | 0.000 |
| POU3F2 (OCT7) | 2.406619 | 0 | GABP | -2.11 | 0.000 |
| FOXA1 | 2.390322 | 0 | ETS1 | -1.97 | 0.000 |
| PRRX2 | 2.385213 | 0 | YY1 | -1.78 | 0.005 |
| LHX3 | 2.384263 | 0 | NRF1 | -1.67 | 0.015 |
| POU2F1 (OCT1) | 2.34711 | 0 | YY1 | -1.65 | 0.016 |
| POU1F1 (PIT1) | 2.323895 | 0 | E2F1 | -1.64 | 0.018 |
| POU2F1 (OCT1) | 2.310564 | 0 | E2F1 | -1.57 | 0.035 |

Motifs for unknown TF excluded
Abbreviations: TF=transcription factor; NES=normalized enrichment score; FDR=false discovery rate

Figure 18

| Ingenuity Canonical Pathways | P-value | FDR |
|---|---|---|
| Oxidative Phosphorylation | 1.45E-06 | 0.0001798 |
| Mitochondrial Dysfunction | 5.25E-06 | 0.0003255 |
| Alanine and Aspartate Metabolism | 0.000955 | 0.03947333 |
| Citrate Cycle | 0.00295 | 0.08618 |
| Pentose Phosphate Pathway | 0.0038 | 0.08618 |
| Aminoacyl-tRNA Biosynthesis | 0.00417 | 0.08618 |
| p53 Signaling | 0.00501 | 0.08874857 |
| Ubiquinone Biosynthesis | 0.00617 | 0.095635 |
| Hereditary Breast Cancer Signaling | 0.00759 | 0.10457333 |
| Protein Ubiquitination Pathway | 0.00871 | 0.108004 |
| TNFR1 Signaling | 0.0105 | 0.11836364 |
| Regulation of eIF4 and p70S6K Signaling | 0.0132 | 0.1364 |
| EIF2 Signaling | 0.0148 | 0.14116923 |
| Mechanisms of Viral Exit from Host Cells | 0.0204 | 0.18068571 |
| Glycolysis/Gluconeogenesis | 0.0269 | 0.22237333 |
| Granzyme B Signaling | 0.0316 | 0.2449 |
| Starch and Sucrose Metabolism | 0.0427 | 0.26417391 |
| Nucleotide Excision Repair Pathway | 0.0437 | 0.26417391 |
| Glyoxylate and Dicarboxylate Metabolism | 0.0447 | 0.26417391 |
| Metabolism of Xenobiotics by Cytochrome P450 | 0.0468 | 0.26417391 |
| TNFR2 Signaling | 0.0479 | 0.26417391 |
| ATM Signaling | 0.049 | 0.26417391 |
| Induction of Apoptosis by HIV1 | 0.049 | 0.26417391 |

Abbreviations: FDR=false discovery rate

Figure 19

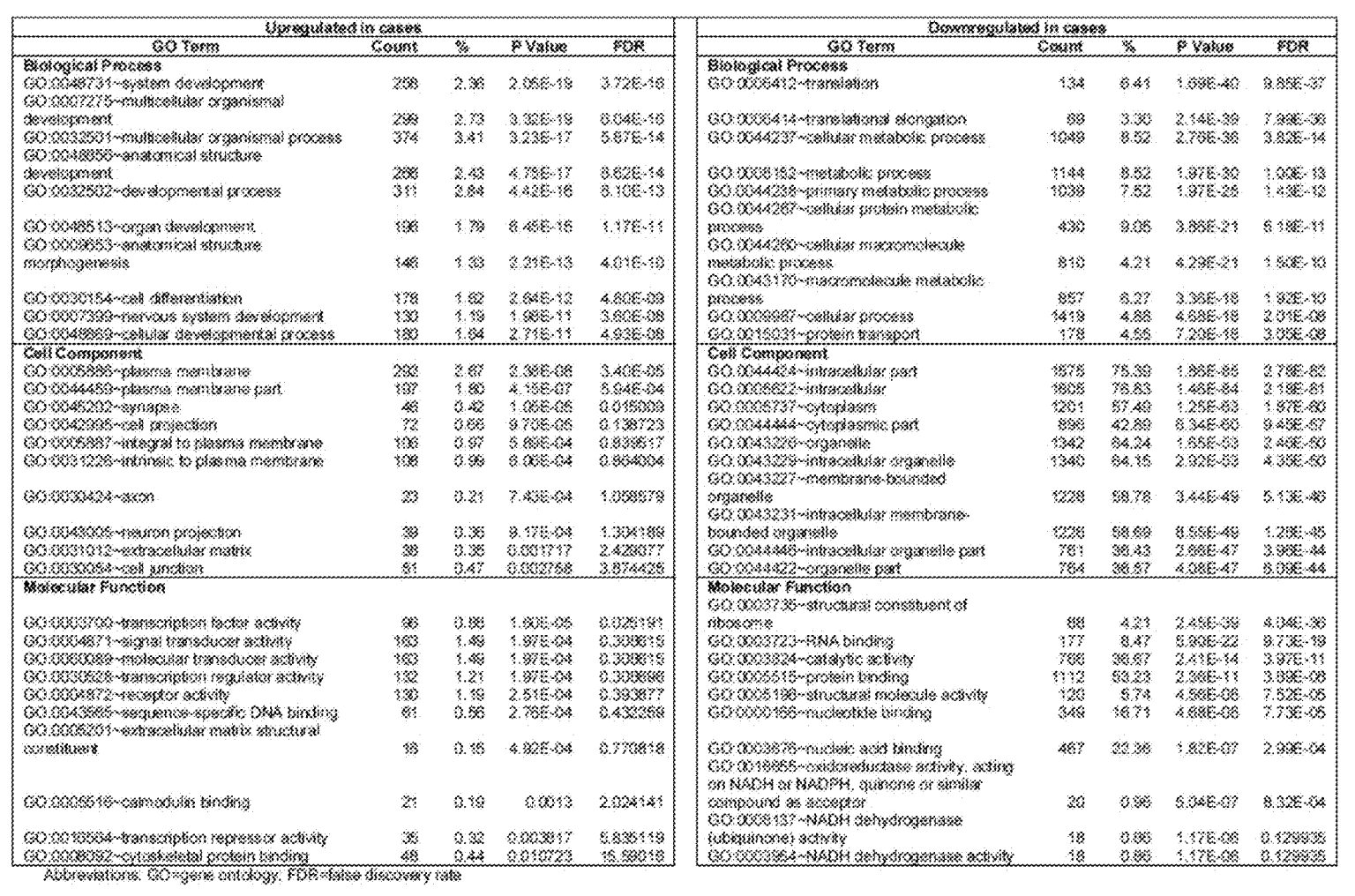

| Upregulated in cases | | | | |
|---|---|---|---|---|
| GO Term | Count | % | P Value | FDR |
| Biological Process | | | | |
| GO:0048731~system development | 258 | 2.36 | 2.05E-19 | 3.72E-16 |
| GO:0007275~multicellular organismal development | 299 | 2.73 | 3.32E-19 | 6.04E-16 |
| GO:0032501~multicellular organismal process | 374 | 3.41 | 3.23E-17 | 5.87E-14 |
| GO:0048856~anatomical structure development | 266 | 2.43 | 4.75E-17 | 8.62E-14 |
| GO:0032502~developmental process | 311 | 2.84 | 4.42E-16 | 8.10E-13 |
| GO:0048513~organ development | 196 | 1.79 | 6.45E-15 | 1.17E-11 |
| GO:0009653~anatomical structure morphogenesis | 146 | 1.33 | 2.21E-13 | 4.01E-10 |
| GO:0030154~cell differentiation | 178 | 1.62 | 2.64E-12 | 4.80E-09 |
| GO:0007399~nervous system development | 130 | 1.19 | 1.98E-11 | 3.60E-08 |
| GO:0048869~cellular developmental process | 180 | 1.64 | 2.71E-11 | 4.93E-08 |
| Cell Component | | | | |
| GO:0005886~plasma membrane | 293 | 2.67 | 2.39E-08 | 3.40E-05 |
| GO:0044459~plasma membrane part | 197 | 1.80 | 4.15E-07 | 5.94E-04 |
| GO:0045202~synapse | 46 | 0.42 | 1.06E-05 | 0.015009 |
| GO:0042995~cell projection | 72 | 0.66 | 9.70E-05 | 0.138723 |
| GO:0005887~integral to plasma membrane | 106 | 0.97 | 5.89E-04 | 0.839517 |
| GO:0031226~intrinsic to plasma membrane | 108 | 0.99 | 6.06E-04 | 0.864004 |
| GO:0030424~axon | 23 | 0.21 | 7.43E-04 | 1.058979 |
| GO:0043005~neuron projection | 39 | 0.36 | 9.17E-04 | 1.304189 |
| GO:0031012~extracellular matrix | 39 | 0.36 | 0.001717 | 2.428077 |
| GO:0030054~cell junction | 51 | 0.47 | 0.002758 | 3.874429 |
| Molecular Function | | | | |
| GO:0003700~transcription factor activity | 96 | 0.88 | 1.80E-05 | 0.025191 |
| GO:0004871~signal transducer activity | 163 | 1.49 | 1.97E-04 | 0.308815 |
| GO:0060089~molecular transducer activity | 163 | 1.49 | 1.97E-04 | 0.308815 |
| GO:0030528~transcription regulator activity | 132 | 1.21 | 1.97E-04 | 0.308866 |
| GO:0004872~receptor activity | 130 | 1.19 | 2.51E-04 | 0.393877 |
| GO:0043565~sequence-specific DNA binding | 61 | 0.56 | 2.76E-04 | 0.432359 |
| GO:0005201~extracellular matrix structural constituent | 16 | 0.15 | 4.92E-04 | 0.770818 |
| GO:0005516~calmodulin binding | 21 | 0.19 | 0.0013 | 2.024141 |
| GO:0016564~transcription repressor activity | 35 | 0.32 | 0.003817 | 5.835119 |
| GO:0008092~cytoskeletal protein binding | 48 | 0.44 | 0.010723 | 15.58018 |

| Downregulated in cases | | | | |
|---|---|---|---|---|
| GO Term | Count | % | P Value | FDR |
| Biological Process | | | | |
| GO:0006412~translation | 134 | 6.41 | 1.59E-40 | 9.85E-37 |
| GO:0006414~translational elongation | 69 | 3.30 | 2.14E-39 | 7.99E-36 |
| GO:0044237~cellular metabolic process | 1049 | 8.52 | 2.76E-36 | 3.82E-14 |
| GO:0008152~metabolic process | 1144 | 8.52 | 1.97E-30 | 1.00E-13 |
| GO:0044238~primary metabolic process | 1039 | 7.52 | 1.97E-25 | 1.43E-13 |
| GO:0044267~cellular protein metabolic process | 430 | 9.05 | 3.85E-21 | 6.18E-11 |
| GO:0044260~cellular macromolecule metabolic process | 810 | 4.21 | 4.29E-21 | 1.60E-10 |
| GO:0043170~macromolecule metabolic process | 857 | 6.27 | 3.36E-18 | 1.92E-10 |
| GO:0009987~cellular process | 1419 | 4.88 | 4.68E-18 | 2.01E-09 |
| GO:0015031~protein transport | 178 | 4.55 | 7.20E-18 | 3.05E-09 |
| Cell Component | | | | |
| GO:0044424~intracellular part | 1575 | 75.39 | 1.89E-85 | 2.79E-82 |
| GO:0005622~intracellular | 1605 | 76.83 | 1.46E-84 | 3.18E-81 |
| GO:0005737~cytoplasm | 1201 | 57.49 | 1.25E-63 | 1.97E-60 |
| GO:0044444~cytoplasmic part | 896 | 42.89 | 6.34E-60 | 9.45E-57 |
| GO:0043226~organelle | 1342 | 64.24 | 1.65E-53 | 2.46E-50 |
| GO:0043229~intracellular organelle | 1340 | 64.15 | 2.92E-53 | 4.35E-50 |
| GO:0043227~membrane-bounded organelle | 1228 | 58.78 | 3.44E-49 | 5.13E-46 |
| GO:0043231~intracellular membrane-bounded organelle | 1226 | 58.69 | 8.55E-49 | 1.28E-45 |
| GO:0044446~intracellular organelle part | 761 | 36.43 | 2.66E-47 | 3.96E-44 |
| GO:0044422~organelle part | 764 | 36.57 | 4.08E-47 | 6.09E-44 |
| Molecular Function | | | | |
| GO:0003735~structural constituent of ribosome | 88 | 4.21 | 2.45E-39 | 4.04E-36 |
| GO:0003723~RNA binding | 177 | 8.47 | 5.90E-22 | 9.73E-19 |
| GO:0003824~catalytic activity | 766 | 36.67 | 2.41E-14 | 3.97E-11 |
| GO:0005515~protein binding | 1112 | 53.23 | 2.36E-11 | 3.89E-08 |
| GO:0005198~structural molecule activity | 120 | 5.74 | 4.56E-08 | 7.52E-05 |
| GO:0000166~nucleotide binding | 349 | 16.71 | 4.69E-08 | 7.73E-05 |
| GO:0003676~nucleic acid binding | 467 | 22.36 | 1.82E-07 | 2.99E-04 |
| GO:0016655~oxidoreductase activity, acting on NADH or NADPH, quinone or similar compound as acceptor | 20 | 0.96 | 5.04E-07 | 8.32E-04 |
| GO:0008137~NADH dehydrogenase (ubiquinone) activity | 18 | 0.86 | 1.17E-06 | 0.129935 |
| GO:0003954~NADH dehydrogenase activity | 18 | 0.86 | 1.17E-06 | 0.129935 |

Abbreviations: GO=gene ontology; FDR=false discovery rate

Figure 21

Increased in t-MDS/AML PBSC

| NAME | NES | FDR q-val |
|---|---|---|
| HSA04080_NEUROACTIVE_LIGAND_RECEPTOR_INTERACTION | 2.650698 | <0.001 |
| GPCRDB_CLASS_A_RHODOPSIN_LIKE | 2.611210 | <0.001 |
| GPCRS_CLASS_A_RHODOPSIN_LIKE | 2.443164 | <0.001 |
| HSA01430_CELL_COMMUNICATION | 2.365203 | 0.002887 |
| MOREAUX_TACI_HI_VS_LOW_UP | 2.317167 | 0.003582 |
| PEPTIDE_GPCRS | 2.313133 | 0.002918 |
| HUMAN_TISSUE_LIVER | 2.285419 | 0.002501 |
| CARIES_PULP_DN | 2.230311 | 0.003687 |
| MONOAMINE_GPCRS | 2.170755 | 0.03667 |
| HALMOS_CEBP_DN | 2.043597 | 0.017535 |
| GAMMA_HEXACHLOROCYCLOHEXANE_DEGRADATION | 1.973882 | 0.025149 |
| UVC_HIGH_ALL_UP | 1.967079 | 0.102658 |
| IGF_VS_PDGF_UP | 1.95393 | 0.026827 |
| GH_EXOGENOUS_MIDDLE_UP | 1.935157 | 0.026892 |
| VEGF_HUVEC_30MIN_UP | 1.872544 | 0.040946 |
| BCQUEST_CD31PLUS_VS_CD31MINUS_DN | 1.845108 | 0.051132 |
| GEFFY_CEBP_TARGETS | 1.828249 | 0.063381 |
| LEE_MYC_DN | 1.824463 | 0.051173 |
| VEGF_MMMEC_8HRS_UP | 1.818545 | 0.04997 |
| STAEGE_EFTS_UP | 1.811746 | 0.050798 |
| GH_EXOGENOUS_ANY_UP | 1.794956 | 0.054718 |
| ACSP_DIFF_CLUSTER2 | 1.79459 | 0.052229 |
| LVAD_HEARTFAILURE_UP | 1.735005 | 0.077574 |
| SCHURINGA_STAT5A_UP | 1.726985 | 0.075347 |
| VEGF_MMMEC_12HRS_UP | 1.720316 | 0.078354 |
| FERRANDO_T_CELL_DIFFERENTIATION_PATHWAY | 1.717426 | 0.076952 |
| YAO_P4_KO_VS_WT_UP | 1.711202 | 0.07813 |
| STRIATED_MUSCLE_CONTRACTION | 1.709863 | 0.075973 |
| HSA05217_BASAL_CELL_CARCINOMA | 1.704732 | 0.076221 |
| HOX_GENES | 1.697705 | 0.079486 |
| CMV_HCMV_8HRS_DN | 1.692072 | 0.079003 |
| HINATA_NFKB_DN | 1.684333 | 0.081244 |
| EMT_DN | 1.672483 | 0.084999 |
| NUCLEAR_RECEPTORS | 1.657348 | 0.08633 |
| CMV_HCMV_TIMECOURSE_8HRS_DN | 1.65698 | 0.084048 |
| RORIE_ES_PNET_DN | 1.641662 | 0.096376 |
| TSADAC_PANC50_UP | 1.633858 | 0.1069 |
| KANG_TERT_DN | 1.611256 | 0.114336 |
| FRASOR_ER_UP | 1.598205 | 0.122511 |
| HSA00602_GLYCOSPHINGOLIPID_BIOSYNTHESIS_NEO_LACTOSERIES | 1.595793 | 0.122301 |
| IDX_TSA_UP_CLUSTER1 | 1.577756 | 0.135234 |
| JECHLINGER_EMT_DN | 1.573269 | 0.134457 |
| TAKEDA_NUP8_HOXA9_8H_UP | 1.556179 | 0.1491 |
| HSA04340_HEDGEHOG_SIGNALING_PATHWAY | 1.554442 | 0.147228 |
| GH_EXOGENOUS_LATE_UP | 1.551692 | 0.146635 |
| HSA04512_ECM_RECEPTOR_INTERACTION | 1.550069 | 0.144328 |
| CALCIUM_REGULATION_IN_CARDIAC_CELLS | 1.543701 | 0.145139 |
| BRENTANI_TRANSCRIPTION_FACTORS | 1.531898 | 0.154135 |
| | 1.530191 | 0.153304 |
| | 1.51914 | 0.16253 |

Increased in control PBSC

| NAME | NES | FDR q-val |
|---|---|---|
| ELECTRON_TRANSPORT_CHAIN | -3.15933 | <0.001 |
| MOOTHA_VOXPHOS | -3.0799 | <0.001 |
| HSA00190_OXIDATIVE_PHOSPHORYLATION | -3.04708 | <0.001 |
| HUMAN_MITODB_6_2002 | -2.96652 | <0.001 |
| MITOCHONDRIA | -2.92255 | <0.001 |
| PROTEASOMEPATHWAY | -2.89423 | <0.001 |
| RIBOSOMAL_PROTEINS | -2.87936 | <0.001 |
| HSA03010_RIBOSOME | -2.8533 | <0.001 |
| TARTE_PLASMA_BLASTIC | -2.83713 | <0.001 |
| CANCER_UNDIFFERENTIATED_META_UP | -2.75819 | <0.001 |
| PENG_RAPAMYCIN_DN | -2.71085 | <0.001 |
| CANTHARIDIN_DN | -2.70678 | <0.001 |
| MOREAUX_TACI_HI_IN_PPC_UP | -2.69827 | <0.001 |
| MOREAUX_TACI_HI_VS_LOW_DN | -2.66619 | <0.001 |
| OXIDATIVE_PHOSPHORYLATION | -2.6729 | <0.001 |
| HCC_SURVIVAL_GOOD_VS_POOR_DN | -2.66591 | <0.001 |
| TCA | -2.65311 | <0.001 |
| UVB_SCC_UP | -2.63461 | <0.001 |
| HEARTFAILURE_ATRIA_DN | -2.59436 | <0.001 |
| PENG_GLUTAMINE_DN | -2.57098 | <0.001 |
| BRCA1_OVEREXP_DN | -2.55692 | <0.001 |
| TRNA_SYNTHETASES | -2.53694 | <0.001 |
| ROME_INSULIN_3F_UP | -2.53322 | <0.001 |
| KREBS_TCA_CYCLE | -2.52253 | <0.001 |
| JAIN_NEMO_DIFF | -2.46564 | <0.001 |
| IDX_TSA_UP_CLUSTER3 | -2.48481 | <0.001 |
| PGC | -2.47819 | <0.001 |
| CMV_IE86_UP | -2.47462 | <0.001 |
| RUTELLA_HEPATGFSNDCS_UP | -2.46868 | <0.001 |
| PROTEASOME_DEGRADATION | -2.46318 | <0.001 |
| HSA03050_PROTEASOME | -2.44659 | <0.001 |
| CHANG_SERUM_RESPONSE_UP | -2.44393 | <0.001 |
| AMINOACYL_TRNA_BIOSYNTHESIS | -2.44473 | <0.001 |
| DNA_REPLICATION_REACTOME | -2.44159 | <0.001 |
| PRMT5_KD_UP | -2.4094 | <0.001 |
| SERUM_FIBROBLAST_CORE_UP | -2.40287 | <0.001 |
| WIELAND_HEPATITIS_B_INDUCED | -2.39869 | <0.001 |
| HSC_INTERMEDIATEPROGENITORS_SHARED | -2.38436 | <0.001 |
| HSC_LATEPROGENITORS_SHARED | -2.37883 | <0.001 |
| HSC_LATEPROGENITORS_ADULT | -2.37015 | <0.001 |
| UVB_NHEK2_UP | -2.36861 | 2.55E-04 |
| HEDACL_COLON_CURG4HR3_UP | -2.36775 | 2.50E-04 |
| HSC_INTERMEDIATEPROGENITORS_SHARED | -2.36090 | 2.45E-04 |
| HSC_INTERMEDIATEPROGENITORS_ADULT | -2.35439 | 2.40E-04 |
| IDX_TSA_UP_CLUSTERS | -2.35246 | 2.35E-04 |
| RADAEVA_IFNA_UP | | |
| FERRANDO_MLL_T_ALL_DN | | |
| RCC_NL_UP | | |
| HSC_LATEPROGENITORS_FETAL | | |
| SHIPP_FL_VS_DLBCL_DN | | |
| HSA00970_AMINOACYL_TRNA_BIOSYNTHESIS | | |

Figure 24

| | NES | FDR q-val |
|---|---|---|
| *Enriched in Cases* | | |
| G-Protein coupled receptors | | |
| HSA04080_NEUROACTIVE_LIGAND_RECEPTOR_INTERACTION | 3.11 | <0.001 |
| GPCRDB_CLASS_A_RHODOPSIN_LIKE | 2.70 | <0.001 |
| GPCRS_CLASS_A_RHODOPSIN_LIKE | 2.69 | <0.001 |
| MONOAMINE_GPCRS | 2.50 | <0.001 |
| PEPTIDE_GPCRS | 1.80 | 0.143 |
| Cell adhesion/communication | | |
| HSA01430_CELL_COMMUNICATION | 2.59 | <0.001 |
| HSA04512_ECM_RECEPTOR_INTERACTION | 2.22 | 0.001 |
| HSA04514_CELL_ADHESION_MOLECULES | 1.94 | 0.016 |
| Hematopoietic regulation | | |
| HSA04340_HEDGEHOG_SIGNALING_PATHWAY | 2.04 | 0.012 |
| *Enriched in controls (reduced in cases)* | | |
| Cell cycle regulation/checkpoints | | |
| SERUM_FIBROBLAST_CELLCYCLE | -3.34 | <0.001 |
| DNA_REPLICATION_REACTOME | -3.15 | <0.001 |
| P21_P53_ANY_DN | -3.12 | <0.001 |
| P21_P53_MIDDLE_DN | -2.87 | <0.001 |
| CELL_CYCLE | -2.77 | <0.001 |
| CELL_CYCLE_KEGG | -2.70 | <0.001 |
| HSA04110_CELL_CYCLE | -2.63 | <0.001 |
| DNA_DAMAGE_SIGNALING | -2.45 | <0.001 |
| GOLDRATH_CELLCYCLE | -2.42 | 0.002 |
| Hematopoietic stem cells | | |
| HSC_LATEPROGENITORS_ADULT | -2.60 | <0.001 |
| HSC_LATEPROGENITORS_SHARED | -2.58 | <0.001 |
| HSC_LATEPROGENITORS_FETAL | -2.57 | <0.001 |
| HSC_INTERMEDIATEPROGENITORS_ADULT | -2.51 | <0.001 |
| HSC_EARLYPROGENITORS_SHARED | -2.47 | <0.001 |
| HSC_INTERMEDIATEPROGENITORS_SHARED | -2.39 | <0.001 |
| Metabolism | | |
| PENG_LEUCINE_DN | -2.56 | <0.001 |
| KREBS_TCA_CYCLE | -2.55 | <0.001 |
| PENG_GLUTAMINE_DN | -2.43 | <0.001 |
| HSA00020_CITRATE_CYCLE | -2.26 | <0.001 |
| Mitochondria and oxidative phosphorylation | | |
| MITOCHONDRIA | -2.66 | <0.001 |
| HUMAN_MITODB_6_2002 | -2.58 | <0.001 |
| ELECTRON_TRANSPORT_CHAIN | -2.42 | <0.001 |
| Proteasome pathway | | |
| PROTEASOMEPATHWAY | -2.30 | <0.001 |
| PROTEASOME | -2.16 | <0.001 |
| DNA repair | | |
| BRENTANI_REPAIR | -2.91 | <0.001 |

Figure 25

(Illegible low-resolution table content)

A  DNA Repair    B  Cell Communication    C  DNA Replication Reactome

Figure 27

| Enriched in cases | | | Enriched in controls | | |
|---|---|---|---|---|---|
| TF | NES | FDR q-value | TF | NES | FDR q-value |
| NRSF | 2.64 | <0.001 | E2F1 | -2.36 | <0.001 |
| POU2F1 (OCT1) | 2.24 | <0.001 | ELK1 | -2.33 | <0.001 |
| HNF1 | 2.24 | <0.001 | E2F1 | -2.27 | <0.001 |
| POU2F1 (OCT1) | 2.23 | <0.001 | E2F1 | -2.26 | <0.001 |
| HNF1 | 2.21 | <0.001 | E2F4 | -2.26 | <0.001 |
| GFI1 | 2.21 | <0.001 | E2F1 | -2.26 | <0.001 |
| GATA1 | 2.19 | <0.001 | E2F1 | -2.26 | <0.001 |
| TAL1 | 2.11 | <0.001 | YY1 | -2.18 | <0.001 |
| GATA1 | 2.09 | <0.001 | E2F1 | -2.18 | <0.001 |
| NR3C1 | 2.08 | <0.001 | SREBP1 | -2.17 | <0.001 |

Figure 28

| Ingenuity Canonical Pathways | P-value | FDR |
|---|---|---|
| Role of BRCA1 in DNA Damage Response | 3.55E-06 | 0.000583675 |
| Hereditary Breast Cancer Signaling | 6.31E-06 | 0.000583675 |
| Role of CHK Proteins in Cell Cycle Checkpoint Control | 3.39E-05 | 0.0020905 |
| Pyrimidine Metabolism | 0.000692 | 0.032005 |
| p53 Signaling | 0.00288 | 0.10656 |
| Antiproliferative Role of TOB in T Cell Signaling | 0.01 | 0.290714286 |
| EIF2 Signaling | 0.011 | 0.290714286 |
| Cell Cycle: G2/M DNA Damage Checkpoint Regulation | 0.0129 | 0.2923 |
| Leptin Signaling in Obesity | 0.0145 | 0.2923 |
| Citrate Cycle | 0.0158 | 0.2923 |
| IGF-1 Signaling | 0.0174 | 0.292636364 |
| Synthesis and Degradation of Ketone Bodies | 0.0219 | 0.29715625 |
| IL-2 Signaling | 0.0234 | 0.29715625 |
| PPARα/RXRα Activation | 0.0251 | 0.29715625 |
| Pantothenate and CoA Biosynthesis | 0.0251 | 0.29715625 |
| Protein Ubiquitination Pathway | 0.0257 | 0.29715625 |
| Purine Metabolism | 0.0339 | 0.364861111 |
| Small Cell Lung Cancer Signaling | 0.0355 | 0.364861111 |
| Molecular Mechanisms of Cancer | 0.0417 | 0.37185 |
| Pancreatic Adenocarcinoma Signaling | 0.0447 | 0.37185 |
| JAK/Stat Signaling | 0.0447 | 0.37185 |
| ATM Signaling | 0.0479 | 0.37185 |
| IL-22 Signaling | 0.049 | 0.37185 |

Figure 29

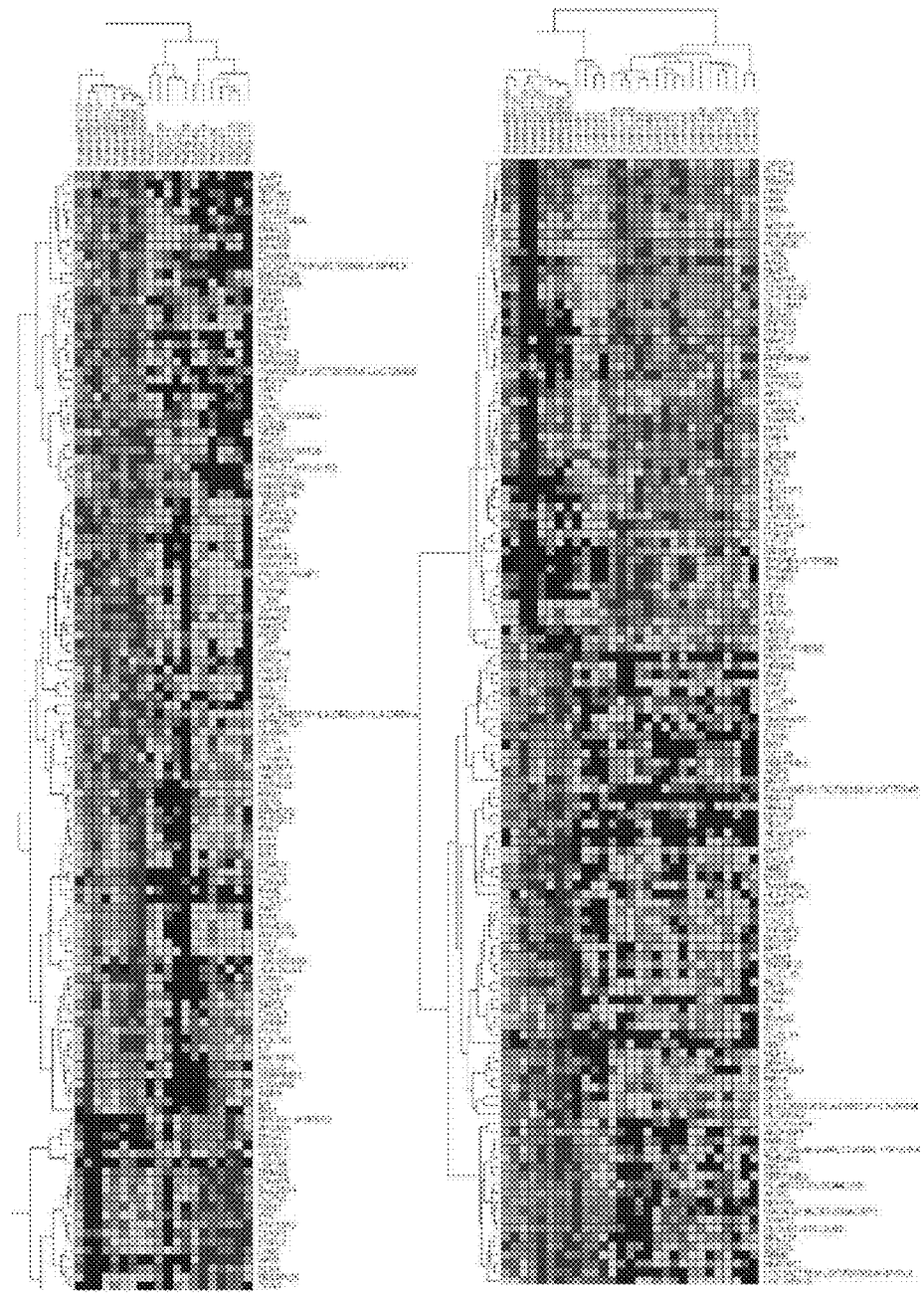
Figure 31   A   B

Figure 32A

| Increased in t-MDS/AML cases | | |
|---|---|---|
| NAME | NES | FDR q-val |
| FALT_BCLL_UP | 2.67254 | <0.001 |
| AGUIRRE_PANCREAS_CHR19 | 2.627985 | <0.001 |
| HIPPOCAMPUS_DEVELOPMENT_POSTNATAL | 2.505901 | <0.001 |
| UVC_TTD_4HR_UP | 2.289109 | 0.002906 |
| INOS_ALL_DN | 2.224038 | 0.002325 |
| NADLER_OBESITY_DN | 2.218849 | 0.001938 |
| LIN_WNT_UP | 2.211983 | 0.001661 |
| TSA_CD4_UP | 2.189324 | 0.00291 |
| HOUSTIS_ROS | 2.175299 | 0.002587 |
| HOFFMANN_BIVSBII_IMVM | 2.114897 | 0.004645 |
| AGUIRRE_PANCREAS_CHR22 | 2.091446 | 0.007365 |
| HSA00480_GLUTATHIONE_METABOLISM | 2.085151 | 0.006752 |
| CROMER_HYPOPHARYNGEAL_MET_VS_NON_DN | 2.074017 | 0.008038 |
| REFRACTORY_GASTRIC_UP | 2.033509 | 0.00999 |
| BCNU_GLIOMA_MGMT_48HRS_DN | 1.988208 | 0.016318 |
| IDX_TSA_UP_CLUSTER4 | 1.975828 | 0.015972 |
| WELCH_GATA1 | 1.959961 | 0.016396 |
| TSA_HEPATOMA_CANCER_UP | 1.958047 | 0.016158 |
| NAKAJIMA_MCSMBP_MAST | 1.943887 | 0.020142 |
| FETAL_LIVER_VS_ADULT_LIVER_GNF2 | 1.94325 | 0.019134 |
| HSA00010_GLYCOLYSIS_AND_GLUCONEOGENESIS | 1.93907 | 0.018768 |
| ADIP_DIFF_CLUSTER1 | 1.922288 | 0.022086 |
| UVC_TTD_ALL_UP | 1.898715 | 0.026589 |
| COLLER_MYC_UP | 1.89825 | 0.025481 |
| GLUTATHIONE_METABOLISM | 1.888796 | 0.027779 |
| HIF1_TARGETS | 1.867534 | 0.032517 |
| H2O2_CSBRESCUED_UP | 1.866796 | 0.031313 |
| GLYCINE_SERINE_AND_THREONINE_METABOLISM | 1.851745 | 0.032673 |
| CALRES_MOUSE_DN | 1.835542 | 0.036003 |
| HSA03020_RNA_POLYMERASE | 1.830047 | 0.037146 |
| CHEN_HOXA5_TARGETS_DN | 1.811887 | 0.042734 |
| PENG_GLUCOSE_UP | 1.802281 | 0.043534 |
| POMEROY_MD_TREATMENT_GOOD_VS_POOR_UP | 1.80157 | 0.042214 |
| BRCA2_BRCA1_UP | 1.800922 | 0.040973 |
| BRCA1_SW480_UP | 1.786563 | 0.043094 |
| BRCA1_OVEREXP_DN | 1.77597 | 0.047058 |
| NING_COPD_DN | 1.773485 | 0.047023 |
| PENG_GLUTAMINE_UP | 1.769385 | 0.047011 |
| HSA00260_GLYCINE_SERINE_AND_THREONINE_METABOLISM | 1.748598 | 0.053486 |

| Increased in normal controls | | |
|---|---|---|
| NAME | NES | FDR q-val |
| CHEN_HOXA5_TARGETS_UP | -2.8369 | <0.001 |
| UVC_XPCS_ALL_DN | -2.6802 | <0.001 |
| UVC_TTD_4HR_DN | -2.6193 | <0.001 |
| UVC_XPCS_8HR_DN | -2.5737 | <0.001 |
| REOVIRUS_HEK293_UP | -2.5579 | <0.001 |
| UVC_TTD_ALL_DN | -2.4108 | <0.001 |
| LINDSTEDT_DEND_UP | -2.3954 | <0.001 |
| POD1_KO_DN | -2.3872 | <0.001 |
| UVB_NHEK1_DN | -2.3256 | <0.001 |
| UVC_XPCS_4HR_DN | -2.3234 | <0.001 |
| BRCA1KO_MEF_DN | -2.3163 | <0.001 |
| UVC_TTD-XPCS_COMMON_DN | -2.2851 | <0.001 |
| GH_GHRHR_KO_24HRS_DN | -2.2501 | <0.001 |
| TAKEDA_NUP8_HOXA9_3D_UP | -2.248 | <0.001 |
| FLECHNER_KIDNEY_TRANSPLANT_WELL_UP | -2.2343 | <0.001 |
| CMV-UV_HCMV_6HRS_UP | -2.2182 | <0.001 |
| SANA_TNFA_ENDOTHELIAL_UP | -2.1525 | 5.58E-04 |
| UVC_HIGH_D4_DN | -2.1467 | 5.27E-04 |
| CMV_HCMV_TIMECOURSE_18HRS_UP | -2.1351 | 5.00E-04 |
| KRETZSCHMAR_IL6_DIFF | -2.12 | 4.75E-04 |
| ET743_SARCOMA_DN | -2.1195 | 4.52E-04 |
| UVC_TTD_8HR_DN | -2.1189 | 4.31E-04 |
| IFNA_HCMV_6HRS_UP | -2.1132 | 4.13E-04 |
| UV-CMV_UNIQUE_HCMV_6HRS_UP | -2.0965 | 3.95E-04 |
| LEE_TCELLS8_UP | -2.0729 | 0.001105 |
| HINATA_NFKB_UP | -2.0702 | 0.001062 |
| HDACI_COLON_SUL48HRS_UP | -2.0521 | 0.001357 |
| OKUMURA_MC_LPS | -2.048 | 0.001635 |
| TAKEDA_NUP8_HOXA9_16D_DN | -2.0459 | 0.001578 |
| UVB_NHEK1_C6 | -2.0289 | 0.001526 |
| UVC_HIGH_ALL_DN | -2.0287 | 0.001477 |
| ET743_SARCOMA_24HRS_DN | -2.0266 | 0.00143 |
| BROCKE_IL6 | -2.0086 | 0.00195 |
| HDACI_COLON_SUL12HRS_DN | -2.0075 | 0.001893 |
| KNUDSEN_PMNS_UP | -2.0048 | 0.001839 |
| ET743_SARCOMA_48HRS_DN | -1.9997 | 0.001788 |
| CTNNB1_ONCOGENIC_SIGNATURE | -1.9958 | 0.00174 |
| LEE_TCELLS1_UP | -1.9929 | 0.001939 |
| DIAB_NEPH_DN | -1.992 | 0.00189 |

| | | | | | |
|---|---|---|---|---|---|
| NING_COPD_UP | 1.724237 | 0.064007 | IFNA_UV-CMV_COMMON_HCMV_6HRS_UP | -1.9901 | 0.002312 |
| OXSTRESS_RPETHREE_DN | 1.718423 | 0.064121 | LEE_TCELLS10_UP | -1.9821 | 0.002479 |
| GLYCOLYSIS_AND_GLUCONEO GENESIS | 1.713628 | 0.063969 | LINDSTEDT_DEND_8H_VS_48H_UP | -1.9783 | 0.00242 |
| GLUCONEOGENESIS | 1.704958 | 0.067246 | HPV31_DN | -1.9672 | 0.003011 |
| INTEGRINPATHWAY | 1.701467 | 0.06755 | TNFA_NFKB_DEP_UP | -1.9559 | 0.003789 |
| HSA00190_OXIDATIVE_PHOSPHORYLATION | 1.699491 | 0.066323 | UVB_SCC_UP | -1.9518 | 0.003705 |
| MITOCHONDRIA | 1.680048 | 0.07637 | UVB_NHEK3_C5 | -1.9445 | 0.004029 |
| GLYCOLYSIS | 1.6793 | 0.074745 | HDACI_COLON_SUL30MIN_DN | -1.9127 | 0.006119 |
| HSA05030_AMYOTROPHIC_LATERAL_SCLEROSIS | 1.668317 | 0.080521 | HDACI_COLON_CURSUL_UP | -1.9014 | 0.008135 |
| FRUCTOSE_AND_MANNOSE_METABOLISM | 1.662614 | 0.081479 | BAF57_BT549_DN | -1.9004 | 0.007969 |

| Increased in NHL/HL controls | | |
|---|---|---|
| NAME | NES | FDR q-val |
| LIN_WNT_UP | 2.302547 | <0.001 |
| AGUIRRE_PANCREAS_CHR19 | 2.294415 | <0.001 |
| ELECTRON_TRANSPORT_CHAIN | 2.284217 | <0.001 |
| BRCA1_OVEREXP_DN | 2.181481 | 0.002073 |
| HSA00190_OXIDATIVE_PHOSPHORYLATION | 2.158962 | 0.001658 |
| FERRANDO_MLL_T_ALL_DN | 2.12586 | 0.004249 |
| FALT_BCLL_UP | 2.122335 | 0.003642 |
| MITOCHONDRIA | 2.104803 | 0.003187 |
| HUMAN_MITODB_6_2002 | 2.077627 | 0.002833 |
| PYRIMIDINE_METABOLISM | 2.057725 | 0.00255 |
| POD1_KO_UP | 2.050436 | 0.002318 |
| FETAL_LIVER_VS_ADULT_LIVER_GNF2 | 2.036642 | 0.002846 |
| HIPPOCAMPUS_DEVELOPMENT_POSTNATAL | 2.028083 | 0.002627 |
| BCNU_GLIOMA_MGMT_48HRS_DN | 2.026996 | 0.00244 |
| CROONQUIST_IL6_STARVE_UP | 2.002321 | 0.005125 |
| OXIDATIVE_PHOSPHORYLATION | 1.982475 | 0.004805 |
| CROONQUIST_IL6_RAS_DN | 1.979253 | 0.004522 |
| HOFFMANN_BIVSBII_IMVM | 1.959819 | 0.005208 |
| TSA_CD4_UP | 1.955163 | 0.005831 |
| WALLACE_JAK2_DIFF | 1.951632 | 0.00596 |
| PGC | 1.942392 | 0.005676 |
| GLUTATHIONE_METABOLISM | 1.9406 | 0.005806 |
| MOOTHA_VOXPHOS | 1.936779 | 0.005553 |
| HSA00260_GLYCINE_SERINE_AND_THREONINE_METABOLISM | 1.931046 | 0.005322 |
| POMEROY_MD_TREATMENT_GOOD_VS_POOR_DN | 1.927975 | 0.005445 |
| CANTHARIDIN_DN | 1.926101 | 0.005563 |
| PEART_HISTONE_DN | 1.921451 | 0.006618 |
| BRCA2_BRCA1_UP | 1.917284 | 0.006381 |
| HSA00240_PYRIMIDINE_METABOLISM | 1.893594 | 0.00967 |
| GLYCOLYSIS_AND_GLUCONEOGENESIS | 1.874226 | 0.011909 |
| HSA00970_AMINOACYL_TRNA_BIOSYNTHESIS | 1.870682 | 0.011525 |
| PENG_GLUTAMINE_UP | 1.866615 | 0.011436 |
| PURINE_METABOLISM | 1.84735 | 0.015984 |
| REFRACTORY_GASTRIC_UP | 1.839761 | 0.016274 |
| ROS_MOUSE_AORTA_UP | 1.837754 | 0.016295 |
| UVC_TTD_4HR_UP | 1.814932 | 0.020348 |
| AGUIRRE_PANCREAS_CHR7 | 1.807379 | 0.022308 |
| AGUIRRE_PANCREAS_CHR22 | 1.794659 | 0.024612 |
| CELL_CYCLE | 1.794183 | 0.024205 |
| HSA00230_PURINE_METABOLISM | 1.787922 | 0.025295 |

| Increased in normal CD34+ cells | | |
|---|---|---|
| NAME | NES | FDR q-val |
| CHEN_HOXA5_TARGETS_UP | -3.3944 | <0.001 |
| UVC_TTD_4HR_DN | -2.87305 | <0.001 |
| UVC_TTD_ALL_DN | -2.7998 | <0.001 |
| UVC_XPCS_8HR_DN | -2.7285 | <0.001 |
| POD1_KO_DN | -2.71418 | <0.001 |
| TAKEDA_NUP8_HOXA9_6H_UP | -2.70656 | <0.001 |
| UVC_XPCS_ALL_DN | -2.6922 | <0.001 |
| CMV-UV_HCMV_6HRS_UP | -2.681 | <0.001 |
| REOVIRUS_HEK293_UP | -2.64891 | <0.001 |
| UVC_XPCS_4HR_DN | -2.51413 | <0.001 |
| DAC_BLADDER_UP | -2.46097 | <0.001 |
| UVB_NHEK1_DN | -2.41141 | <0.001 |
| CTNNB1_ONCOGENIC_SIGNATURE | -2.39924 | <0.001 |
| UVC_HIGH_D4_DN | -2.39593 | <0.001 |
| BRCA1KO_MEF_DN | -2.38409 | <0.001 |
| UVC_TTD-XPCS_COMMON_DN | -2.38 | <0.001 |
| SANA_TNFA_ENDOTHELIAL_UP | -2.37772 | <0.001 |
| BROCKE_IL6 | -2.34405 | <0.001 |
| CMV_HCMV_TIMECOURSE_12HRS_UP | -2.31415 | <0.001 |
| KNUDSEN_PMNS_UP | -2.30693 | <0.001 |
| IDX_TSA_UP_CLUSTER1 | -2.30288 | <0.001 |
| LINDSTEDT_DEND_8H_VS_48H_UP | -2.30186 | <0.001 |
| TAKEDA_NUP8_HOXA9_3D_UP | -2.28963 | <0.001 |
| UV-CMV_UNIQUE_HCMV_6HRS_UP | -2.26225 | <0.001 |
| HDACI_COLON_CURSUL_UP | -2.24929 | <0.001 |
| KRETZSCHMAR_IL6_DIFF | -2.22682 | <0.001 |
| UVC_TTD_8HR_DN | -2.18113 | 0.001055 |
| HDACI_COLON_CUR12HRS_UP | -2.15998 | 0.001549 |
| LINDSTEDT_DEND_UP | -2.15138 | 0.001496 |
| PASSERINI_INFLAMMATION | -2.14016 | 0.001446 |
| BAF57_BT549_UP | -2.12411 | 0.001872 |
| TAKEDA_NUP8_HOXA9_8D_DN | -2.11168 | 0.001813 |
| CMV_HCMV_TIMECOURSE_48HRS_UP | -2.08381 | 0.002184 |
| HDACI_COLON_SUL48HRS_UP | -2.07497 | 0.002119 |
| CMV_HCMV_6HRS_UP | -2.06257 | 0.002897 |
| STOSSI_ER_UP | -2.04555 | 0.003214 |
| LEE_TCELLS1_UP | -2.03918 | 0.003127 |
| TNFA_NFKB_DEP_UP | -2.02546 | 0.003408 |
| CMV_HCMV_TIMECOURSE_18HRS_UP | -2.00743 | 0.004082 |
| LVAD_HEARTFAILURE_DN | -1.99848 | 0.004345 |

| | | | | | |
|---|---|---|---|---|---|
| UVB_NHEK3_C7 | 1.786022 | 0.025083 | CHIARETTI_T_ALL_DIFF | -1.99626 | 0.004239 |
| H2O2_CSBRESCUED_UP | 1.785192 | 0.024486 | CMV_HCMV_TIMECOURSE_ALL_UP | -1.99141 | 0.004483 |
| ADIP_VS_FIBRO_UP | 1.783435 | 0.02431 | HEMATOP_STEM_ALL_UP | -1.99098 | 0.004378 |
| SHEPARD_BMYB_MORPHOLINO_DN | 1.781421 | 0.024343 | LEE_TCELLS8_UP | -1.98996 | 0.004904 |
| MANALO_HYPOXIA_DN | 1.77984 | 0.024369 | SRC_ONCOGENIC_SIGNATURE | -1.98057 | 0.005445 |
| HSA00480_GLUTATHIONE_METABOLISM | 1.779352 | 0.02402 | CHIARETTI_T_ALL | -1.96994 | 0.005643 |
| HSA00350_TYROSINE_METABOLISM | 1.779279 | 0.023509 | LEE_TCELLS10_UP | -1.96906 | 0.005523 |
| DOX_RESIST_GASTRIC_UP | 1.770959 | 0.025492 | RAS_ONCOGENIC_SIGNATURE | -1.96649 | 0.00573 |
| DNA_REPLICATION_REACTOME | 1.764797 | 0.026711 | TAKEDA_NUP8_HOXA9_16D_DN | -1.95371 | 0.006171 |

Figure 32B cont'd

Figure 35
A
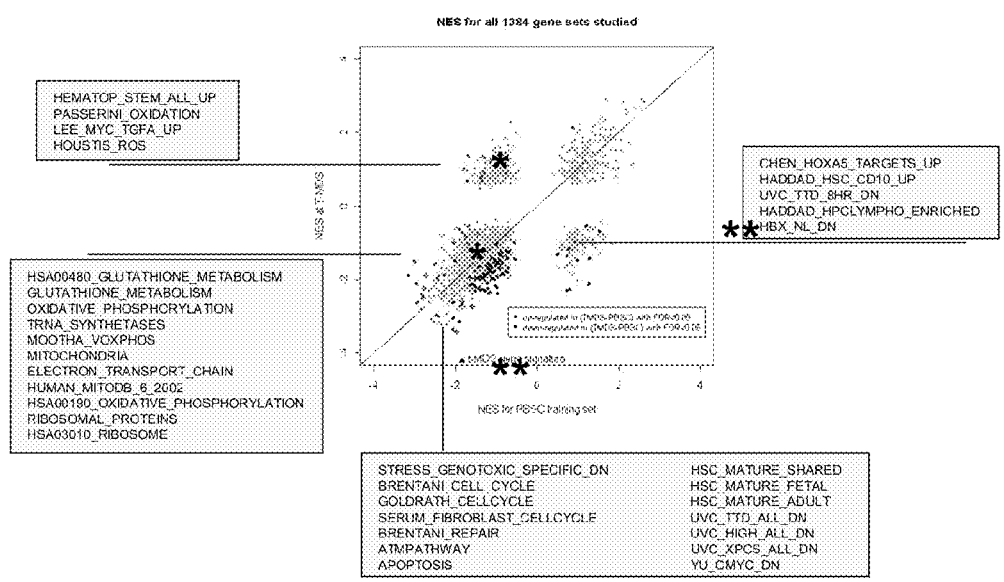
B
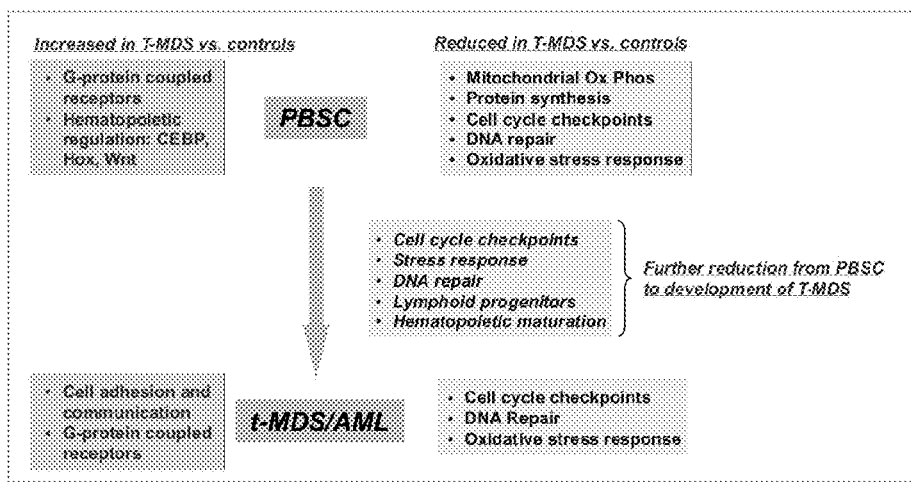

The table content is largely illegible due to image quality.

* Abbreviations: M=male; F=Female; W=white; H=Hispanic; B=black

Figure 37B

|  | Training set | Test Set | p-value |
|---|---|---|---|
|  | t-MDS/AML cases (n=18) | t-MDS cases (n=16) |  |
| Primary diagnosis |  |  | 0.002 |
| HL | 1(5.5%) | 9 (56%) |  |
| NHL | 17 (94.5%) | 7 (44%) |  |
| Mean age at diagnosis | 48 | 46.5 | 0.72 |
| Race/ ethnicity |  |  | 0.73 |
| Caucasians | 10 (55.6%) | 11 (69%) |  |
| Hispanics | 7 (38.9%) | 4 (25%) |  |
| African-Americans | 1 (5.5%) | 1 (6%) |  |
| Asians/Other | 0 |  |  |
| Mean age at HCT | 49.4 | 49.8 | 0.94 |
| Stem cell source |  |  | 1 |
| Peripheral stem cells | 17 (94%) | 15(94%) |  |
| Bone marrow+PBSC | 1 (6%) | 1 (6%) |  |
| Tandem HCTs | 1 (6%) | 1 (6%) | 1 |
| Number of stem cell collections |  |  |  |
| Mean (SD) | 7.1 (4.6) | 7.2 (4.3) | 0.96 |
| Median (range) | 6.0 (1-17) | 6.5 (2-17) |  |
| Stem cell mobilization (yes) |  |  |  |
| G-CSF | 18 (100%) | 16 (100%) | - |
| Etoposide | 2 (11%) | 3 (19%) | 0.65 |
| Cyclophosphamide | 7(39%) | 3 (19%) | 0.27 |
| Other (taxol) | 2 (11%) | 0 | 0.49 |
| Stem cell dose infused |  |  |  |
| Mean (SD) | 5.0 (3.7) | 5.2 (3.7) | 0.86 |
| Median (range) | 3.5 (0.9-16.2) | 4.2 (1.9-16.1) |  |
| HCT conditioning |  |  |  |
| Cyclophosphamide |  |  |  |
| Yes | 16 (89%) | 14 (88%) | 1 |
| Mean (SD) | 3818 (892) | 4314 (437) | 0.07 |
| Etoposide |  |  |  |
| Yes | 18 (100%) | 15 (94%) | 0.47 |
| Mean (SD) | 2333 (750) | 2469 (526) | 0.56 |
| Total body irradiation |  |  |  |
| Yes | 11 (61%) | 8 (50%) | 0.73 |
| Mean | 1200 | 1230 | 0.09 |
| Therapeutic exposures |  |  |  |
| Radiation (Yes) | 15(83%) | 13(81%) | 1 |
| Alkylating agent score |  |  | 0.02 |
| 1,2 | 11 (61%) | 3 (19%) |  |
| 3, 4, 5 | 7 (39%) | 13 (81%) |  |
| Topoisomerase II inhibitor score |  |  |  |
| 2 |  |  | 1 |
| 3, 4 | 5 (28%) | 4 (25%) |  |
|  | 13 (72%) | 12 (75%) |  |

Figure 40A    Training Set

| Number | Pre cytogenetics | t-MDS cytogenetics* |
|---|---|---|
| Training set | | |
| 8 | 46,XY[18 of 20 cells]<br><br>Nonclonal Aberrations:<br>46,XY,del(3)(q21q29),add(11)(p15),-17,-18,add(22)(q13),+mar[1]<br><br>Nonclonal Aberrations: 46,XY,t(5;13)(p10;q10)[1]<br><br>No FISH | 46,XY [20 of 20 cells]<br><br>No FISH |
| 11 | 46,XY [21 of 21 cells] | |
| 24 | 46,XY [20 of 20 cells] | |
| 25 | 46,XY [20 of 20 cells] | |
| 61* | 46,XX | |
| 62* | 46, XY | |
| 101 | 1908<br>Nonclonal Aberration: 47,XX,+mar [1] | |
| 111 | 46,XX [20 of 20 cells] | |
| 120 | 46,XX [20 of 20 cells] | |
| 125* | 46,XX [20 of 20 cells] | |
| 137 | 46,XX [20 of 20 cells] | |
| 155 | 46,XY [19 of 20 cells].<br><br>Nonclonal aberration: 46,XY,del(8)(q13q22)[1]<br><br>No FISH | 46,XY [19 of 20 cells]<br><br>Nonclonal aberration:<br>46,XY,del(8)(q13q22)[1]<br><br>Nonclonal Aberration:<br>46,XY,ins(17;7)(p13;q22q32) [1] No FISH |
| 168* | 46,XX [20 of 20 cells] | |
| 231 | 46,XX | |
| 5005 | 46,XY[20 of 20 cells] | |
| 5036* | 46,XX [14 of 20 cells], Nonclonal Aberrations:46,XX,del(18)(q21q23) [1]Nonclonal Aberrations:46,XX,t(16;18)(q22;q21) [1]Nonclonal Aberrations:46,XX,t(3;18)(p25;q11.2) [1]Nonclonal Aberrations:46,X,t(X;7)(p10;q10),t(4;20)(p16;q11.2) [1]Nonclonal Aberrations:46,XX,del(6)(p21.3p23) [1]Nonclonal Aberrations:46,XX,t(9;18)(q22;q23) [1]<br><br>No FISH | 46,XX [20 of 20 cells]<br><br><br><br><br><br><br><br>FISH: nuc ish 8cen(D8Z2x1) (1 of 200 cells) |
| 5040 | 46,XX [21 of 21 cells] | |
| 5042 | 46,XY[20 of 20 cells] | |

Figure 40A (continued)    Test Set

| Test set | | |
|---|---|---|
| 5008 | 46,XX,inv(9)(p13q13) [20 of 20 cells]<br><br>No FISH | Stemline: 45,XX,-7,inv(9)(p13q13)c [20 of 20 cells]<br><br>FISH: nuc ish 7cen(D7Z1x2) (8 of 200 cells) |
| 5035 | 46,XX [20 of 20 cells] | Constitutional Cell Line: 46,XX [2 of 20 cells]<br>Stemline:<br>44,XX,der(1)t(1;2)(p36.3;q11.2),t(1;11)(p34.1;p15),-2,-3,der(5;18)(p10;q10),add(10)(q26),<br><br>t(12;15)(q13;q15),inv(?13)(q12q22),-21,+mar1,+mar2 [2 of 20 cells]<br><br>Sideline: 46,idem,+3,del(6)(p21.3p23),+19 [16 of 20 cells] |
| 5099 | Unknown | |
| 15001 | 46,XY [20 of 20 cells] | |
| 15002 | 46,XY [17] (AN), 45,X,-Y [3]<br><br>FISH: nuc ish 11q13(CCND1x2),14q32(IGHx2) (200 of 200 cells) | 45,X,-Y,t(10;11)(p13;q13) [3]<br><br>46,XY [16]<br><br><br>46, partial deletion of the long arm of one chromosome 7<br><br>No FISH |
| 15004 | 46,XY | |
| 15005 | Unknown | |
| 15006 | Unknown | |
| 15007 | Unknown | |
| 15008 | 46,XX [8 of 8 cells] | |
| 15009 | Unknown | |
| 15011 | 46,XY [6 of 6 cells] | |
| 211 | 46,XY [20 of 20 cells] | |
| 650 | 46, XY | |
| 5069 | 46,XY[19 of 20 cells],<br>46,XY,del(15)(q15q26)[1]<br><br>No FISH | Stemline: 47,XY,+8 [3 of 30 cells]<br><br>Constitutional Cell Line: 46,XY [26 of 30 cells]<br>Nonclonal Aberration: 47,XY,+Y [1]<br>No FISH |
| 15003 | 46,XY [22 of 22 cells] | |

Figure 40B

| Number | Abnormality at time of t-MDS/AML | PBSC CD34+ cell analysis |
|---|---|---|
| 61 | 46,XX,del(20)(q11.2q13.1)[6 of 30 cells] | Chromosome 20 FISH [Vysis LSI D20S108 (20q12)]: 0/92 cells with 20q deletion; Background: 2% |
| 101 | 46,XX,t(7;11)(p13;q23)[20 of 20 cells] | MLL FISH [Vysis LSI MLL (11q23) probe]: 0/193 cells with aberrant FISH signals consistent with MLL rearrangement; Background: 3%. |
| 137 | 46,XX,t(9;11)(p22;q23),add(19)(p13.3)[30 of 30 cells] | MLL FISH [Vysis LSI MLL (11q23) probe] performed on mitotic cells. Whole chromosome painting 0/42 abnormal mitoses |
| 650 | 45,XY,-5,add(17)(p11.2),-18,+mar[6/24 mitosis] | |
| 15004 | 43~45,XY,-3,-5, der(3)t(3;6)(q21;p21.3), add(13)(p11.2), del(13)(q14q33), add(14)(q32), add(15)(p11.2), 18,del(20)(q11.2q13.1), -21, +1-2r[cp11]/46,XY[9] | Chromosome 20 FISH [Vysis LSI D20S108 (20q12)]: 0/200 cells with 20q deletion; Background: 2% Whole chromosome painting: 0/20 abnormal mitoses |
| 15006 | 43~44,XY,del(3)(q25q27),-5,add(6)(q23),-7, der(11) t(7;11)(p15;q23)[cp20] | MLL FISH [Vysis LSI MLL (11q23) probe]: 0/200 cells with aberrant FISH signals consistent with MLL rearrangement; Background: 3% Whole chromosome painting: 0/12 abnormal mitoses |
| 15007 | 44,XY,-1, der(1;6)(q10;q10), der(4;add(4)(p16), -5, der(7);add(7)(p22), del(9)(q22), del(11)(3;11)(q21;p15),-15, t(17)(q10), +mar, inc[3] 43~44,idem,del(5)(q31q35),-13, del(13)(q12q14), der(15)t(15;17)(q22;q12), der(7)t(5;17)(q22;q12)?t(17;?)(p11.2;?),- t(17)(q21)q31,-11,?add(13)(q10),-17,-18, +del(20)(q11.2q13.3),+mar1 [7] 44~45,idem,-r(?3),add(18)(q21),+mar2 [cp3] 46~47,idem,+del(20)(q11.2q13.3) [cp2] | |
| 15008 | 46,XX,t(1;4)(p3?4;q3,r(?3)(p25q29)x2,der(5)t(5;17)(q3 ?1;q21),-11,?add(13)(q10),-17,-18, +del(20)(q11.2q13.3),+mar1 [7] | Chromosome 20 FISH [Vysis LSI D20S108 (20q12)]: 0/189 cells with 20q deletion; Background: 2% |

Figure 42
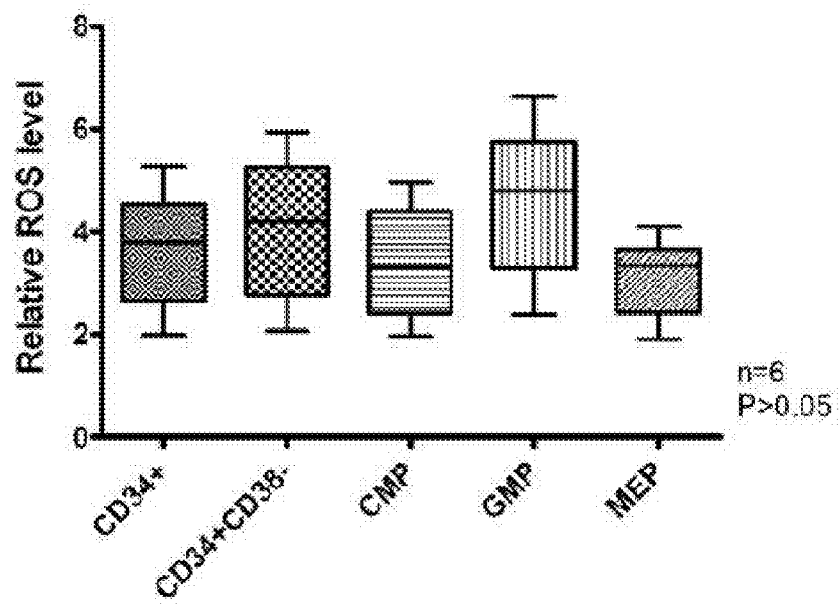
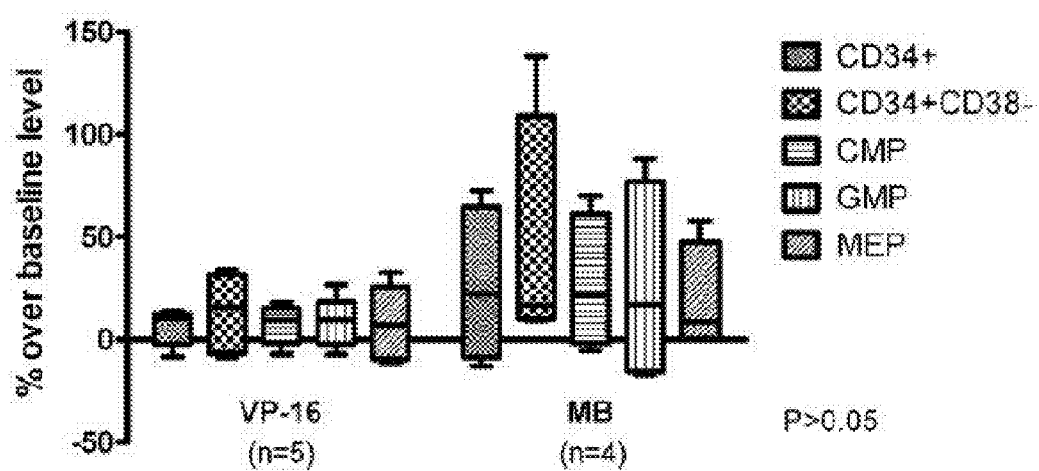

US 9,347,102 B2

GENE SIGNATURES FOR PREDICTION OF THERAPY-RELATED MYELODYSPLASIA AND METHODS FOR IDENTIFICATION OF PATIENTS AT RISK FOR DEVELOPMENT OF THE SAME

PRIORITY CLAIM

This application is a continuation of International Application No. PCT/US2011/064040, filed Dec. 8, 2011, which claims the benefit of U.S. Provisional Patent Application No. 61/421,200, filed Dec. 8, 2010, both of which are incorporated by reference herein in their entireties.

STATEMENT OF GOVERNMENT INTEREST

The present invention was made with government support under Grant No. R01-HL083050 and Grant No. P50 CA107399, awarded by the National Institutes of Health (NIH). The Government has certain rights in the invention.

BACKGROUND

Therapy-related myelodysplasia or acute myeloid leukemia (t-MDS/AML) is often a lethal complication of conventional genotoxic or cytotoxic cancer therapy. t-MDS/AML accounts for 15% of all AML and MDS cases and shares morphologic and cytogenetic characteristics with primary MDS and AML in the elderly. Lymphoma patients receiving conventional therapy are at an increased risk of developing t-MDS/AML, and this risk is considerably higher among patients receiving high-dose therapy with stem cell rescue. In particular, t-MDS/AML is a leading cause of non-relapse mortality following autologous hematopoietic cell transplantation (aHCT) for Hodgkin lymphoma (HL) or non-Hodgkin lymphoma (NHL) (Bhatia et al. 1996, Miller et al. 1994; Pedersen-Bjergaard et al. 2000; Stone et al. 1994). The overwhelming majority of patients develop t-MDS/AML within 6 years after aHCT, and it has been shown that the cumulative probability of developing t-MDS/AML is about 8.6% within that time (FIG. 1).

In addition to exposure to conventional cancer therapies (e.g., chemotherapy and radiation therapy), it is thought that transplant conditioning, autograft collection and hematopoietic regeneration prior to aHCT also contribute to the development of t-MDS/AML (Bhatia et al. 1996; Kalaycio et al. 2006; Krishnan et al. 2000). However, its pathogenesis is not well understood and methods for predicting the risk of developing t-MDS/AML in individual cancer survivors are not available.

The study of t-MDS/AML provides an opportunity to understand leukemogenesis since genotoxic or cytotoxic exposures can be temporally and causally related to genetic changes associated with subsequent development of leukemia (Smith et al. 2003; Pedersen-Bjergaard 2005). Therefore, it is desired to identify changes in gene expression related to genetic changes that have an impact on the development of t-MDS/AML.

SUMMARY

In one embodiment, a gene expression signature for predicting risk of developing therapy-related myelodysplasia or acute myeloid leukemia (t-MDS/AML) after autologous hematopoietic cell transplantation (aHCT) is provided. The gene expression signature includes a set of two or more genes associated with the development of t-MDS/AML and are expressed in CD34+ cells.

In another embodiment, a method for predicting a risk for development of therapy-related myelodysplasia or acute myeloid leukemia (t-MDS/AML) after autologous hematopoietic cell transplantation (aHCT) is provided. Such a method may include detecting a test expression level of a set of two or more genes of a gene expression signature in a biological sample from a subject; comparing the test expression level of a set of corresponding training expression levels that include a training case expression level and a training control expression level; and predicting a high risk of developing t-MDS/AML when the test expression level is at or about the training case expression level or predicting a low risk of developing t-MDS/AML when the test expression level is at or about the training control expression level.

In another embodiment, a kit to predict a subject's risk of developing t-MDS/AML is provided. The kit may include a set of detection agents capable of detecting a test expression level of a set of two or more genes of a CD34+ cell gene expression signature.

According to the embodiments described herein, the gene expression signature having two or more genes associated with the development of t-MDS/AML are selected from genes related to mitochondrial oxidative phosphorylation, protein synthesis, cell cycle, DNA repair, cellular response to injury, G-protein coupled receptors, hematopoietic regulation, cell adhesion, cell communication, immediate-early stress response, xenobiotic processing, hematopoietic stem cell growth and regulation. In one embodiment, the two or more genes are selected from the group consisting of NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2.

In another embodiment, the gene expression signature is a set of 38 genes. In one embodiment, the set of 38 genes are NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2.

Red dots represent those gene sets upregulated during the development of t-MDS/AML, blue dots represent those gene sets downregulated during the development of t-MDS/AML and black dots represent those gene sets that showed similar temporal changes over the time course between cases and controls. This figure shows that many gene sets were upregulated or downregulated in CD34+ cells from both PBSC and bone marrow at the time of t-MDS/AML. This indicates that abnormalities in gene expression associated with t-MDS were present in PBSC long before the development of disease.

Figure 4:
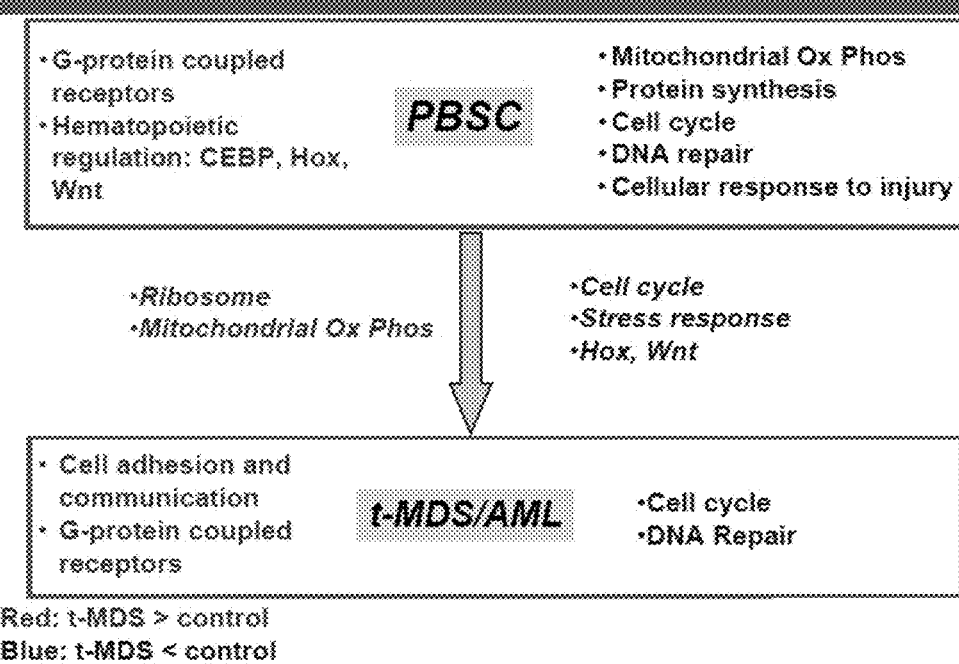

FIG. 4 is a chart summarizing the results of the gene expression analysis, showing gene sets that are associated with the development of t-MDS/AML from pre-HCT samples and those obtained at the time of t-MDS/AML development. CD34+ cells from PBSC obtained from patients who subsequently developed t-MDS were characterized by a) downregulation of genes related to Mitochondrial oxidative phosphorylation, protein synthesis, cell cycle, DNA repair and cellular response to injury; and b) upregulation of genes related to GPCR and certain hematopoietic transcription factors. Gene sets related to cell cycle regulation and DNA repair were prominently downregulated in cases at the time of t-MDS, whereas gene sets related to cell adhesion and cell communication as well as GPCR remained upregulated. Cell cycle regulatory gene were reduced n PBSC but were further downregulated in the course of development of t-MDS, Mitochondrial oxidative phosphorylation and ribosomal genes which were markedly downregulated in PBSC from cases were relatively upregulated in the course of development of t-MDS.

Figure 5:
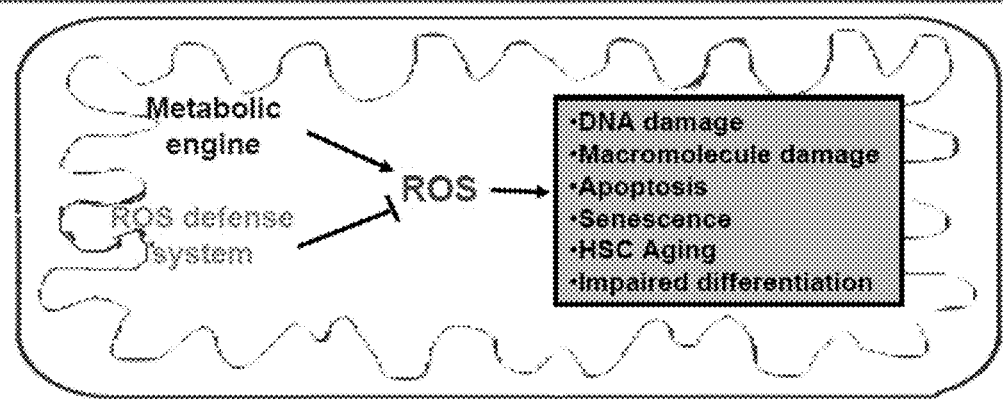

FIG. 5 is a schematic drawing illustrating that mitochondrial oxidative phosphorylation may result in enhanced ROS generation in CD34+ cells from patients who subsequently develop t-MDS/AML. In addition, reduced ROS detoxification may be associated with increased ROS levels at baseline and after exposure to oxidative stress. Enhanced ROS production in the setting to therapeutic exposures (e.g., chemotherapy and radiation therapy) may result in enhanced DNA damage and impaired cellular function in hematopoietic stem cells from patients predisposed to t-MDS.

FIG. 6 is a table listing a 38-gene signature associated with the development of t-MDS/AML according to one embodiment.

Figure 7:
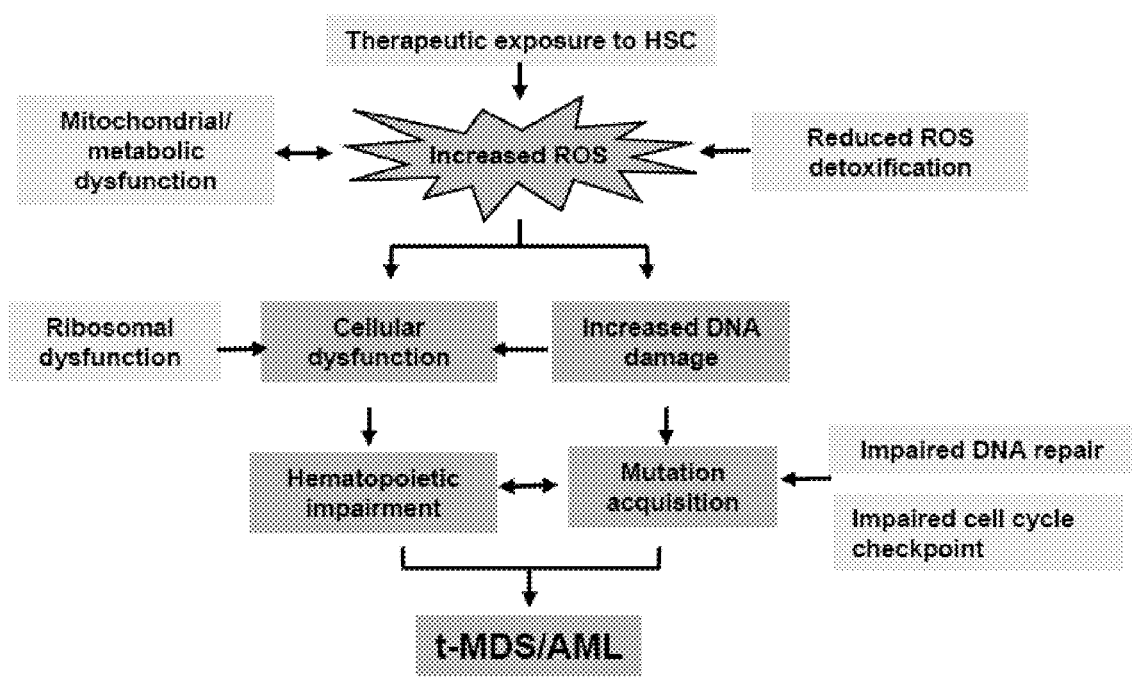

FIG. 7. Proposed model for pathogenesis of t-MDS/AML. Therapeutic exposure to HSC results in elevated ROS levels related to mitochondrial dysfunction. Excessive ROS generation results in increased DNA damage, cellular dysfunction and impaired hematopoiesis. Impaired DNA repair and cell cycle regulation leads to accumulation of mutations which potentially contributes to the development of t-MDS/AML.

Figure 8:
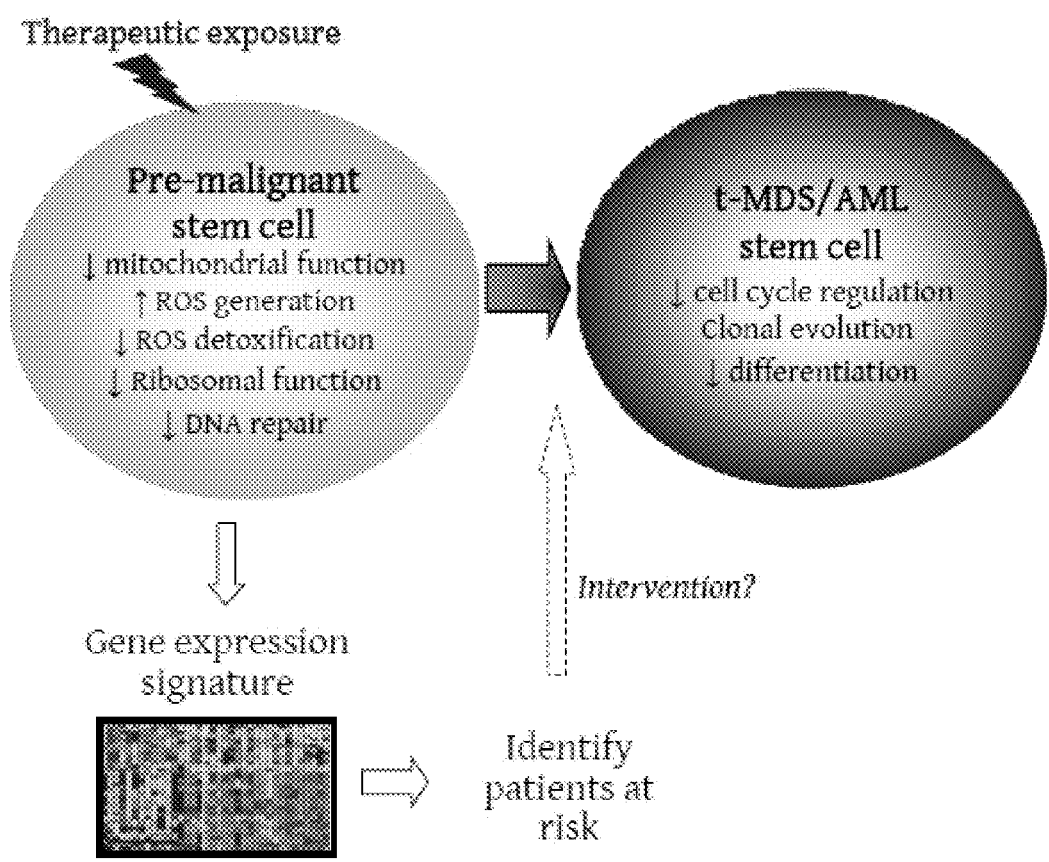

FIG. 8 is a schematic representation of a pre-malignant stem cell's response to therapeutic exposure to radiation or other DNA damaging therapeutics. This response results in differential gene expression, which is analyzed to generate a gene expression signature that can identify patients at risk for t-MDS/AML. Once patient has been identified as being at risk, an intervention may be determined.

Figure 9:
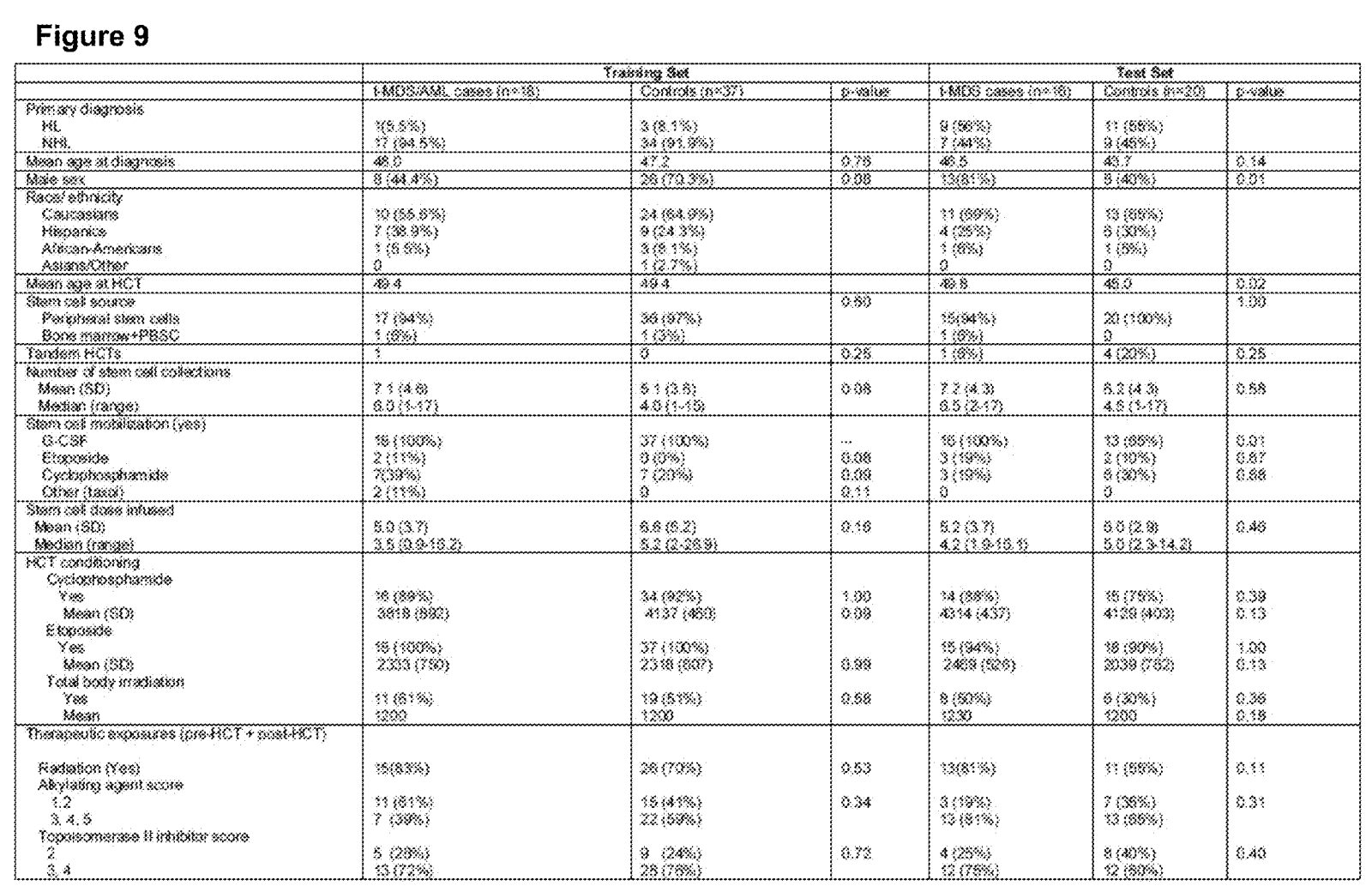

FIG. 9 is a table showing the demographic and clinical characteristics of the training set and the test set.

Figure 10:
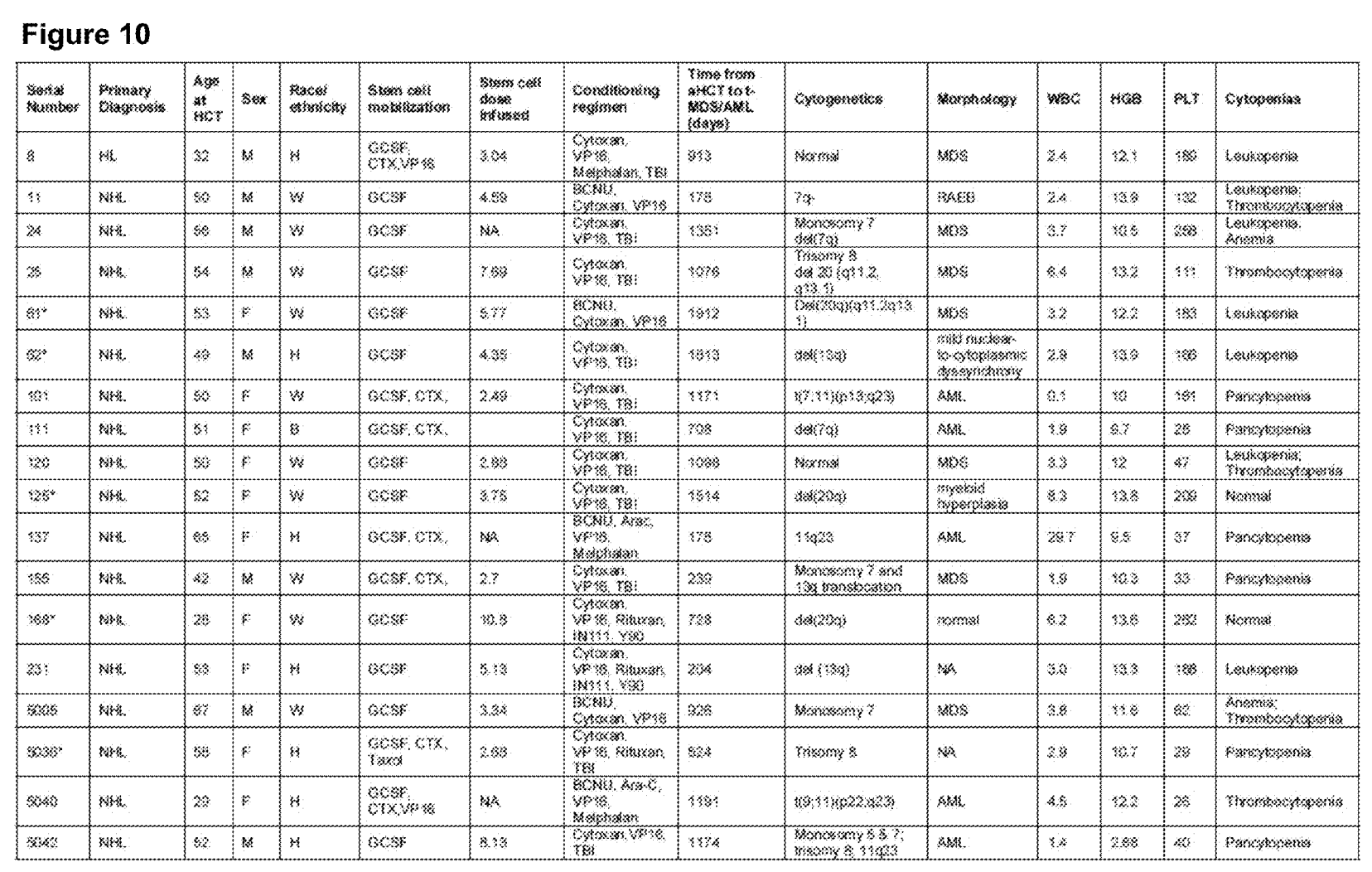

FIG. 10 is a table summarizing the clinical characteristics of t-MDS/AML after autologous HCT for Lymphoma for the training set.

FIG. 11 is a table summarizing the clinical characteristics of t-MDS/AML after autologous HCT for Lymphoma for the test set.

Figure 12:
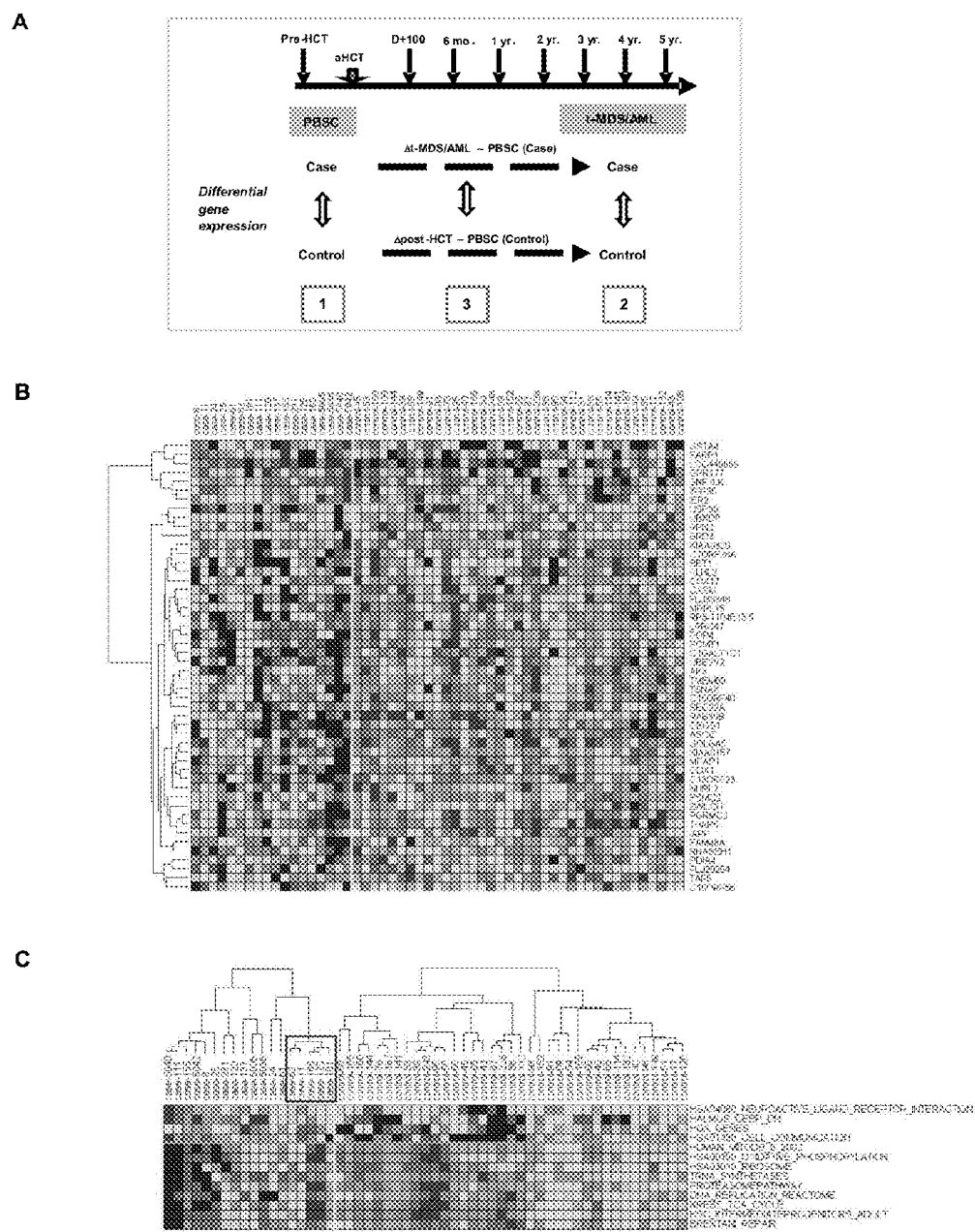

FIG. 12 illustrates altered gene expression in PBSC CD34+ cells from t-MDS/AML cases compared with controls. (A) The study design is shown. Gene expression was compared between [1] pre-aHCT PBSC samples obtained from cases (n=18) versus controls (n=37); [2] BM samples obtained from cases at time of t-MDS/AML (n=12) versus BM samples obtained from controls at comparable time points post-aHCT (n=21); and [3] changes in gene expression over time from PBSC collection to development of t-MDS/AML in cases compared with gene expression changes over a comparable time period in controls (Δ t-MDS/AML-PBSC). (B) Differences in gene expression in PBSC CD34+ cells from cases and controls are shown for top 50 genes with the smallest P-values and 4-fold change in OR (OR>4 or OR<0.25). (C) Expression of representative gene sets within individual PBSC CD34+ cells from individual cases and controls is shown. The expression was averaged over the genes in each gene set and hierarchical clustering was performed for samples within the case and control groups. The box indicates the five cases with gene expression resembling that of controls. See also FIGS. 9, 10, 12, 13, 20, and 21.

Figure 1:
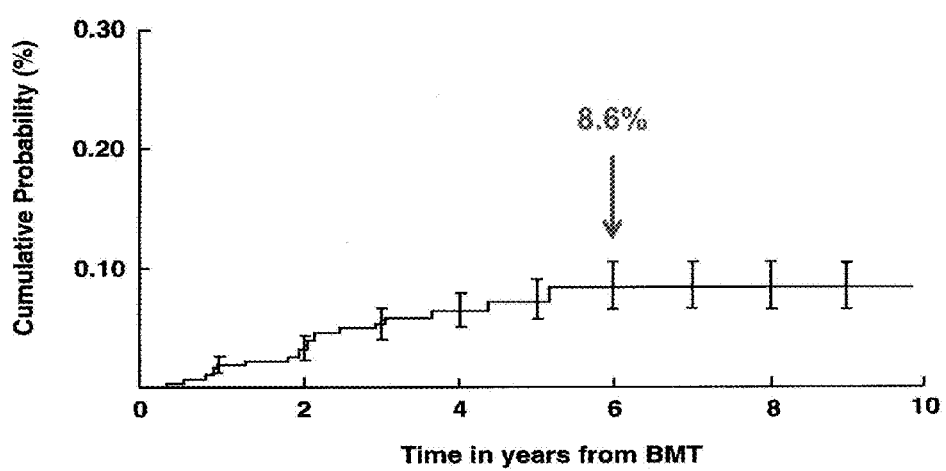
FIG. 1 shows the cumulative probability of developing t-MDS/AML after high dose cancer therapy and autologous hematopoietic cell transplantation (aHCT).
Figure 13:
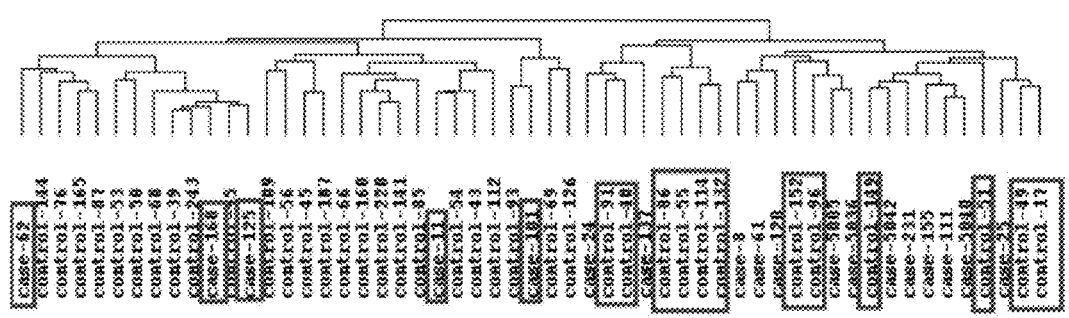

FIG. 13, which is related to FIG. 1 illustrates hierarchical clustering for PBSC samples with all genes after filtering. Samples clustered into two large groups. In one cluster 5 cases clustered with 25 controls. In the other cluster 12 cases clustered with 11 controls.

FIG. 14 is a table summarizing gene sets that were enriched in PBSC CD34+ cells from patients who later developed t-MDS/AML.

Figure 15:
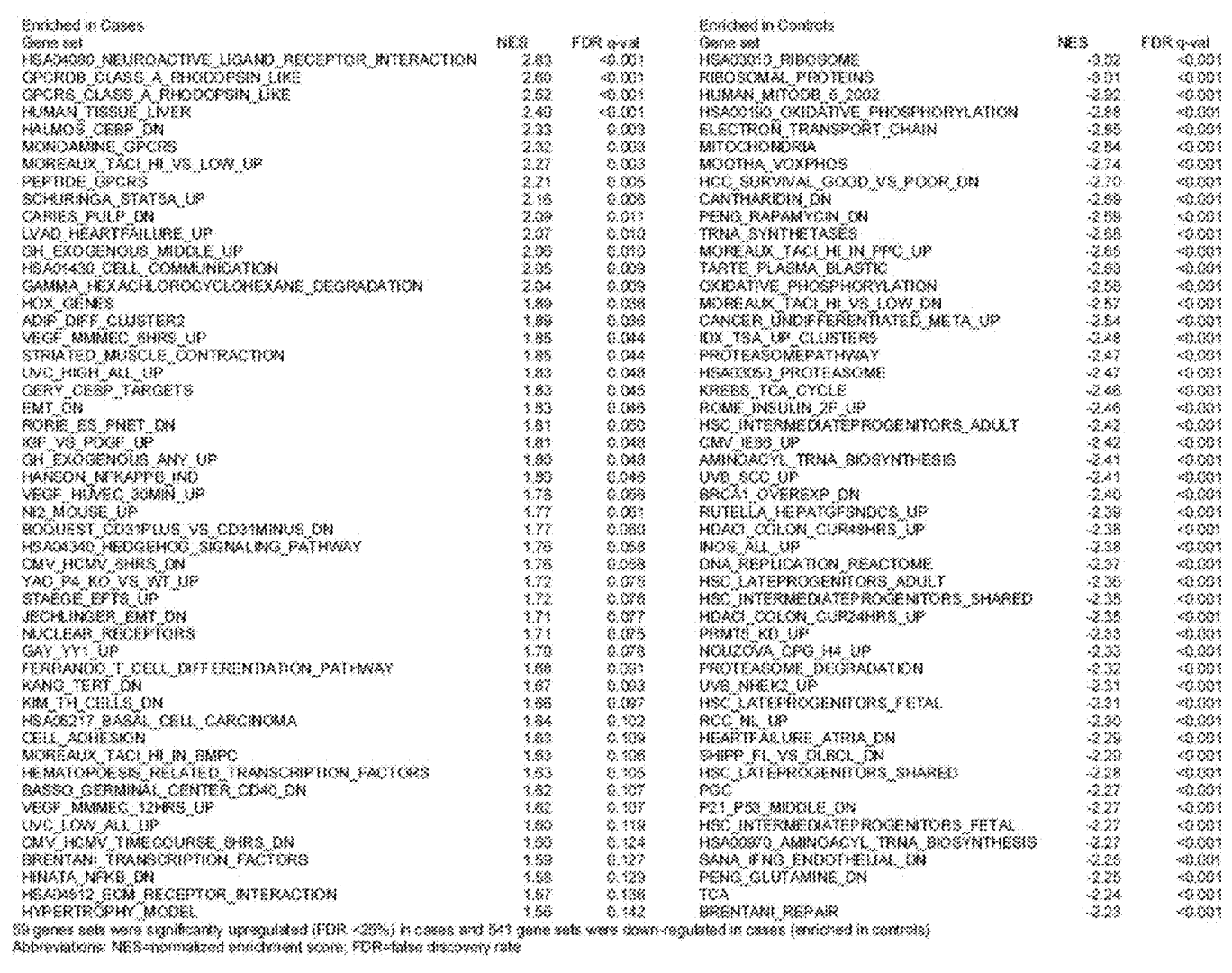

FIG. 15 is a table summarizing the gene sets that were enriched in PBSC CD34+ cells from t-MDS/AML cases in the training set.

Figure 16:
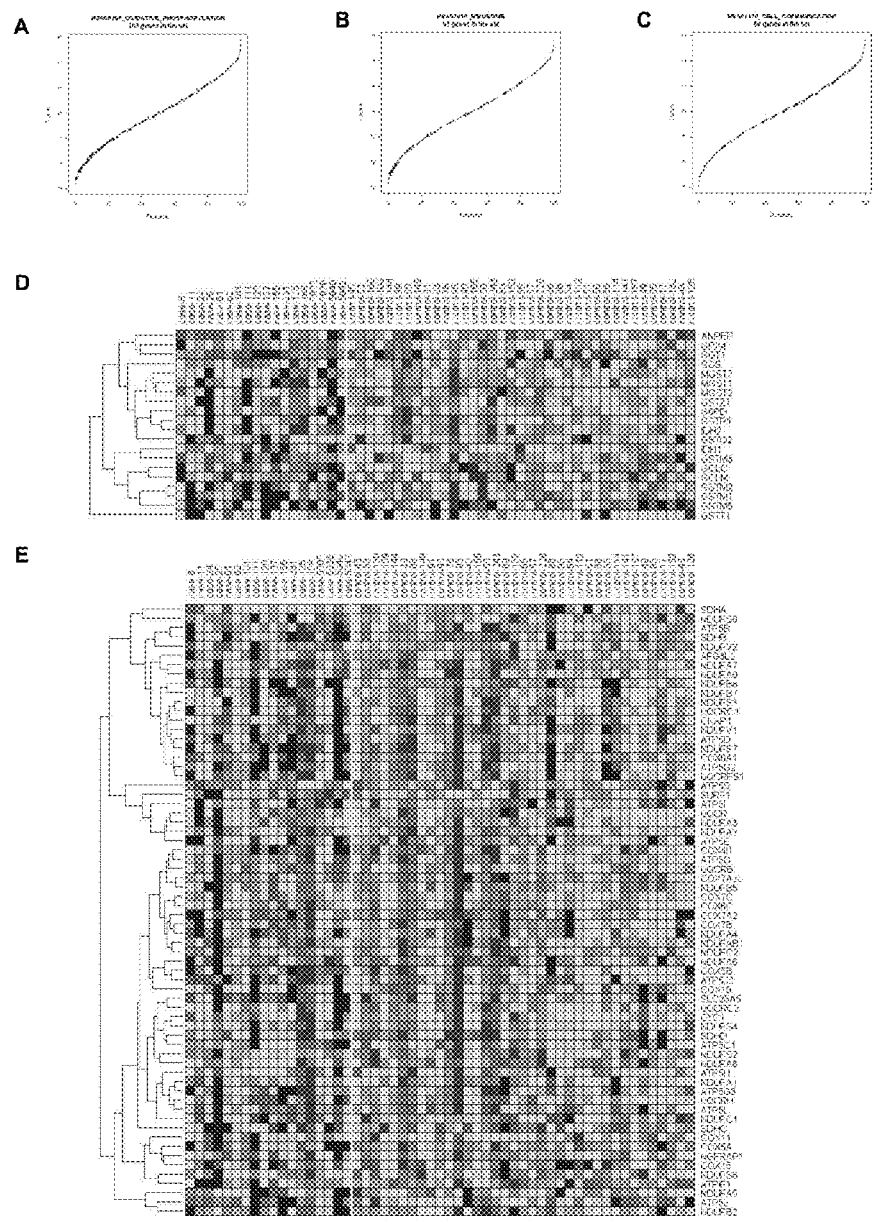

FIG. 16 illustrates altered gene expression in PBSC CD34+ cells from t-MDS/AML cases compared with controls. Enrichment of oxidative phosphorylation (A), ribosomal (B) and cell communication (C) genes in t-MDS/AML PBSC CD34+ cells compared with controls. Expression of leading edge genes for genotoxic and oxidative stress response gene sets (D), and oxidative phosphorylation gene sets in PBSC CD34+ cells from individual cases and controls (E) is also shown.

FIG. 17 is a table summarizing the enrichment of transcription factor binding motifs in genes differentially expressed in PBSC CD34+ cells from t-MDS/AML cases.

FIG. 18 is a table summarizing the canonical pathways represented by genes that were differentially expressed in PBSC CD34+ cells from t-MDS.AML cases compared with controls based on an Ingenuity analysis.

FIG. 19 is a table summarizing the gene ontology categories represented by genes differentially expressed in PBSC CD34+ cells from t-MDS/AML cases compared with controls.

Figure 20:
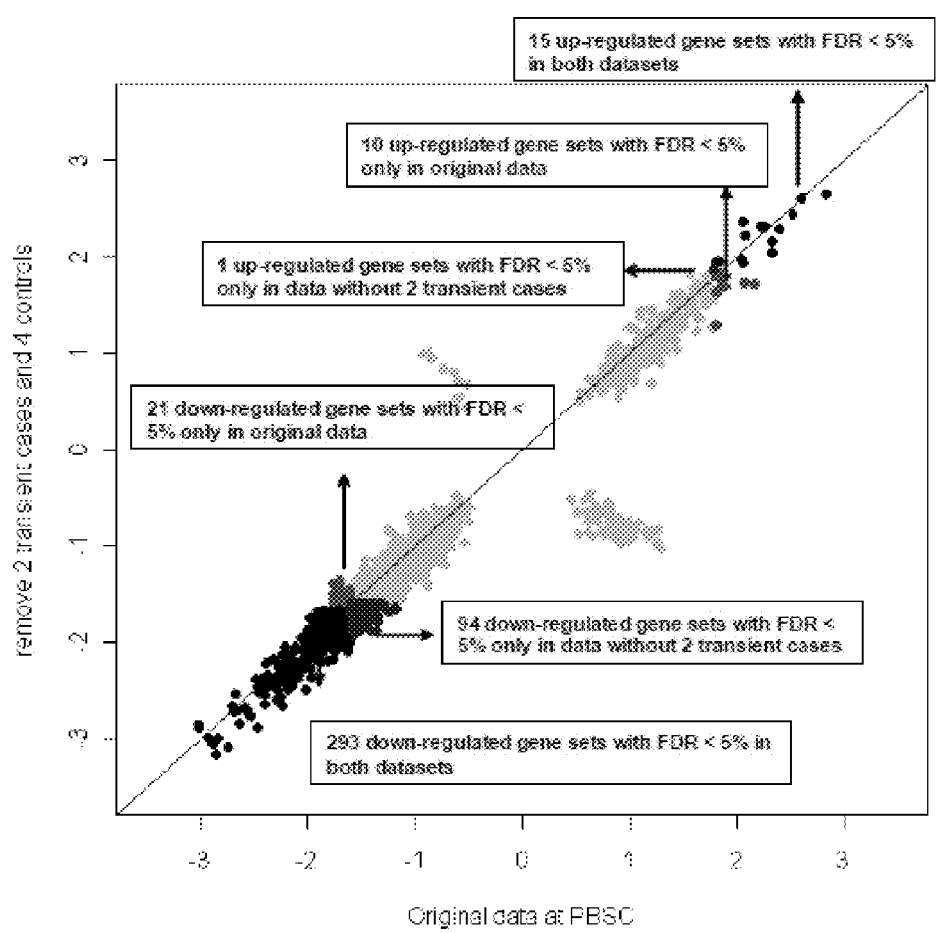

FIG. 20, which is related to FIG. 1 illustrates gene expression in PBSC from t-MDS/AML cases after removal of 2 cases with transient disease and their matching controls compared with the original PBSC analysis. 339 gene sets were significantly altered in the original analysis with FDR<5%; and 403 gene sets were significantly altered in the analysis performed after removal of the 2 cases with transient t-MDS/AML with FDR<5%. The majority (308 gene sets) were common to both analyses.

FIG. 21 is a table summarizing the GSEA analysis of genes that are differentially expressed in PBSC from cases and controls after removind 2 cases with transient t-MDS/AML and their controls.

FIG. 22 illustrates altered gene expression in BM CD34+ cells at time of t-MDS/AML compared with controls. (A)

Differences in gene expression between cases and controls at time of t-MDS/AML are shown for top 50 genes with smallest P-values and 4-fold change in OR (OR>4 or OR<0.25). (B) Normalized enrichment scores (NES) from GSEA analyses for altered gene sets in PBSC CD34+ and BM CD34+ cells at time of t-MDS/AML are plotted. Gene sets significantly upregulated (n=15) or down-regulated (n=203) in both PBSC and t-MDS/AML samples with FDR<5% are highlighted and representative gene sets listed in the boxes. A 50-gene t-MDS/AML signature set representing gene differentially expressed at time of development of t-MDS/AML is also shown. (C) Expression of representative gene sets in BM CD34+ cells from individual cases at time of t-MDS/AML and controls is shown. The expression was averaged over the genes in each gene set and hierarchical clustering performed for samples within the case and control groups. The box indicates the five cases with gene expression resembling that of controls. See also FIGS. 23, 29, 30, 31, 32, and 33.

Figure 22A:
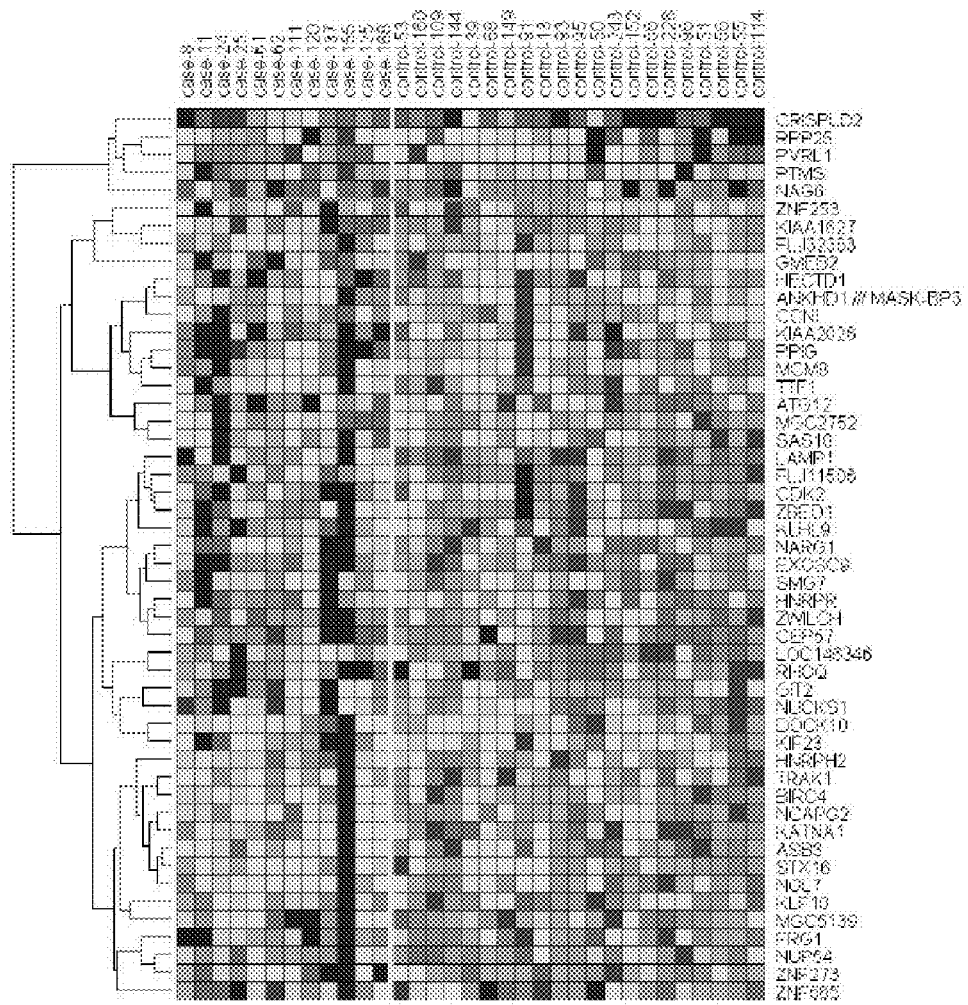
Figure 22B:
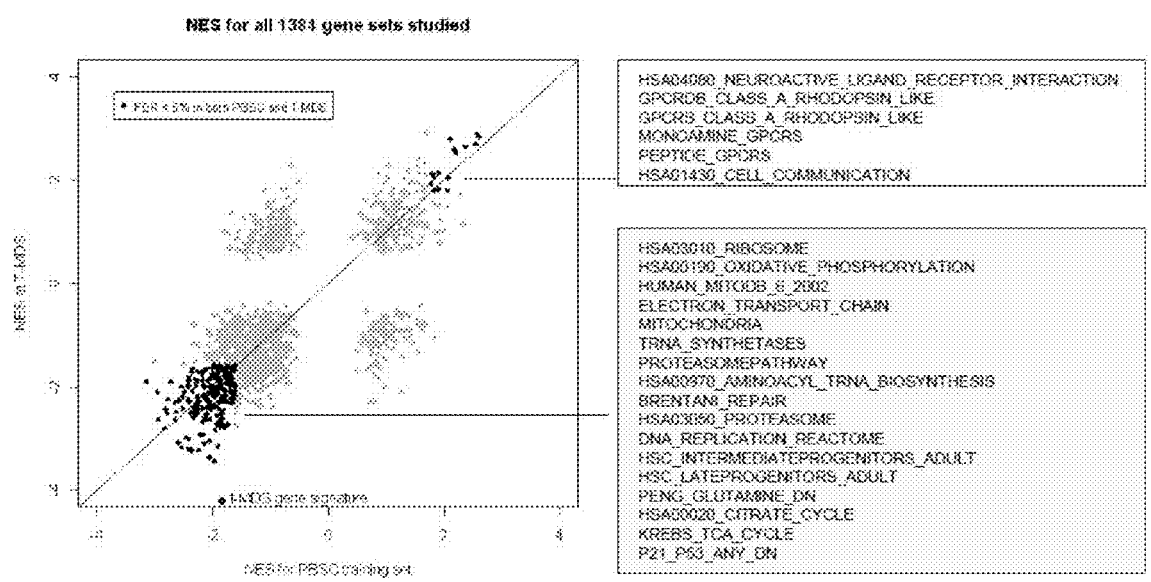
Figure 22C:
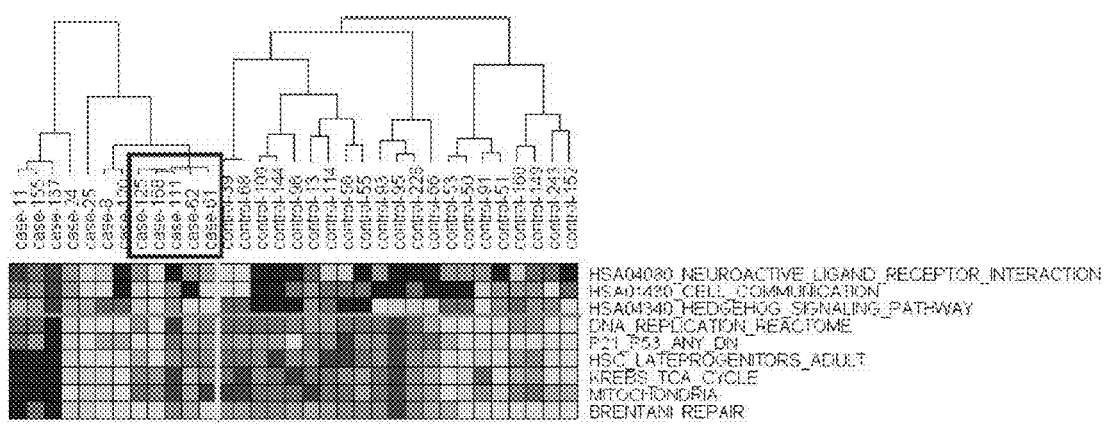
Figure 23:
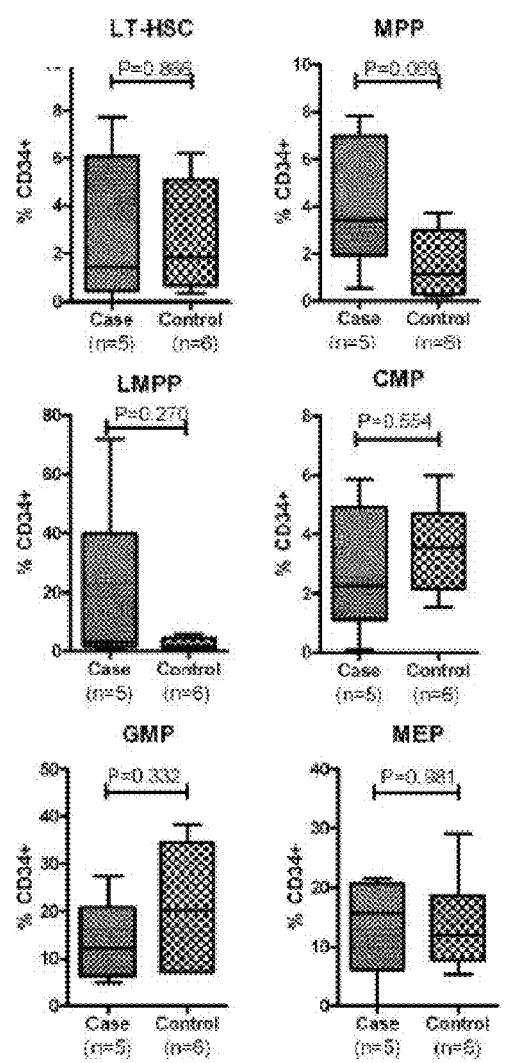

FIG. 23, which is related to FIG. 22. illustrates the lack of difference in frequency of subpopulations of BM CD34+ cells from cases at the time of development of t-MDS/AML and controls. BM cells collected from cases at the time of development of t-MDS/AML and from controls at corresponding time were labeled with lineage markers (CD11b, CD14, Glycophorin A, CD2, CD7, CD10 and CD19), CD34, CD38, CD123, CD90 and CD45RA. CD34+ cells subpopulations including hematopoietic stem cells (HSC; Lin-CD34+CD38-CD45RA-CD90+), multipotent progenitors (MPP; Lin-CD34+CD38-CD45RA-CD90-), lymphoid-primed multipotent progenitors (LMPP; Lin-CD34+CD38-CD45RA+CD90-), common myeloid progenitors (CMP; Lin-CD34+CD38+CD45RA-CD123+), granulocyte-macrophage progenitors (GMP; Lin-CD34+CD38+CD45RA+CD123+) and megakaryocyte-erythroid progenitors (MEP; Lin-CD34+CD38+CD45RA-CD123-) were analyzed using multi-color flow cytometry. No significant difference in frequency of different CD34+ subpopulations was observed between cases and controls. Results represent the median, inter-quartile range and range of values.

FIG. 24 is a table summarizing the gene sets that are enriched in bone marrow CD34+ cells from patients at the time of t-MDS/AML development.

Figure 25:
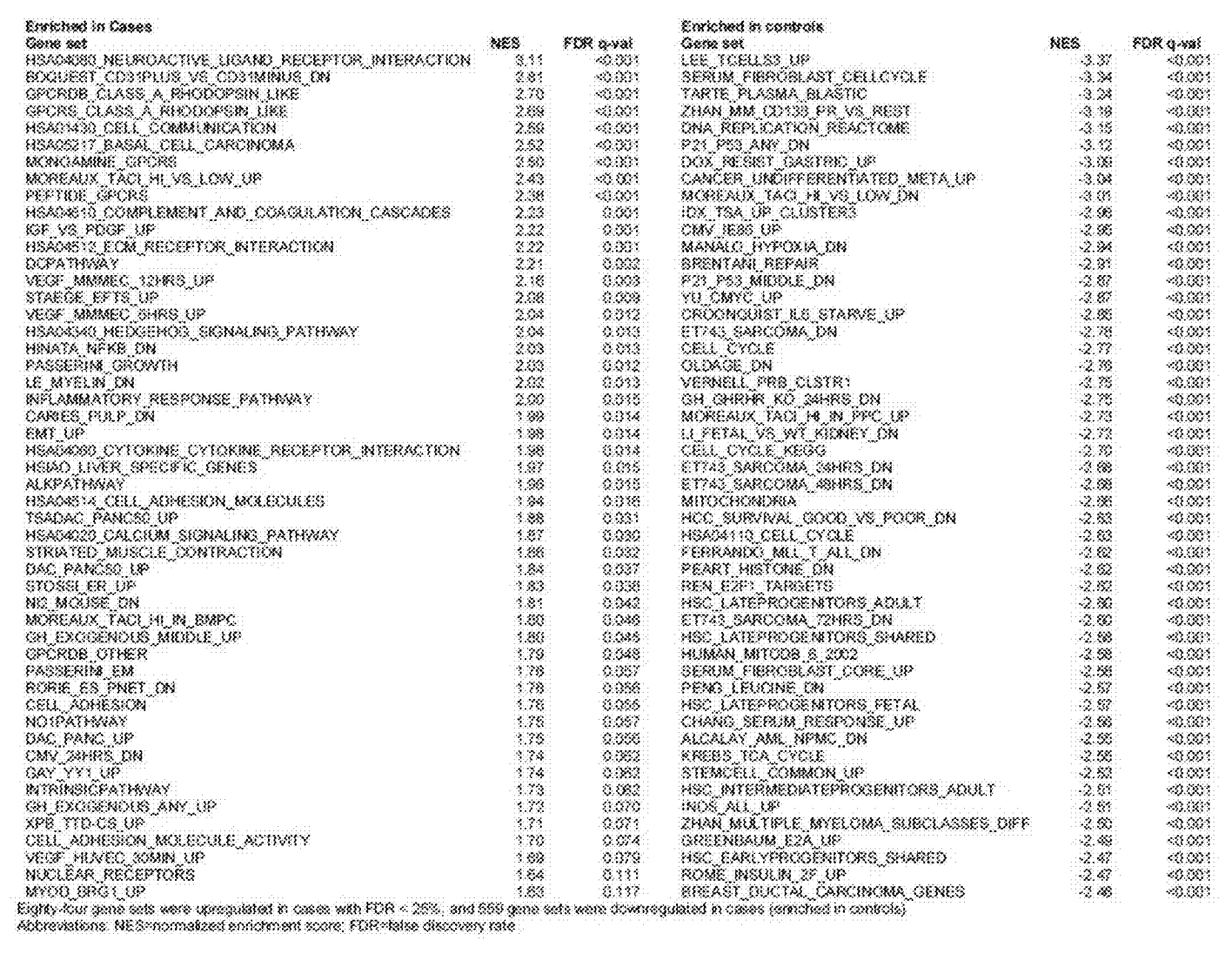

FIG. 25 is a table summarizing the gene sets that are enriched in t-MDS/AML bone marrow CD34+ cells.

Figure 26:
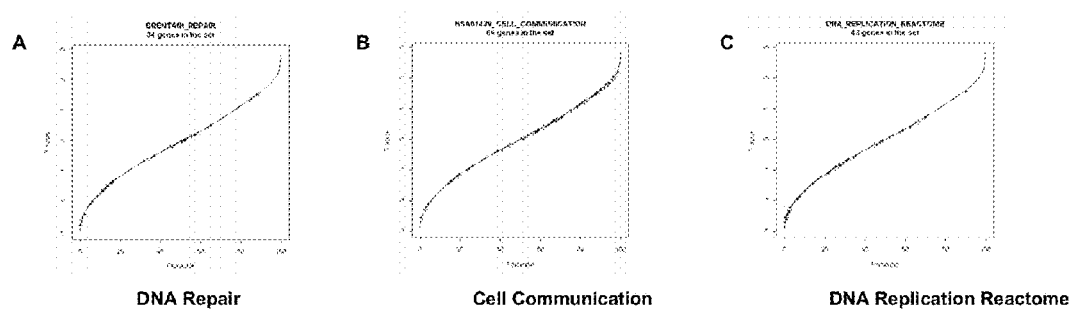

FIG. 26 illustrates altered gene expression in BM CD34+ cells from t-MDS/AML cases compared with controls. Enrichment of (A) DNA Repair, (B) Cell communication, and (C) DNA replication reactome genes in BM CD34+ cells at time of t-MDS/AML compared with controls.

FIG. 27 is a table summarizing the enrichment of transcription factor binding motifs in genes that are differentially expressed in t-MDS/AML bone marrow CD34+ cells.

FIG. 28 is a table summarizing the canonical pathways represented by genes differentially expressed in bone marrow CD34+ cells from t-MDS/AML cases compared with controls based on an Ingenuity analysis.

Figure 29:
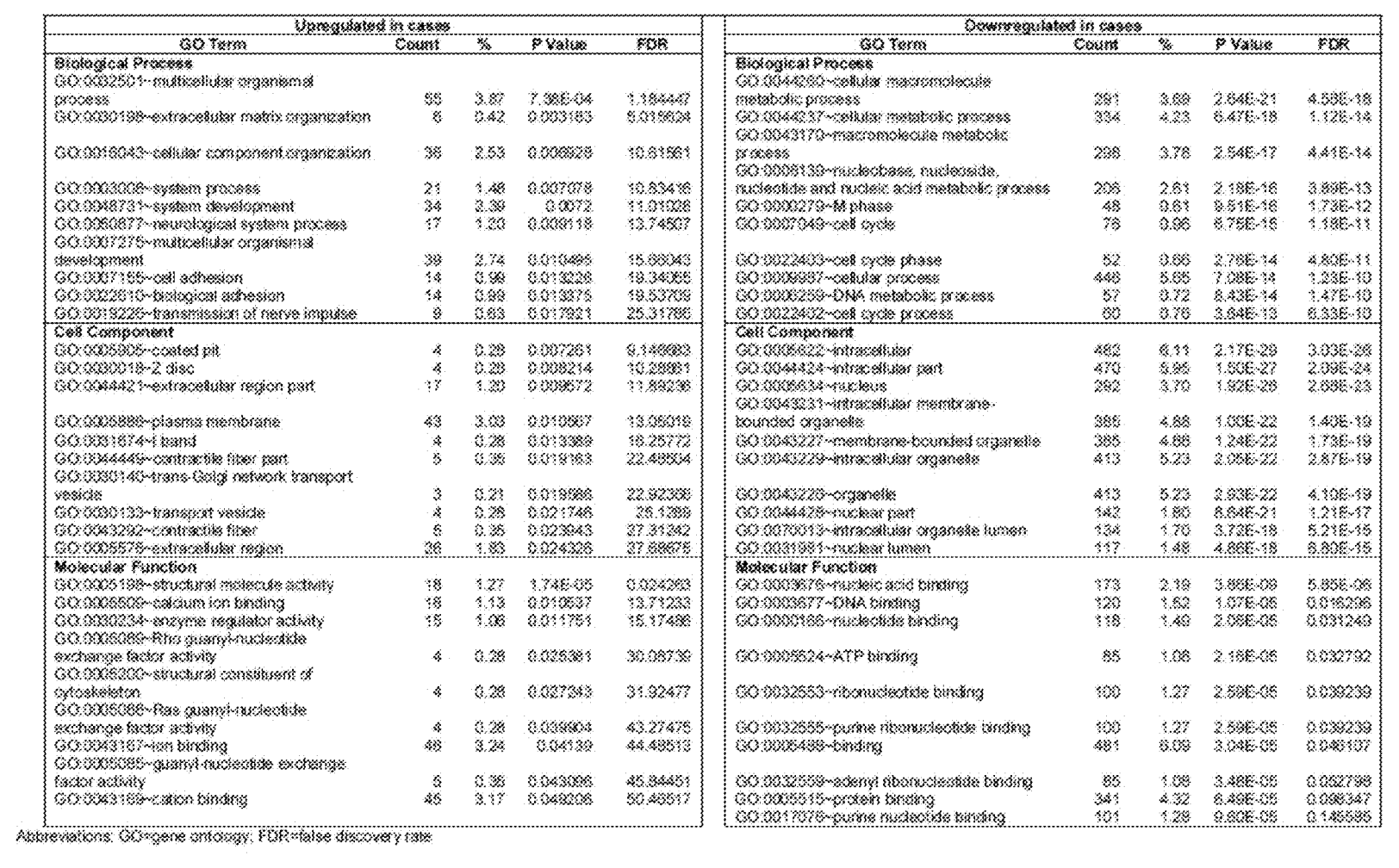

FIG. 29 is a table summarizing gene ontology categories represented by genes that are differentially expressed in bone marrow CD34+_cells from t-MDS/AML cases compared with controls.

Figure 30:
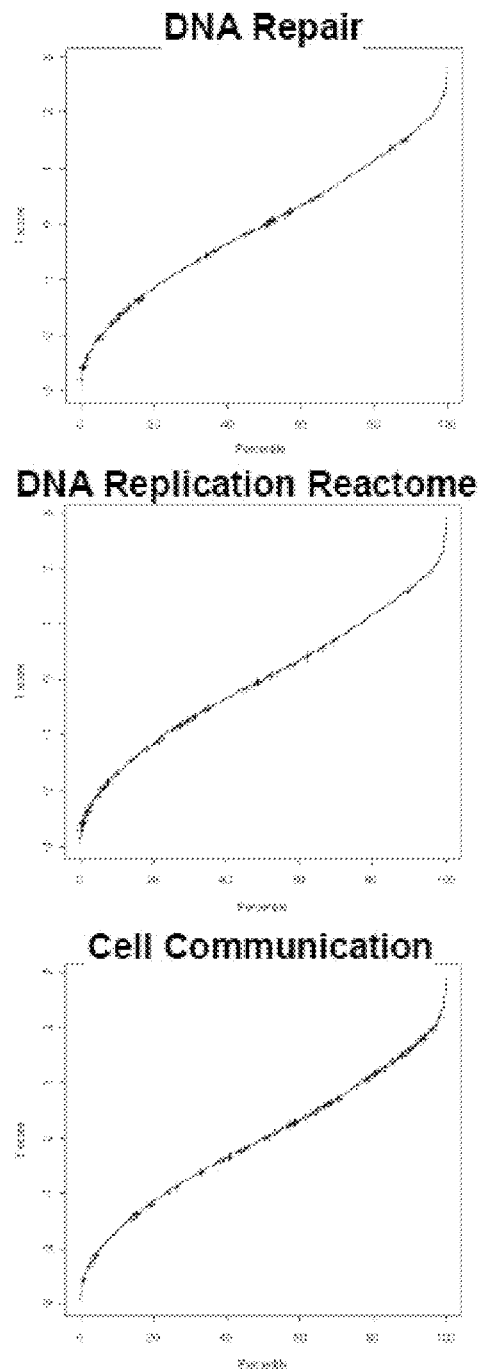

FIG. 30, which is related to FIG. 22 illustrates altered gene expression in BM CD34+ cells from t-MDS/AML cases compared with controls. Enrichment of DNA Repair, Cell communication, and DNA replication reactome genes in BM CD34+ cells at time of t-MDS/AML compared with controls.

FIG. 31A, which is related to FIG. 22 illustrates gene expression in BM CD34+ cells from t-MDS/AML patients compared to normal BM CD34+ cells. Gene expression in 8 normal samples and 12 t-MDS samples were compared using t-test: The heat map represents genes differentially expressed between the two groups using a threshold of FDR5% and abs(log FC)>2 (n=133 genes). In addition, FIG. 31B illustrates gene expression in BM CD34+ cells from control NHL/HL patients that did not develop t-MDS/AML after aHCT compared to normal BM CD34+ cells. Gene expression in 8 normal samples and 21 t-MDS samples were compared using t-test: The heat map represents genes differentially expressed between the two groups using a threshold of FDR5% and abs(log FC)>2 (n=128 genes).

FIGS. 32A and 32B are a pair of tables summarizing gene sets that are enriched in differentially expressed genes between normal bone marrow (BM) CD34+ cells and CD34+ cells from t-MDS/AML cases or controls. (* Bold text represents genes that are common to t-MDS/AML cases and NHL/HL controls; **Abbreviations: NE=normalized enrichment score; FDR=False Discovery Rate).

Figure 33:
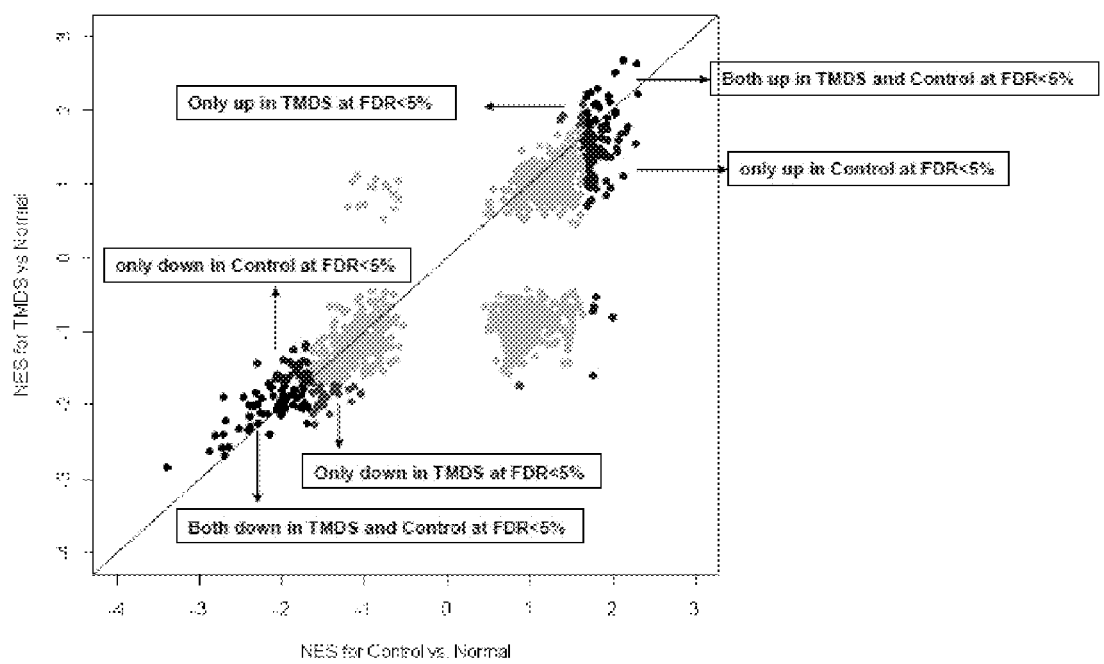

FIG. 33, which is related to FIG. 22, illustrates gene expression in BM CD34+ cells from NHL/HL patients that did or did not develop t-MDS/AML compared to normal BM CD34+ cells. Normalized enrichment scores (NES) from GSEA analyses for altered gene sets in BM CD34+ cells from patients at time of t-MDS/AML compared with normal BM CD34+ cells were plotted against NES for altered gene sets in BM CD34+ cells from controls that did not develop t-MDS/AML after aHCT. Gene sets that were significantly upregulated or downregulated in both t-MDS/AML and control samples with FDR<5% are highlighted in black. Those altered only in t-MDS/AML samples in red; and those altered only in controls in blue.

Figure 34:
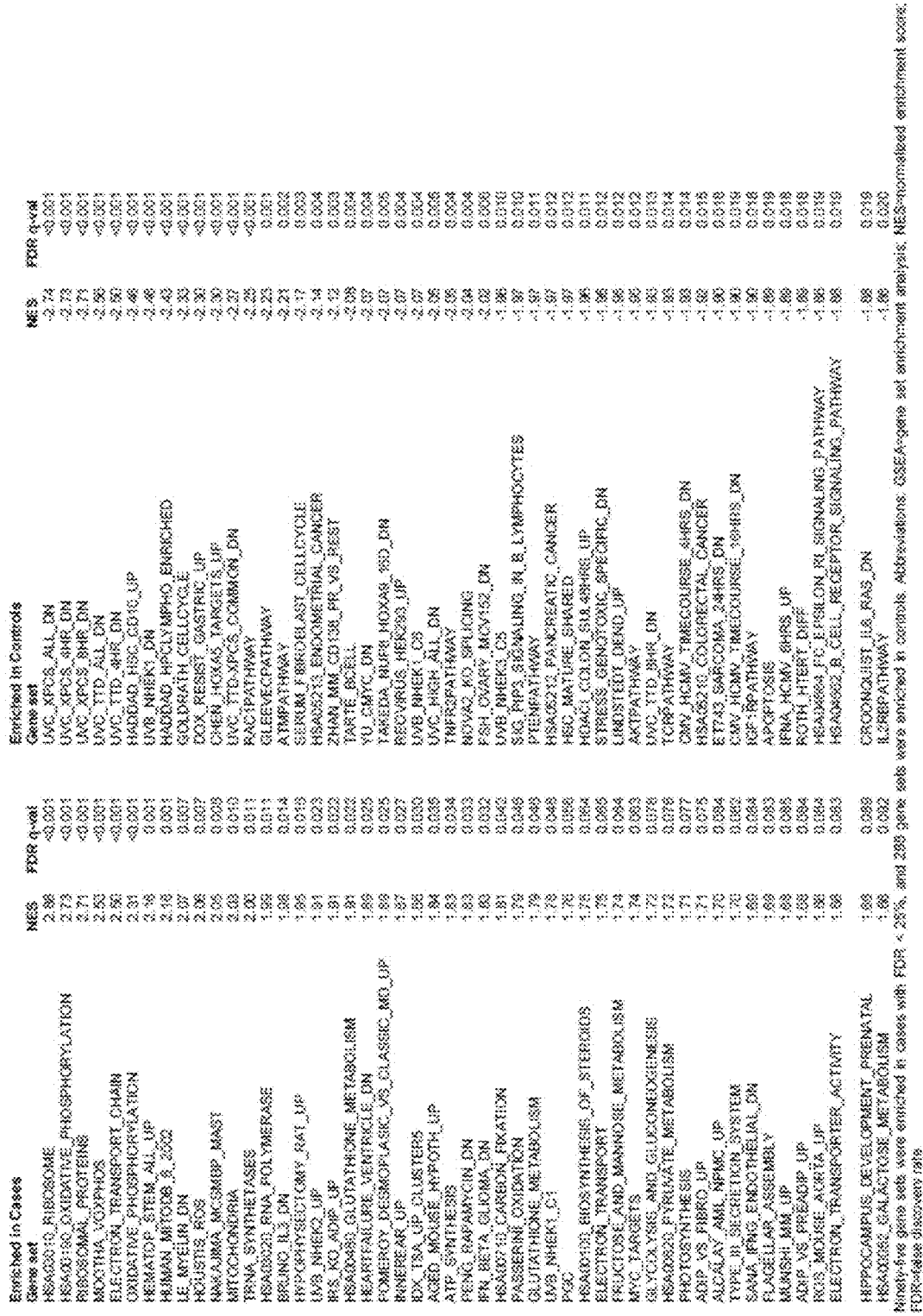

FIG. 34 is a table summarizing the GSEA analysis of genes showing a significant increase or decrease in expression over time from PBSC collection to development of t-MDS/AML in cases compared to controls over a similar time period.

FIG. 35 illustrates changes in gene expression in CD34+ cells in the course of development of t-MDS/AML. (A) Changes in gene expression from PBSC to development of t-MDS/AML. Normalized enrichment scores (NES) from GSEA analyses for altered gene sets in PBSC CD34+ and BM CD34+ cells at time of t-MDS/AML are plotted. Gene sets significantly upregulated (dark dots, *) or downregulated (dark dots, **) in cases compared to controls from time of PBSC collection to time of t-MDS/AML with FDR<5% are highlighted and representative gene sets are listed in the boxes. (B) Gene expression signatures that are upregulated and downregulated in cases compared to controls in PBSC and at time of development of t-MDS/AML, as well as changes in gene expression from time of PBSC to development of t-MDS/AML are summarized. See also FIG. 34.

Figure 36:
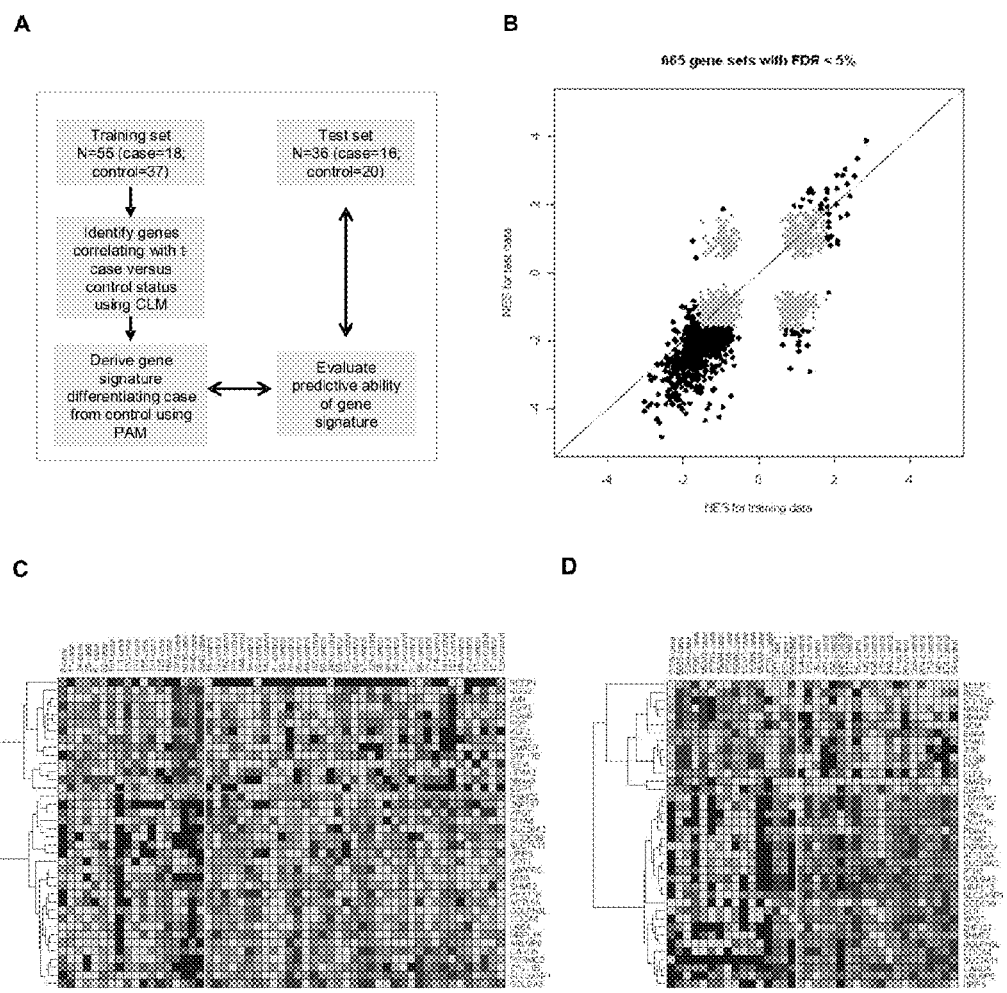

FIG. 36 illustrates the validation of altered gene expression in PBSC from t-MDS/AML cases and outcome prediction. (A) Strategy for development and validation of a gene signature to differentiate PBSC from cases and controls. PAM represents prediction analysis of microarrays. (B) Normalized enrichment scores (NES) from GSEA analyses for 665 gene sets with FDR<5% in PBSC CD34+ from either training set or test set are highlighted. Six hundred and thirty six (95.6%) sets were in agreement between the two studies, with 34 gene sets upregulated and 602 gene sets downregulated in both training and test sets. (C) Expression for the 38-gene signature derived using PAM in the training PBSC set. (D) Expression for the 38-gene signature in the test PBSC set. The boxes indicate the three subjects that were misclassified by the gene signature. See also FIGS. 6, 37, 38, 39, and 40.

Figure 37A:
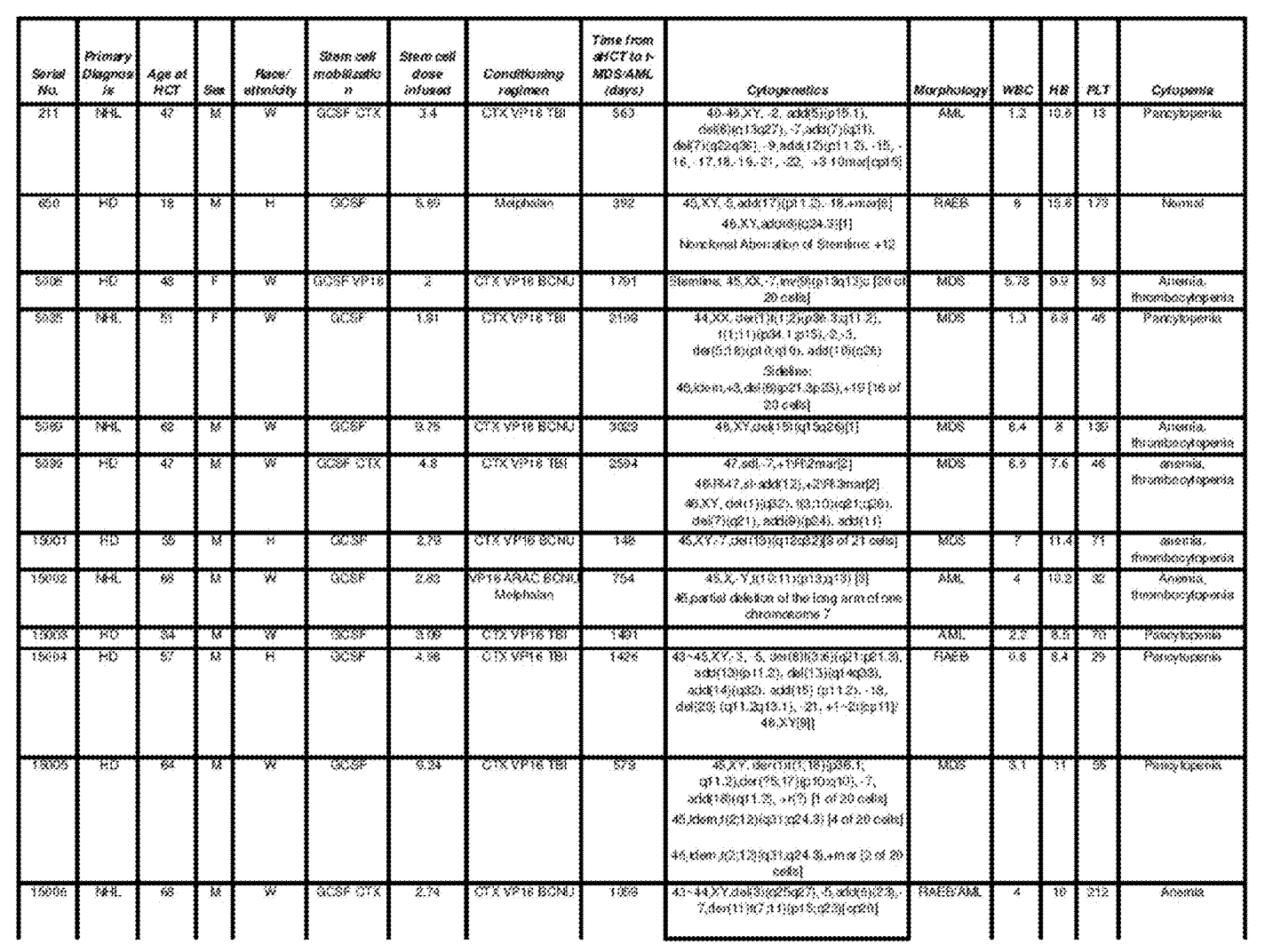

FIG. 37 is a pair of tables summarizing the clinical characteristics of t-MDS/AML cases in test sets (A) and comparison of clinical and demographic characteristics and therapeutic exposures of t-MDS/AML cases in the training and test sets (B).

Figure 38:
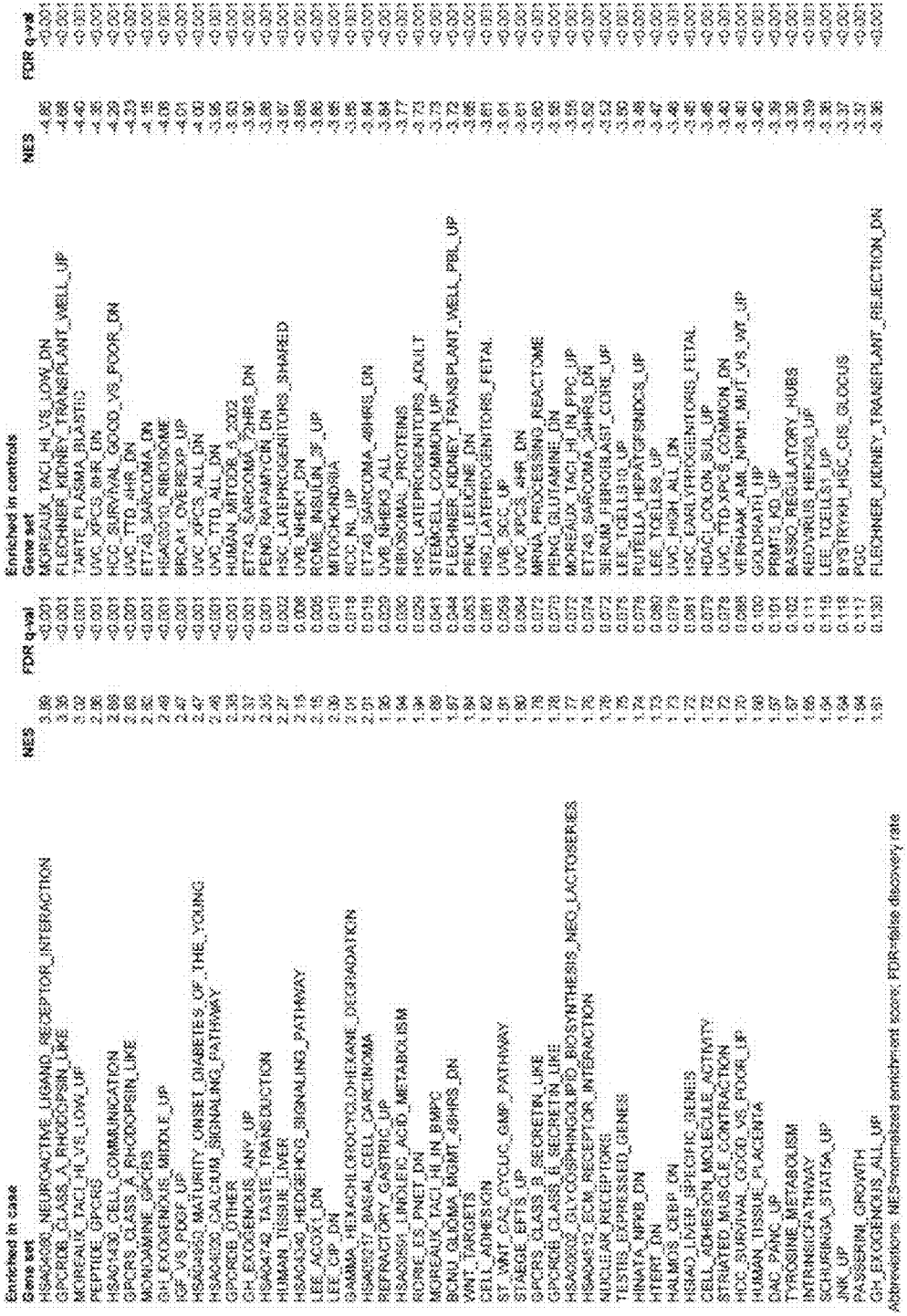

FIG. 38 is a table summarizing the gene sets that are enriched in PBSC CD34+ cells from t-MDS/AML cases in the test set.

Figure 39:
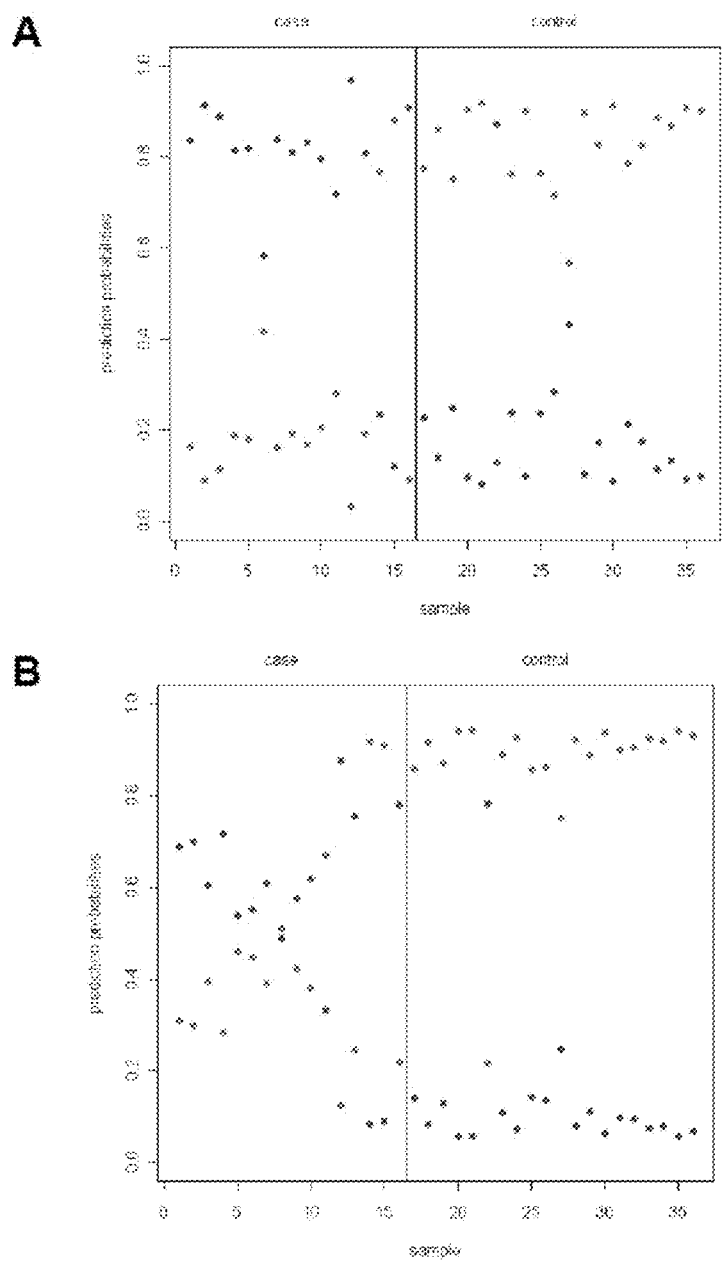

FIG. 39 illustrates (A) prediction probabilities for t-MDS/AML versus control status in test set using the 38-gene signature. The 38-gene signature derived from the training set was applied to the test set. The posterior probabilities of being t-MDS (dark gray) or control (light gray) are shown. The signature successfully predicted disease status for the majority of the subjects. All controls were predicted correctly, except one subject. There are 2 misclassifications in predicting t-MDS. Most subjects were classified with high prediction probability. (B) Prediction probabilities for t-MDS/AML versus control status in test set using the 31-gene signature. The 2 cases with transient t-MDS/AML and their controls were removed from the training sets for the analysis and a 31-gene signature selected with lowest prediction error in cross-validation. Application of the 31-gene signature to the test set misclassified 4/16 cases as controls and 1/20 controls as cases in the test set.

FIG. 40 is pair of tables summarizing the cytogenic analysis of t-MDS/AML cases at a pre-HCT time point in the training and test sets (A) (* t-MDS/AML cytogenetics are shown only for those cases that had nonclonal aberrations detected in pre-HCT bone marrows; and show that these aberrations were not seen at time of development of t-MDS/AML). Further, Whole chromosome painting was performed for chromosomes 1 (DEAC), 5 (FITC), 7 (SpO), 11 (Texas Red), 21 (Cy5) (B).

FIG. 41. Mitochondrial dysfunction and metabolic abnormalities in PBSC from patients developing t-MDS/AML. (A) Mitochondrial ROS and total ROS levels in PBSC CD34+ cells from cases and controls detected with C-H2DCFDA and MitoSox RED respectively. (B) Expression of Nrf2 regulated anti-oxidant genes heme oxygenase 1 (HMOX1), peroxiredoxin 3 (PRDX3) and superoxide dismutase 2 (SOD2) in PBSC CD34+ cells from cases (n=20) and controls (n=39) quantified using Q-PCR. (C) ROS levels in PBSC CD34+ cells from cases and controls, measured 2 hours after exposure to etoposide (VP-16), nitrogen mustard (NM) and methylene blue with visible light (MB+Light) by C-H2DCFDA labeling. (D) DNA damage in PBSC CD34+ cells from cases and controls, measured 4 hours after exposure to radiation (2Gy), VP-16 and NM as well as no treatment controls (NT) by measuring γ-H2AX levels. (E) NADH levels in PBSC CD34+ cells from cases and controls measured at baseline and after rotenone treatment. (F) Mitochondrial mass was estimated in PBSC MNC isolated from cases (n=19) and controls (n=16) through measurement of mitochondrial DNA content. See also FIG. 42.

FIG. 42, which is related to FIG. 41, illustrates a lack of difference in ROS levels in different subpopulations of CD34+ cells obtained from normal PBSC samples. Normal PBSC MNCs were treated with or without etoposide (VP-16) and methylene blue with visible light (MB) and stained with lineage markers (CD11b, CD14, Glycophorin A, CD2, CD7, CD10 and CD19), CD34, CD38, CD123, CD45RA and ROS indicator C-H2DCFDA. ROS levels in different CD34 subpopulations including HSC (Lin-CD34+CD38-), CMP (Lin-CD34+CD38+CD45RA-CD123+), GMP (Lin-CD34+CD38+CD45RA+CD123+) and MEP (Lin-CD34+CD38+CD45RA-CD123-) as well as total CD34+ cells were analyzed using multi-color flow cytometry. (A) Baseline ROS levels in different CD34 subpopulations from normal PBSC samples. There was no significant difference among different CD34 subpopulations. Results represent median, interquartile range and range of values. (B) ROS levels in different CD34 subpopulations of normal PBSC measured 2 hours after exposure to etoposide (VP-16) and methylene blue with visible light (MB). No significant difference among different CD34 subpopulations was observed. Results represent median, interquartile range and range of values.

DETAILED DESCRIPTION

A gene expression signature associated with the development of therapy related myelodysplasia or acute myeloid leukemia (t-MDS/AML) is provided herein. An "expression signature" is a group two or more genes or gene-related molecules (e.g., DNA, RNA, amino acids and proteins) that exist in a cell, tissue fluid or other sample whose combined expression pattern is characteristic of a particular tissue or is characteristic of a particular condition, or disease state. The expression signature can be used to select or stratify a group of subjects based on, for example, a specific stage of a disease, a risk of developing a particular disease or state of disease or a probability or prediction of a prognosis, with sufficient accuracy to facilitate diagnosis or selection of treatment.

According the embodiments described herein, a gene expression signature described herein includes a set of two or more genes that are expressed in CD34+ or other related hematopoietic cells and are associated with the development of t-MDS/AML. The set of two or more genes in the gene signature may include those genes related to cellular functions and responses including, but not limited to, mitochondrial oxidative phosphorylation, protein synthesis, cell cycle, DNA repair, response to injury, G-coupled receptors, hematopoietic regulation, cell adhesion and cell communication. In one embodiment, the two or more genes of the gene expression signature are selected from NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2

In another embodiment, the gene expression signature is a set of 38 genes that are expressed in CD34+ or other related hematopoietic cells and are associated with the development of t-MDS/AML. The set of 38 genes are NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2 (See FIG. 6).

Figure 2:
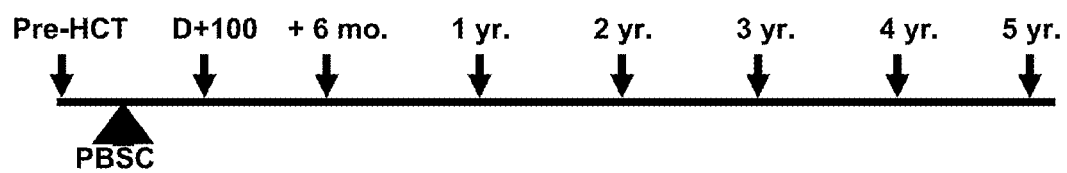
FIG. 2 illustrates the timeline of the prospective cohort study of patients receiving aHCT for lymphoma. Serial bone marrow and blood samples were taken pre-transplant and at several time points post-transplant. Samples were aliquoted and stored for various studies described herein to evaluate pathogenesis of t-MDS/AML and to identify markers that can predict of its development.

To generate a gene expression signature as described herein and to improve the understanding of the pathogenesis of t-MDS/AML, a prospective cohort of patients undergoing aHCT for HL or NHL was constructed. Patients were followed longitudinally with a collection of peripheral blood stem cells (PBSC) and bone marrow (BM) samples prior to a-HCT, and serial BM samples for 5-years post aHCT (FIG. 2). The samples collected in this cohort are referred to herein as a "training set." This study design allows use of a nested case-control approach was used to compare gene expression profiles in CD34+ hematopoietic stem and progenitor cells (HSC) from patients who developed t-MDS/AML after aHCT ("cases") with patients who did not develop t-MDS/AML ("controls"). Peripheral blood stem cells (PBSC) obtained prior to aHCT and bone marrow (BM) samples obtained at time of t-MDS/AML post-aHCT were obtained for the studies described herein and were used to identify gene expression changes that occur prior to aHCT in patients who subsequently developed t-MDS/AML after aHCT. Genes that were expressed prior to aHCT were then compared with those expressed at the time of developing of overt disease. In addition, through the use of an independent sample set, it was determined that gene expression in pre-aHCT samples could accurately identify patients at risk for post-aHCT t-MDS/AML.

Figure 3:
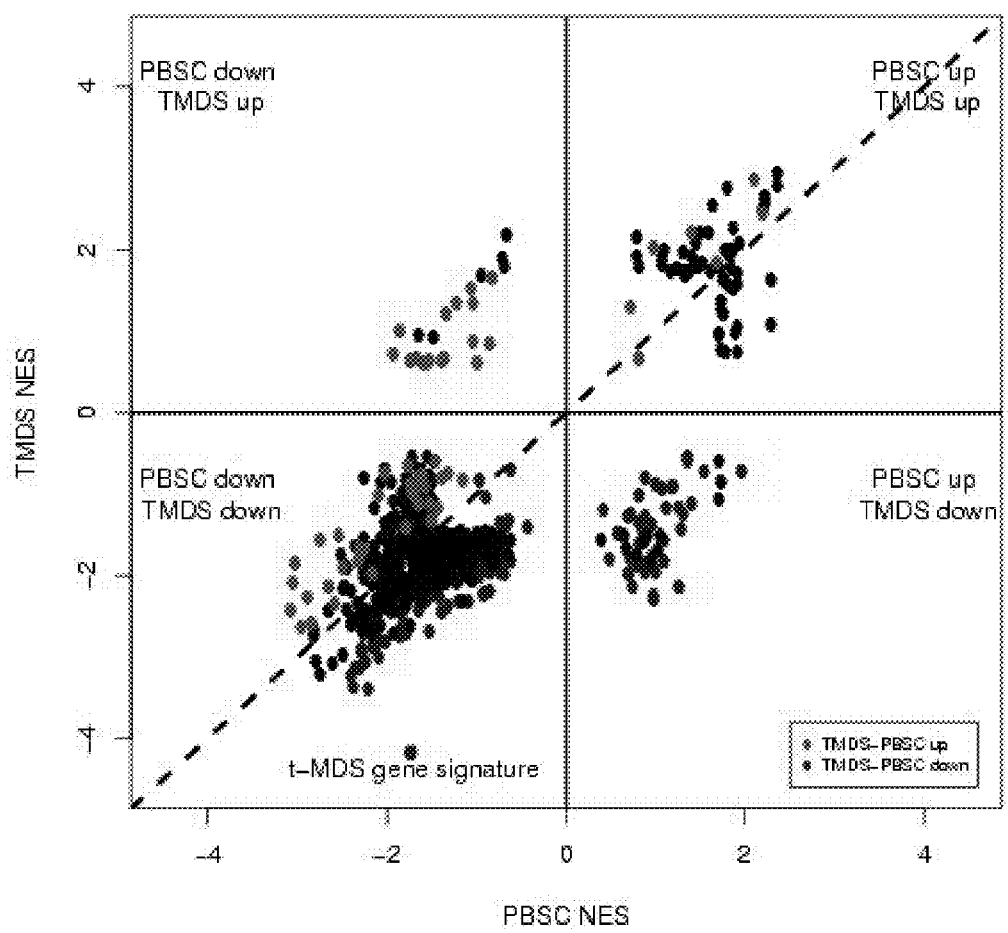
FIG. 3 illustrates a comparison of gene sets enriched in CD34+ cells from PBSC and bone marrow at the time of developing t-MDS/AML. Enrichment scores for gene sets from cells obtained from PBSC were compared to gene sets from cells obtained at the time of t-MDS/AML. The x-axis shows the enrichment score in PBSC and the y-axis shows the enrichment scores in t-MDS/AML bone marrow samples.

From the studies described above, a gene expression signature to predict risk of t-MDS/AML in pre-HCT PBSC samples was generated and validated in an independent test set. Significant differences in gene expression were seen in PBSC obtained pre-aHCT from patients who subsequently developed t-MDS/AML compared to controls (FIGS. 3 and 4). Altered gene expression in PBSC samples was validated in an independent group of patients and a 38-gene PBSC classifier derived from the training set was identified and that accurately distinguished patients in the independent group who developed t-MDS/AML after aHCT from those who did not.

Changes in gene expression associated with development of t-MDS/AML after aHCT for lymphoma were identified in CD34+ cells from PBSC obtained pre-aHCT, long before development of clinically overt disease. These changes, which occur early in the course of t-MDS/AML development, may represent factors predisposing to risk of t-MDS/AML and/or effects of pre-aHCT therapeutic exposures.

PBSC CD34+ cells from patients who develop t-MDS/AML demonstrated altered expression of genes related to mitochondria, oxidative phosphorylation, oxidative stress response, ribosomes, and DNA repair. In additional studies, PBSC CD34+ cells from cases that develop t-MDS/AML were shown to demonstrate altered mitochondrial function, increased ROS generation, reduced ROS detoxification, and enhanced DNA damage after therapeutic exposure, validating and extending the results of gene expression analysis. It is thought that mitochondrial defects are central to cancer cell biology, through enhanced ROS generation leading to mutation of critical genes that regulate cell proliferation (FIG. 5). Mitochondrial oxidative phosphorylation, in addition to its role in energy production, is a major source of reactive oxygen species (ROS) generation (Kowaltowski et al. 2009). Impaired electron transfer could result in increased ROS generation in PBSC from patients at risk for t-MDS/AML (Wallace 2005). Reduced anti-oxidant gene expression may further increase ROS levels. Tight regulation of ROS is essential for normal hematopoietic function (Ito et al. 2004). Development of t-MDS/AML post-aHCT is preceded by impaired hematopoietic function evidenced by impaired PBSC mobilization; reduced progenitor regeneration, and accelerated telomere loss (Bhatia et al. 2005; Chakraborty & Sun 2009). These findings support a model of t-MDS/AML where therapeutic exposure results in increased ROS levels related to mitochondrial dysfunction, increased DNA damage, mutagenesis, and impaired hematopoiesis (FIG. 7). Impaired ribosomal function may also contribute to hematopoietic impairment in patients developing t-MDS/AML. Ribosomal gene mutations and impaired ribosome biogenesis occur in congenital BM failure syndromes and the 5q-syndrome, and may impair hematopoiesis through altered protein translation, or through p53-dependent apoptosis and senescence (Ebert et al. 2008; Liu & Ellis 2006; Fumagalli et al. 2009). It was previously shown that development of t-MDS/AML is preceded by impaired hematopoietic function evidenced by impaired PBSC mobilization; reduced regeneration of committed progenitors, and accelerated telomere loss.

Changes in gene expression from PBSC to development of t-MDS/AML likely represent abnormalities associated with transformation from the pre-leukemic to leukemic state. Progression to t-MDS/AML was associated with reduced expression of DNA repair and cell cycle regulatory genes, indicating loss of genome protective mechanisms, potentially allowing acquisition of additional mutations and disease evolution (Harper & Elledge 2007; Kastan & Bartek 2004). Such changes may result from acquisition of additional mutations or epigenetic changes in pre-malignant cells. Mutations in HRR genes are reported in t-MDS/AML patients (Rassool et al. 2007). Altered expression of cell cycle related genes was reported in t-MDS/AML cells (Qian et al. 2002), and mutations in p53 are relatively frequent (Ben-Yehuda et al. 1996). Loss of p53-related cell cycle regulation may contribute to genetic instability as well as survival and expansion of altered hematopoietic cells in t-MDS/AML (Fumagalli et al. 2009; Feldser & Greider 2007). In addition to its role in the DNA damage response, p53 also plays an important role in senescence and apoptosis in response to ribosomal defects, which were also observed in gene expression analysis of t-MDS/AML CD34+ cells.

Changes in gene expression patterns that were observed in t-MDS/AML cases may also be related in part to alternative genetic pathways to t-MDS/AML development, as have been defined based on characteristic chromosome abnormalities (Pedersen-Bjergaard et al., 2007). In the current study, variability of gene expression was associated with certain types of chromosomal abnormalities (20q-; 13q-).

The 38-gene predictor compares well with other recently reported multi-gene signatures for various cancers. Although a perfect test should ideally have 100%, sensitivity and specificity, such sensitivity and specificity is not achieved by any currently available biomarker (Wagner et al., 2004). For example, the best biomarker currently known for prostate cancer, PSA, has a sensitivity of 90% and specificity of 25%. A 29 microRNA-gene signature for non-small cell lung cancer in peripheral blood mononuclear cells had a 76% sensitivity and a 82% specificity of prediction in an independent set of 38 cases and 17 controls (Raponi et al., 2009). A 75-probe signature in CD34+ cells predicted drug response to imatinib in CML patients with 88% sensitivity and 83% specificity in an independent test set of 17 responders and 6 non-responders (Oehler et al., 2009). Thus, taking into account the previously published predictors, the 38-gene signature for t-MDS/AML performed favorably in classifying cases and controls. This is especially notable since the signature was obtained from and applied to samples procured several years prior to development of overt disease.

These results indicate that genetic programs associated with t-MDS/AML are perturbed long before disease onset, and can accurately identify those at risk of developing this complication. The current study, therefore, may have important clinical significance, since early detection of patients at high risk for t-MDS/AML using a gene expression signature may facilitate application of interventions for preventing development of this lethal malignancy. Detection of the high risk profile may provide guidance for therapeutic decision-making including the use of alternative treatment approaches such as allogeneic transplantation (Litzow et al.), and application of targeted interventions for those at high risk (FIG. 8). Although interventions that reduce the risk of progression to t-MDS/AML do not currently exist, insights into critical molecular mechanisms contributing to susceptibility to and emergence of t-MDS/AML could provide potential targets for development of preventive or therapeutic interventional strategies. For example, enhanced mitochondrial ROS levels can be explored as a potential target for interventions to prevent t-MDS/AML in patients receiving genotoxic cancer therapy (Colburn and Kensler, 2008).

Therefore, methods for predicting risk for developing therapy related myelodysplasia or acute myeloid leukemia (t-MDS/AML) after autologous hematopoietic cell transplantation (aHCT) using a gene expression signature according to the embodiments described herein are provided. In one embodiment, the method includes detecting a test expression level of a set of two or more genes of a gene expression signature in a biological sample (or "test sample") from a subject, comparing the test expression level to a set of corresponding training expression levels that include a training case expression level and a training control expression level, and predicting a high risk of developing t-MDS/AML when the test expression level is at or about the training case expression level or predicting a low risk of developing t-MDS/AML when the test expression level is at or about the training control expression level. In some embodiments, the biological sample may be a blood sample, a bone marrow (BM) sample, or any other suitable sample enriched with peripheral blood stem cells (PBSC). In certain embodiments, the biological sample may contain putative CD34+ cells.

A biological sample refers to any material, biological fluid, tissue, or cell obtained or otherwise derived from a subject including, but not limited to, blood (including whole or unfractioned blood, leukocytes, peripheral blood mononuclear cells, buffy coat, plasma, and serum), bone marrow, sputum, tears, mucus, nasal washes, nasal aspirate, breath, urine, semen, saliva, meningeal fluid, amniotic fluid, glandular fluid, lymph fluid, milk, bronchial aspirate, synovial fluid, joint aspirate, cells, a cellular extract, and cerebrospinal fluid. A biological sample may also include an experimentally separated fraction of any material, biological fluid, tissue, or cell including the preceding. For example, a blood sample can be fractionated into serum or into enriched fractions containing particular types of blood cells, such as red blood cells, white blood cells (leukocytes), and peripheral blood stem cells (PBSC). A biological sample may also include materials containing homogenized solid material, such as from a tissue sample, or a tissue biopsy; or materials derived from a tissue culture or a cell culture.

As used herein, the terms "training expression level, "training case expression level" and "training control expression level" refer to a specific value or dataset that can be used to predict, prognose or classify the value (e.g., expression level or reference expression profile obtained from the test sample associated with an particular group). In one embodiment, a dataset may be obtained from samples from a group of subjects that have undergone aHCT (i.e., the "training set"). The training set includes subjects that developed t-MDS/AML after aHCT (i.e., "cases" or "case set") or from a group of subjects that did not develop t-MDS/AML (i.e., "controls" or "control set"). The expression data of the biomarkers in the dataset can be used to create a control or reference value that is used in testing the biological samples from the subjects. A training case expression level, training control expression level or other associated control values are obtained from the historical expression data for a patient or pool of patients with a corresponding outcome. In some embodiments, the training expression values are numerical thresholds for predicting outcomes, for example good and poor outcome, development of a particular condition or making therapy recommendations.

Early detection of patients at risk for t-MDS/AML using gene expression analysis may provide guidance for preventative or therapeutic decisions including the use of alternative treatment approaches such as allogeneic transplantation (Litzow et al.) and application of targeted interventions for those at high risk. Furthermore, insights into critical molecular mechanisms contributing to susceptibility to and emergence of t-MDS/AML could provide potential targets for development of interventional strategies. For example, enhanced mitochondrial ROS levels may be a potential target for interventions to prevent t-MDS/AML in patients receiving genotoxic cancer therapy (Colburn & Kensler 2008).

In another embodiment, kits used to predict a subject's risk of developing t-MDS/AML are provided herein. The kits include, but are not limited to, detection agents that can detect the expression products of the biomarkers. Detection agents, as used herein refer to any agent that that associates or binds directly or indirectly to a molecule in the sample. In certain embodiments, a detection reagent may include, but is not limited to, antibodies or fragments thereof, nucleic acid probes, aptamers, capture agents, or glycopeptides.

Accordingly, in one embodiment, a kit to predict a subject's risk of developing t-MDS/AML is provided. The kit may include detection agents that can detect the expression products of a gene signature, wherein the gene expression signature includes a set of two or more genes that are expressed in CD34+ or other related hematopoietic cells. The two or more genes may be selected from the following genes: NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2. In another embodiment, the kit may include detection agents that can detect the expression products of a gene expression signature that includes a set of 38 genes. The set of 38 genes are NR4A2, FOS, EGR1, CARD6, PEX11B, EGR3, EGR4, MRPL15, SLC7A11, REEP1, FOSB, GOLGA5, ACTL6A, GOLPH3L, CCDC99, SMAD7, SHMT2, LRPPRC, CDCA4, PDIA4, GOT1, RTN3, KLF2, JUN, STK17B, PSMC2, LRBA, XPOT, ZYG11B, ZNF137, GEM, PGRMC2, ARL61P6, SLC2A3P1, NR4A3, RGS2, NRIP3 and SLC26A2 (FIG. 6)

In some embodiments, a kit may include containers, each with one or more of the various detection agents. For example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes (e.g., appropriate length poly(T) or random primers linked to a promoter reactive with the RNA polymerase). A kit can also include a control or reference standard and/or instructions for use thereof. In addition, a kit can include additional agents such as buffers or stabilizers and/or vessels for storing or transporting the detection agents Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Altered Hematopoietic Cell Gene Expression Precedes Development of t-MDS/AML and Identifies Patients at Risk Methods Patients and Samples.

The study was approved by an institutional review board in accordance with an assurance filed with and approved by the Department of Health and Human Services, and met all requirements of the Declaration of Helsinki. Informed consent was obtained from all subjects. Patients receiving aHCT for HL or NHL at COH constituted the sampling frame for selection of cases and controls in this nested case-control study. PBSC samples obtained pre-aHCT and BM samples at the time of development of t-MDS/AML post-HCT were studied. The training set consisted of 18 patients who developed t-MDS/AML ("cases") after aHCT, matched with 37 controls who underwent aHCT, but did not develop t-MDS/AML. Up to three controls were selected per case, matched for primary diagnosis (HL/NHL), age at aHCT (±10 years), and ethnicity (Caucasians, African-Americans, Hispanics, other). Length of follow-up after aHCT for controls was longer than the time to t-MDS/AML in the corresponding case. The results of the training set were validated in an independent group of 36 patients (test set) consisting of 16 cases that developed t-MDS/AML post-aHCT and 20 matched controls. Relevant demographic and clinical data were obtained from medical records and included age at diagnosis and aHCT, gender, race/ethnicity, disease characteristics, pre-aHCT cumulative therapeutic exposures, conditioning regimens, priming with growth factors and/or chemotherapy for PBSC mobilization and collection, number of PBSC collections, dose of CD34+ cells infused, recovery of WBC counts, vital status, and disease status after aHCT.

Gene expression analysis. In the training set, 55 PBSC samples from 18 cases and 37 matched controls were studied. BM samples from time of development of t-MDS/AML were available for 12 cases, and from 21 matched controls obtained at a comparable time from aHCT. For validation, 36 PBSC samples from a test set consisting of 16 cases and 20 matched controls were studied. All samples had been cryopreserved as mononuclear cells in LN2. Frozen cells were thawed and incubated in IMDM supplemented with 20% FBS and DNAse I (Sigma) for 3 hour incubation at 37° C. Samples were labeled with anti-CD34-APC and anti-CD45-FITC (BD biosciences) and CD34+CD45dim cells selected using flow cytometry (Beckman-Coulter, Miami, Fla.). Total RNA was extracted using the RNeasy kit (Qiagen). RNA from 1000 cells was amplified and labeled using GENECHIP® Two-Cycle Target Labeling and Control Reagents from Affymetrix (Santa Clara, Calif.). 15 μg of cRNA each was hybridized to Affymetrix HG U133 plus 2.0 Arrays.

Reactive oxygen species, anti-oxidant gene, NADH, and DNA damage analysis. To detect ROS, PBSC MNCs were incubated with carboxy-H2DCFDA (10 μM) and MITO-SOX™ Red (3 μM) (Invitrogen, Carlsbad, Calif.) at 37° C. for 30 min to detect total ROS and mitochondrial ROS respectively after exposing to etoposide (VP-16, 34 nM), mechlorethamine (NM, 2 μg/ml) or methylene blue with visible light. Cells were then labeled with CD34-PE-Cy7, CD45-APC-Cy7 (Ebioscience, San Diego, Calif.) and AnnexinV-Cy5 (BD Biosciences, San Jose, Calif.) on ice for 30 min, washed and immediately analyzed by flow cytometry using a LSRII flow cytometer (BD Biosciences, San Jose, Calif.).

For anti-oxidant gene expression measurement, 10 ng total RNA from FACS-sorted PBSC CD34+ cells was used to generate cDNA using SUPERSCRIPT® III First-Strand Synthesis System (Invitrogen, Carlsbad, Calif.). Quantitative RT-PCR for expression of heme oxygenase 1 (HMOX1), peroxiredoxin 3 (PRDX3), superoxide dismutase 2 (SOD2) was performed on an 7900HT Fast Real-Time PCR System using TAQMAN® gene expression assays (Applied Biosystems, Foster City, Calif.). Results were normalized to endogenous control β2-microglobulin (B2M) expression.

DNA damage was evaluated based on γ-H2AX level using flow cytometry. PBSC MNCs were treated with irradiation (2Gy), etoposide (VP-16, 34 nM) or mechlorethamine (nitrogen mustard, 2 μg/ml) and γ-H2AX levels were detected in CD34+ fractions 4 hours after removal of DNA damage inducers by staining with Anti-phospho-Histone H2A.X (Tyr142) (Millipore, Temecula, Calif.) following the protocol from the manufacture.

Mitochondrial NADH levels in PBSC CD34+ cells were assessed by endogenous cellular fluorescence measured at an excitation of 350 nm and an emission of 440 nm using LSRII flow cytometer. MFI (median fluorescence intensity) was normalized to control unlabeled beads (BD Biosciences, San Jose, Calif.) for each sample.

Statistical Analysis.

Microarray data were analyzed using R (version 2.9) with genomic analysis packages from Bioconductor (version 2.4). For quality control, images of the individual arrays were screened for experimental error; Affymetrix MAS 5 report was checked for background expression, scale factors and percent of present calls; and RNA degradation was examined by beta-actin 3/5 and GAPDH 3/5 ratios using Affymetrix internal controls. No obvious batch effect was observed. Data for PBSC and BM samples were normalized separately using robust multiarray averages with consideration of GC content (GCRMA), were only the probes with present call were used to estimate the background, with subsequent applications of quantile normalization and median polishing. The normalization was carried out separately for PBSC samples obtained pre-aHCT and for BM samples collected at the time of t-MDS/AML/AML or at comparable time points after aHCT for controls. Probesets with low expression or variability were filtered. The Affymetrix annotation file was used to map probesets to genes. Expression of genes represented by multiple probesets was set as the median of the probesets.

Following quality control, data for PBSC and BM samples were normalized separately. Probesets with low expression or variability were filtered. Using conditional logistic model (CLM) to retain matching between cases and controls, the magnitude of association [expressed as odds ratio (OR)] was analyzed between t-MDS/AML and i) gene expression levels in PBSC at the pre-aHCT time point; ii) gene expression levels in BM at time of t-MDS/AML; and iii) change in expression of individual genes from PBSC to development of t-MDS/AML. False discovery rate (FDR) was applied to adjust for multiple testing. Gene set enrichment analysis (GSEA) was performed on ranked lists of genes differentially expressed between cases and controls generated using CLM. The pre-ranked gene list was used to test all the 1383 gene sets (with size of [15,000]) in the C-2 category of the GSEA Molecular Signatures Database, representing curated gene sets collected from various sources including online pathway databases, biomedical literature, and the L2L database of published microarray gene expression data. The threshold of FDR was used to select significant gene sets. Where multiple significant gene sets were related to each other, analysis was performed to identify a subset of common enriched genes. Average gene expression was calculated for each set and heatmaps plotted to show the contrasts between cases and controls. Hierachical clustering was performed within each of the case and control group. Gene Ontology (GO) and pathway analysis was performed using DAVID 2008 and Ingenuity IPA 7.5 respectively, retaining genes with z-scores≥1.8 or ≤−1.8, and ≥1.5-fold change in OR between cases and controls.

The association between gene expression in the PBSC product and subsequent development of t-MDS/AML identified in the training set was validated in the test set. Pre-processing, normalization and filtering procedures for the test set were identical to the training set. Differential expression between cases and controls was analyzed using CLM. GSEA analysis was performed on the ranked list of differentially expressed genes. Prediction analysis of microarray (PAM) was used to derive a prognostic gene signature from the training set to classify patients as case or control. PAM uses the "nearest shrunken centroid" approach and 10-fold cross-validation to select a parsimonious gene expression signature that can classify samples with minimal misclassification. PAM was applied to genes common to both datasets. Based on the misclassification error in cross-validation, a 38-gene signature was selected for prediction and applied to the test set.

Accession Number.

Microarray data has been deposited in the Gene Expression Omnibus database (Accession number GSE23025).

Results

Gene expression in CD34+ cells from the training set consisting of 18 cases who developed t-MDS/AML was compared to 37 matched controls who did not develop t-MDS/AML after aHCT for HL or NHL. One to three randomly selected controls were individually matched to each case for primary diagnosis [HL/NHL], age at aHCT [±10 years], and race/ethnicity [Caucasians, African-Americans, Hispanics, other]. The median time to t-MDS/AML post-aHCT was 2.7 years (range, 0.5 to 5.2 years). The average length of follow-up after aHCT for controls (116 months; range: 75.8 to 136 months) was longer than the average time from aHCT to development of t-MDS/AML in the corresponding cases (33.4 months; range: 5.9-63.7 months). The clinical and demographic characteristics of the cases and controls are shown in FIG. 9. Comparison of cases with controls revealed no significant differences in primary diagnosis, sex, race/ethnicity, therapeutic exposures, age at primary diagnosis and aHCT, stem cell source and mobilization regimens, number of PBSC collections, CD34+ cell dose, and conditioning regimens. Detailed analysis of pre-aHCT therapeutic exposures (including cumulative doses), HCT-related conditioning, and post-aHCT therapeutic exposures (in the event of relapse), did not reveal any statistically significant difference in the intensity or nature of therapeutic exposure between cases and controls (FIG. 9). The clinical and pathological characteristics of the 18 patients with t-MDS/AML are shown in FIG. 10. PBSC samples from the 18 cases and 37 matched controls, and BM samples obtained at time of t-MDS/AML from a sub-cohort of 12 cases and 21 matched controls were studied (FIG. 12A). This subset of 12 cases did not differ significantly in clinical or demographic characteristics from the parent group. Gene expression profiles in CD34+ cells from t-MDS/AML cases and matched controls were compared using conditional logistical model (CLM) (FIG. 12A). The following comparisons were made: (1) pre-aHCT PBSC from cases versus controls; (2) BM from cases at t-MDS/AML versus BM from controls at comparable time points post-aHCT; and (3) changes in gene expression from pre-aHCT to development of t-MDS/AML in cases versus controls over a comparable time period (Δ t-MDS/AML-PBSC). The results of the training set were validated in an independent group of 36 patients (test set) consisting of 16 cases that developed t-MDS/AML post-aHCT and 20 matched controls.

Gene Expression in PBSC CD34+ Cells Preceding Onset of t-MDS/AML.

This analysis was directed towards identifying genetic changes in pre-aHCT samples, preceding onset of t-MDS/AML. Unsupervised clustering of cases and controls using all genes (filtered to remove those that were not expressed or with minimal differences across the cohort) showed that samples clustered into two major groups, with 5 cases clustering with controls and 11 controls clustering with cases (FIG. 13). PBSC from patients who developed t-MDS/AML demonstrated significant differences in gene expression compared to controls (FIG. 12B). 779 genes were upregulated and 2220 genes were downregulated in t-MDS/AML cases compared to controls, based on the criteria of absolute odds ratio>4 and P-value<0.05. Using an absolute odds ratio>4 and P-value<0.01, 44 genes were upregulated and 301 genes were downregulated in t-MDS/AML cases compared to controls.

GSEA was performed to determine concordant differences between differentially expressed genes and curated gene sets (Subramanian et al. 2005) (FIGS. 14 and 15). PBSC from patients who subsequently developed t-MDS/AML (cases) showed significant downregulation of gene sets related to mitochondria and oxidative phosphorylation (FIG. 16A), citrate cycle, ribosomes (FIG. 16B), aminoacyl-tRNA biosynthesis, amino acid metabolism, cell cycle regulation, DNA repair, and hematopoietic differentiation. G-protein coupled receptors (FIG. 16C), hematopoietic regulation, and cell adhesion related genes were upregulated in PBSC from cases. There was reduced expression of genes with binding motifs for NFE2L2 (regulator of oxidative stress and drug detoxification response) (Nguyen et al. 2009), GABP (regulator of mitochondrial enzymes) (Lenka et al. 1998), and E2F1 (regulator of cell cycle) (Chen et al. 2009), and increased expression of genes with binding motifs for GFI1 and FOXA1 (regulators of hematopoiesis) and OCT1 (regulator of DNA damage response) (Hock & Orkin 2006; Shimizu et al. 2008) (FIG. 17). In agreement with GSEA results, Ingenuity Pathway Analysis (IPA) indicated that pathways related to mitochondrial function, oxidative phosphorylation, protein ubiquitination, aminoacyl-tRNA synthesis, cell cycle regulation, citrate cycle, amino acid metabolism, and Nrf2-mediated oxidative stress response, were significantly altered in cases compared to controls (FIG. 18). Gene Ontology (GO) analysis also indicated significant reduction in mitochondrial function and oxidative phosphorylation, cell metabolism, protein synthesis, and cell cycle regulation in cases; and enrichment of genes related to GTPase activity and transcription factors, tissue/organ development and cell communication (FIG. 19). Thus, multiple analytical approaches consistently demonstrated abnormalities in gene expression related to mitochondrial function, oxidative phosphorylation, and cellular response to oxidative and genotoxic stresses in PBSC samples from patients who subsequently develop t-MDS/AML. (FIGS. 18 and 19).

Expression of enriched genes from representative gene sets in individual PBSC samples is shown in FIGS. 12C, 16D and 16E. Five of 18 PBSC samples from patients that developed t-MDS/AML demonstrated gene expression resembling that of controls. These 5 cases (#11, #62, #101, #125, and #168,) were the same as those identified on hierarchical clustering analysis using all genes. Among these 5 patients, one patient (#11) had transient myelodysplasia with del 7 which subsequently resolved; one patient (#168) developed transient del (20q); 2 patients developed persistent del(20q) or del(13q) abnormalities with mild dysplasia (#62 and #125); and one patient developed AML with 11q23 translocation (#101). (Gupta et al., 2007; Han and Theil, 2007). The remaining 13 cases that clearly showed altered gene expression in PBSC samples as compared to controls, later presented with overt t-MDS/AML. Reanalysis of data after removing the two transient cases and their controls showed enrichment of gene sets in cases and controls that were highly similar to those seen in the original analysis (FIG. 20). The major categories of gene sets upregulated in cases [GPCRs, hematopoietic transcription factors (CEBP), cell communication, xenobiotic metabolism] and downregulated in cases (upregulated in controls) [mitochondrial oxidative phosphorylation, ribosomes, aminoacyl-tRNA synthetases, proteasomal degradation, citric acid cycle, cell cycle, DNA repair and hematopoietic stem cells] were maintained in the new analysis (FIG. 21).

Gene Expression at Time of t-MDS/AML:

To evaluate genetic changes at the time of clinically overt t-MDS/AML, gene expression in BM cells at t-MDS/AML cases was compared with BM samples obtained from controls at comparable time points post-aHCT (FIG. 22A). No significant differences in distribution of subsets of CD34+ cells (HSC, CMP, GMP, and MEP) in a subset of t-MDS/AML cases (n=5 and controls (n=6) (FIG. 23), indicating that the gene expression differences identified in CD34+ cells were not simply a reflection of differences in cellular composition and were related to t-MDS/AML. GSEA analysis (FIGS. 24 and 25) showed significantly downregulated gene sets related to cell cycle regulation (FIG. 19A), DNA repair (FIG. 26B), hematopoietic differentiation, mitochondria, proteasome, citrate cycle, and amino acid metabolism in t-MDS/AML cases. Genes related to G-protein coupled receptors, cell communication (FIG. 26C), and hematopoietic regulatory factors were upregulated in cases. There was increased expression of genes with binding motifs for hematopoietic regulatory TF including GFI1, GATA1, and OCT1, and reduced expression of genes with binding motifs for E2F1 in cases (FIG. 27). IPA and GO analysis confirmed significantly downregulated DNA damage response, DNA repair and cell cycle regulation, and upregulated cell communication and adhesion in cases compared with controls (FIGS. 28 and 29). Therefore several gene sets enriched in BM CD34+ cells at time of t-MDS/AML were also enriched in PBSC CD34+ cells obtained pre-HCT, long before the onset of clinical disease. This is illustrated in FIG. 22B where gene sets significantly upregulated (n=10) or downregulated (n=185) in both PBSC and t-MDS/AML samples are highlighted. The top 50 genes (by t-score) that were differentially expressed at time of t-MDS/AML were significantly enriched in PBSC from cases (downregulated) (NES=−1.84, P-value<0.001, FDR=1.0%). These 50 genes represent a 50-gene t-MDS/AML signature that may be used in accordance with the embodiments described herein.

Expression of enriched genes from representative gene sets in individual BM samples is shown in FIG. 22C. At time of t-MDS/AML, BM from five cases showed gene expression resembling that of controls. Four of these cases presented with transient del(20q) or del(13q) abnormalities, three of whom had also shown gene expression resembling that of controls in the corresponding PBSC samples. The fifth patient presented with AML with del(7q). The remaining seven cases with clearly altered gene expression compared to controls presented with overt t-MDS/AML.

Gene expression in CD34+ cells from t-MDS/AML patients was also compared with normal BM CD34+ cells. A heat map showing up- and down-regulated genes in t-MDS/AML compared with normal CD34+ cells (FC>2 and FDR<0.05, 133 genes) is shown in FIG. 31A. Differences were observed in gene sets enriched in this analysis with those enriched when comparing t-MDS/AML samples with samples from control NHL/HL patients who did not develop t-MDS/AML (FIG. 32). In addition, gene expression in normal BM CD34+ cells was compared with control NHL/HL patients who did not develop t-MDS/AML (FIG. 31B, FIG. 32).

Considerable overlap was observed between gene sets enriched in BM CD34+ cells from t-MDS/AML and control NHL/HL patients compared to normal CD34+ cells with 87 of 219 significant gene sets (40%) common to both analysis, as shown in FIG. 33. These results suggest a significant contribution of underlying disease, therapeutic exposures and hematopoietic regeneration post-aHCT to gene expression changes observed in t-MDS/AML CD34+ cells, and support the experimental design of using controls with similar disease and therapeutic exposure as t-MDS/AML cases to identify changes in gene expression specific to t-MDS/AML. On the other hand, comparison with normal BM helps place changes in CD34+ cells from t-MDS/AML patients in the context of changes in controls that do not develop t-MDS/AML post-aHCT. For example, expression of cell cycle and oxidative phosphorylation-related genes is increased in HL/NHL controls compared to normal CD34+ cells, suggesting that the reduction in these pathways in t-MDS/AML samples compared to controls may reflect a failure to upregulate these pathways post-aHCT.

Changes in Gene Expression from Pre-aHCT to Development of t-MDS/AML:

To assess the evolution of genetic changes from pre-aHCT to clinically overt disease, changes in individual gene expression in cases from PBSC collection pre-aHCT was compared to time of t-MDS/AML post-aHCT, with controls over a similar time period (Δ t-MDS/AML-PBSC). GSEA analysis of genes showing increased or decreased expression over time was performed (FIG. 34). Significant gene sets (FDR<5%) are illustrated in FIG. 35A. Genes downregulated at time of t-MDS/AML but not in PBSC reflect changes acquired during development of t-MDS/AML. Genes related to early lymphoid progenitors were present in this group. In addition several gene sets downregulated in both pre-aHCT and t-MDS/AML samples showed significantly enhanced downregulation at time of t-MDS/AML compared to pre-aHCT samples, indicating progression of these alterations during t-MDS/AML development. These included genes related to cell cycle regulation, DNA repair, genotoxic stress response and hematopoietic maturation. Other gene sets were downregulated in PBSC but not at t-MDS/AML, or showed enhanced downregulation in PBSC compared to t-MDS/AML, likely representing alterations important early in the course of t-MDS/AML development. These included genes related to anti-oxidant response, mitochondrial oxidative phosphorylation and ribosomes.

Gene expression changes associated with development of t-MDS/AML are summarized in FIG. 35B. PBSC from patients who develop t-MDS/AML demonstrate downregulation of mitochondrial, oxidative phosphorylation, protein synthesis, cell cycle checkpoint, DNA repair, and oxidative stress response genes, and upregulation of GPCR, cell adhesion, and certain hematopoietic transcription factors. These gene alterations continue to be present at the time of development of t-MDS/AML. However progression to t-MDS/AML is associated with further downregulation of cell cycle checkpoints, DNA repair, genotoxic response and hematopoietic differentiation genes.

Outcome Prediction:

Because gene expression in PBSC samples from the training set was associated with later development of t-MDS/AML, a PBSC gene signature that could identify NHL and HL patients pre-aHCT who were at high risk for developing t-MDS/AML following aHCT was identified. PBSC samples from the training set were used to derive the gene signature which was then applied to an independent test set of 16 patients who subsequently developed t-MDS/AML after aHCT for NHL or HL, and 20 matched controls that did not develop t-MDS/AML (FIG. 36A, FIG. 11). The length of follow up for cases was 44 months (range: 4.9 to 101 months) and for controls was 76 months (range: 34 to 138 months). The clinical and demographic characteristics of t-MDS/AML patients in the training and test sets revealed differences in primary diagnosis, time to t-MDS/AML, and cytogenetic abnormalities (FIG. 37). However, patients in the two sets did not differ by age at diagnosis or HCT, number of stem cell collections, stem cell dose infused, stem cell mobilization techniques, conditioning regimens, and pre-aHCT exposure to radiation or topoisomerase II inhibitors. Independent analysis of differential gene expression between cases and controls in the test set revealed extensive overlap of up and down-regulated gene sets in t-MDS/AML cases between training and test sets (FIG. 36B, FIG. 38). Gene expression changes related to mitochondria, metabolism, cell cycle regulation and hematopoietic progenitors that were observed in the training set were validated in the test set (FIG. 14).

A cross-validated 38-gene classifier was derived from the training set using prediction analysis of microarray (PAM, FIG. 6). Expression of the 38-gene signature in both training and test sets is shown in FIGS. 36C and 36D. Hierarchical clustering of the 38 genes revealed two major clusters with significant correlation for up- and down-regulated expression of genes in cases or controls in training and test sets (P<0.001). Application of the 38-gene signature to the test set correctly classified 19 of the 20 subjects who did not subsequently develop t-MDS/AML, and 14 of the 16 subjects who did develop t-MDS/AML (FIG. 39A). Thus, there was significant correlation between predicted and true disease status [19/20 controls (95%) and 14/16 cases (87.5%), P<0.001].

The 38-gene classifier had an accuracy of 33/36=91.7% and a precision (positive predictive value) of 14/15=93.3%. The specificity of the test was 19/20=95% and the sensitivity was 14/16=87.5%. It is noteworthy that gene expression signatures derived from the training set were predictive of case versus control status in the test set despite differences in clinical characteristics between the two sets, suggesting that the gene expression signature is robust across different subsets of t-MDS/AML. The two t-MDS/AML patients who were misclassified presented with features typical of t-MDS/AML; and did not have any identifiable characteristics that distinguished them from other patients in the set. The control patient who was misclassified did not differ from other controls in terms of clinical features but developed relapse of lymphoma three years after aHCT and underwent allogeneic transplantation, and could not be followed further for development of t-MDS/AML. The misclassification of these samples may reflect a degree of heterogeneity in gene expression of CD34+ cells obtained from patients at time points prior to development of t-MDS. Repetition of the analysis after removing the two training cases with transient t-MDS/AML (#11 and #168) and their respective controls yielded a 31-gene signature which misclassified 4/16 cases in the test set as controls and 1/20 controls in the test set as cases (FIG. 39B), and did not improve the error rate compared with the original gene signature. These results indicate that the gene expression profile of hematopoietic cells pre-aHCT can identify patients at high risk for t-MDS/AML post-aHCT.

It was previously reported that same cytogenetic abnormality observed at the time of t-MDS diagnosis could be detected in pre-aHCT specimens by FISH (Abruzzese et al., 1999). Cytogenetic analysis performed on pre-aHCT bone marrow (BM) samples for all subjects in this study did not show evidence of clonal chromosomal abnormalities characteristic of t-MDS/AML (FIG. 40). FISH analysis performed on a subset of CD34+ cells from PBSC samples (n=9), which were representative of the spectrum of cytogenetic abnormalities seen, and for which sufficient samples were available, did not show evidence of the t-MDS/AML clone in PBSC CD34+ cells (FIG. 40). Therefore cells bearing clonal cytogenetic abnormalities do not contribute significantly to the altered gene expression profile in PBSC CD34+ cells from t-MDS cases. This finding strengthens the utility of gene expression analysis as described herein. The difference between these results and previous reports in the literature may reflect a practice of routinely performing cytogenetic analyses on pre-HCT BM samples from patients undergoing aHCT.

Mitochondrial Dysfunction in PBSC from Patients Who Later Developed t-MDS/AML.

Figure 41A:
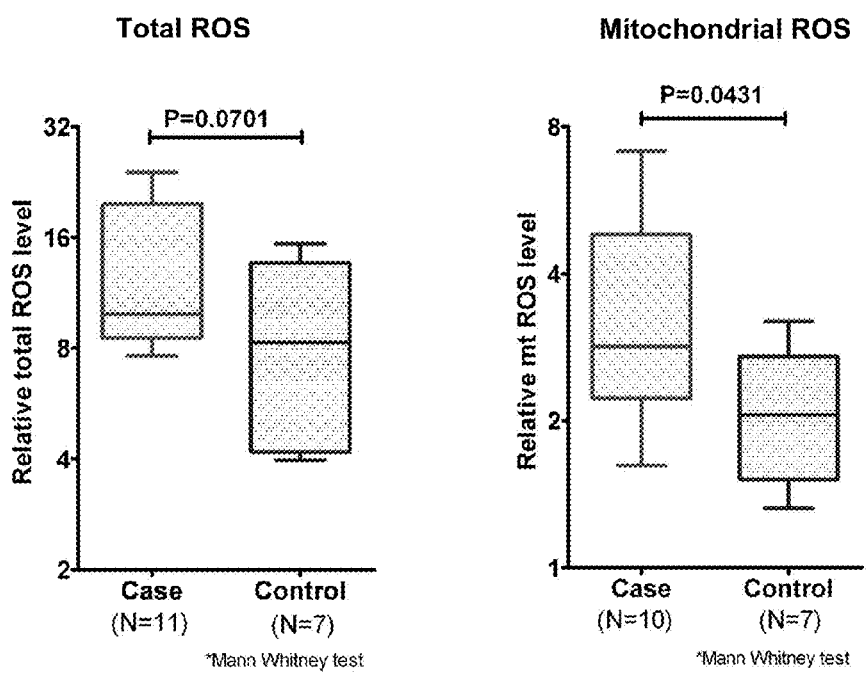
Figure 41B:
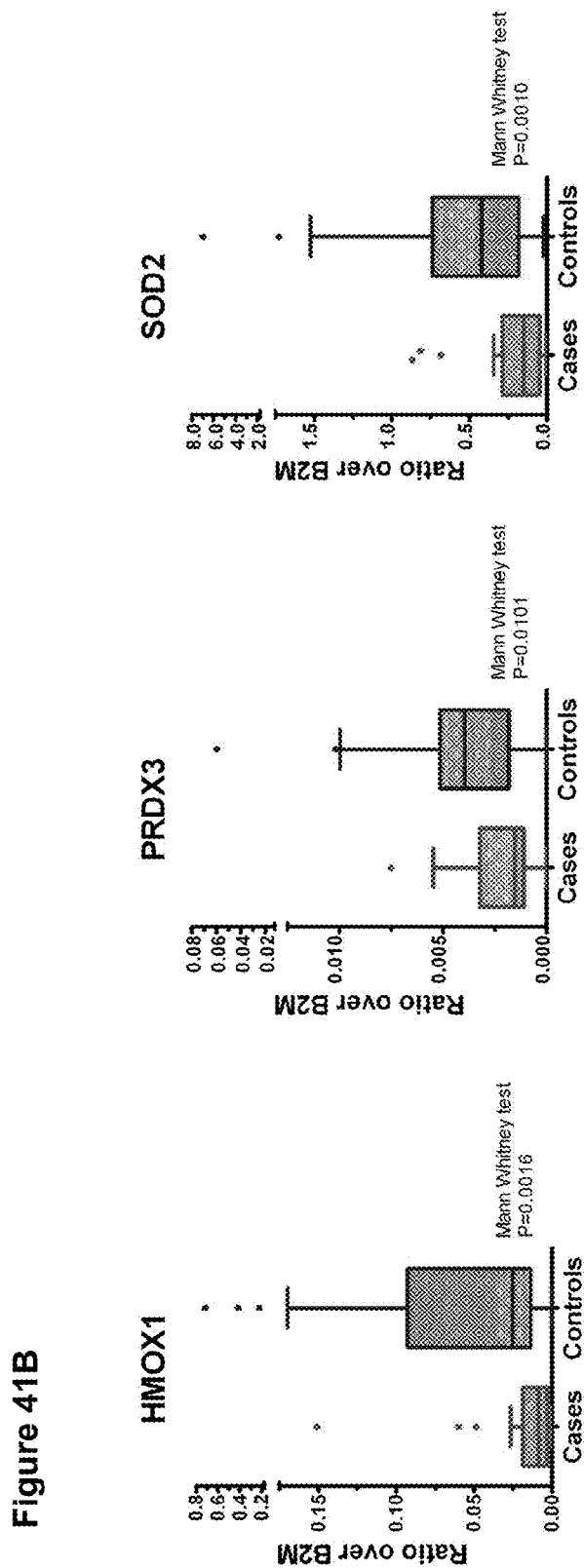

Gene signatures related to mitochondria were prominently downregulated in PBSC CD34+ cells from cases. The mitochondrial electron transport chain, in addition to its role in energy production, is a major site of reactive oxygen species (ROS) generation (Kowaltowski et al., 2009). Impaired electron transfer could result in increased ROS generation in CD34+ cells from patients who develop t-MDS/AML (Wallace, 2005). PBSC CD34+ cells from cases also demonstrated reduced expression of anti-oxidant genes, which may further increase ROS levels. Additional studies of mitochondrial function in PBSC cells from cases and controls were conducted. PBSC CD34+ cells from cases showed increased baseline levels of mitochondrial ROS (P=0.04) and total ROS (P=0.07) compared to controls (FIG. 41A). PBSC CD34+ cells from cases also demonstrated reduced expression of anti-oxidant genes, which may further increase ROS levels. Q-PCR analysis confirmed significant downregulation of the anti-oxidant genes HMOX1 (p=0.0016), PRDX3 (p=0.01), and SOD2 (p=0.001), which participate in the Nrf2-mediated oxidative stress response, in PBSC from cases compared to controls (Osburn and Kensler, 2008) (FIG. 41B).

Figure 41C:
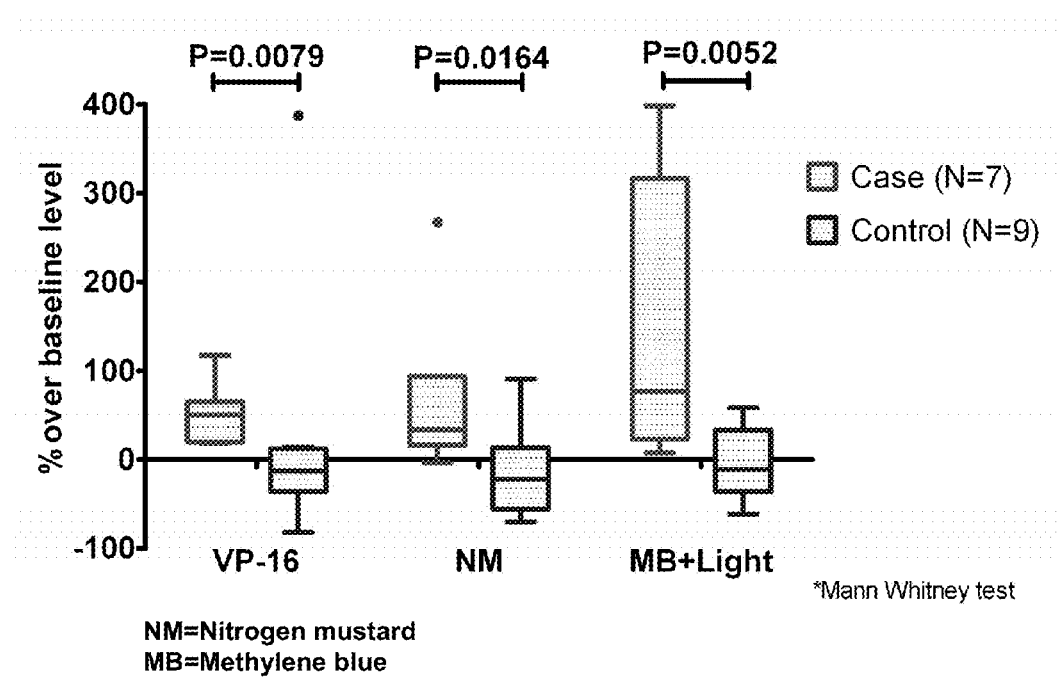
Figure 41D:
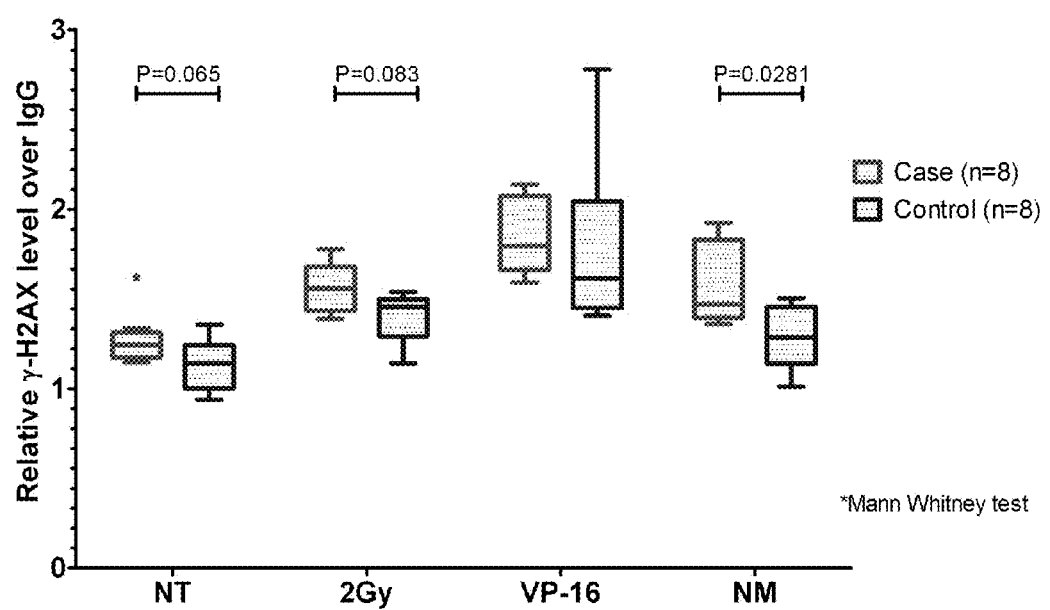
Figure 41E:
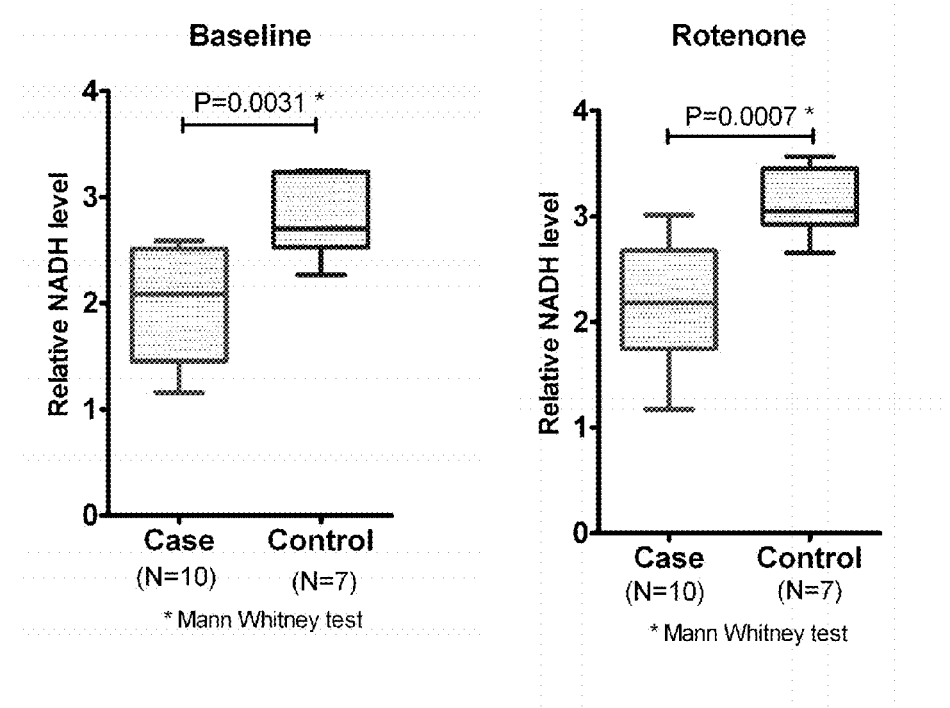
Figure 41F:
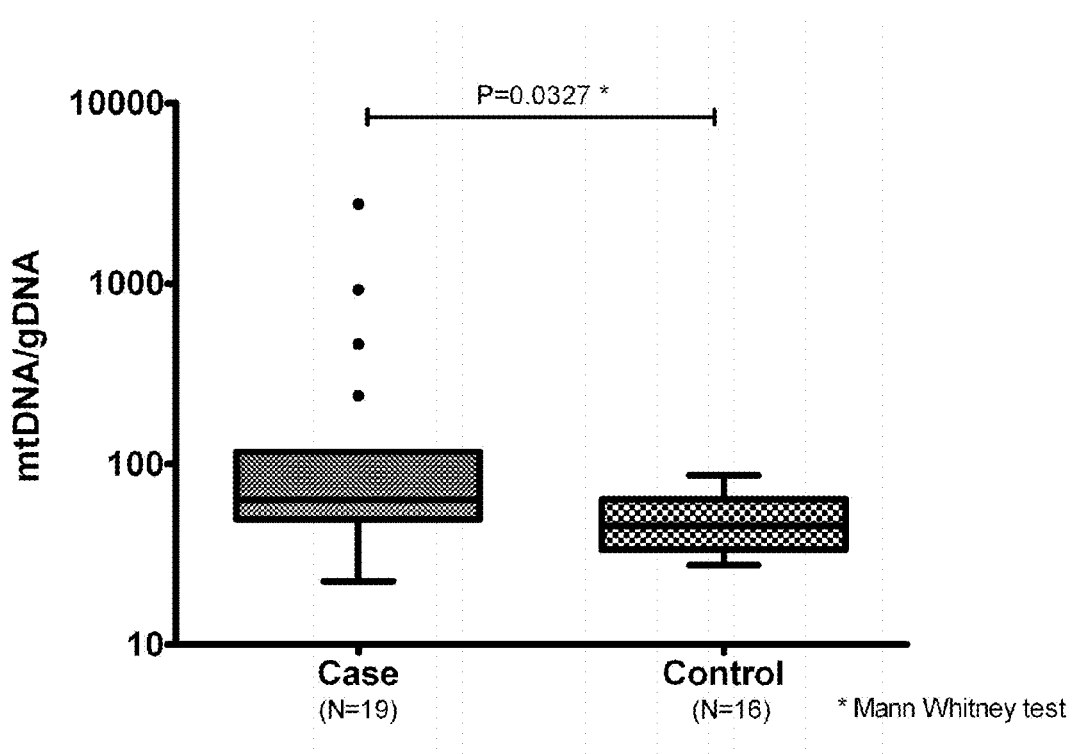

PBSC from cases exhibited sustained elevation of ROS following exposure to oxidative stressors including etoposide, nitrogen mustard and methylene blue with visible light compared to controls, consistent with reduced ROS detoxification (FIG. 41C). PBSC from cases also demonstrated significantly increased γ-H2AX levels after exposure to mechlorethamine (nitrogen mustard, p=0.0281), and a trend toward increased γ-H2AX levels after radiation and etoposide treatment (p=0.065 and 0.083 respectively), indicating increased DNA damage (Kinner et al., 2008) (FIG. 41D). PBSC from cases also demonstrated significantly reduced NADH levels compared to controls, both with and without treatment with the electron transport chain inhibitor Rotenone, suggesting impaired NADH production (Grivennikova and Vinogradov, 2006) (FIG. 41E). This observation is consistent with reduced TCA cycle activity and a broad defect in mitochondrial energy metabolism. Mitochondrial mass, estimated through measurement of mitochondrial DNA content, was increased in PBSC from cases compared to controls, possibly representing a compensatory response to mitochondrial dysfunction or reduced autophagy of damaged mitochondria (Nugent et al., 2007; Tolkovsky, 2009) (FIG. 41F). No significant differences in ROS levels were observed at the baseline (n=6) nor after exposure to oxidative stress (n=5) in CD34+ subsets (LT-HSC, CMP, GMP, MEP) selected by flow cytometry from normal PBSC samples (FIG. 42). Therefore differences in ROS levels between PBSC CD34+ cells from t-MDS/AML cases and controls cannot be explained by differences in their cellular composition. These results indicate that PBSC CD34+ cells from cases that develop t-MDS/AML have altered mitochondrial function, increased ROS generation, reduced ROS detoxification, and enhanced DNA damage after therapeutic exposure, and support the results of gene expression analysis.

REFERENCES

1. Bhatia S, Ramsay N K, Steinbuch M, et al. Malignant neoplasms following bone marrow transplantation. Blood 1996; 87:3633-9.
2. Miller J S, Arthur D C, Litz C E, Neglia J P, Miller W J, Weisdorf D J. Myelodysplastic syndrome after autologous bone marrow transplantation: an additional late complication of curative cancer therapy. Blood 1994; 83:3780-6.
3. Pedersen-Bjergaard J, Andersen M K, Christiansen D H. Therapy-related acute myeloid leukemia and myelodysplasia after high-dose chemotherapy and autologous stem cell transplantation. Blood 2000; 95:3273-9.
4. Stone R M, Neuberg D, Soiffer R, et al. Myelodysplastic syndrome as a late complication following autologous bone marrow transplantation for non-Hodgkin's lymphoma. J Clin Oncol 1994; 12:2535-42.
5. Kalaycio M, Rybicki L, Pohlman B, et al. Risk factors before autologous stem-cell transplantation for lymphoma predict for secondary myelodysplasia and acute myelogenous leukemia. J Clin Oncol 2006; 24:3604-10.
6. Krishnan A, Bhatia S, Slovak M L, et al. Predictors of therapy-related leukemia and myelodysplasia following autologous transplantation for lymphoma: an assessment of risk factors. Blood 2000; 95:1588-93.
7. Smith S M, Le Beau M M, Huo D, et al. Clinical-cytogenetic associations in 306 patients with therapy-related myelodysplasia and myeloid leukemia: the University of Chicago series. Blood 2003; 102:43-52.
8. Pedersen-Bjergaard J. Insights into leukemogenesis from therapy-related leukemia. N Engl J Med 2005; 352:1591-4.
9. Subramanian A, Tamayo P, Mootha V K, et al. Gene set enrichment analysis: a knowledge-based approach for interpreting genome-wide expression profiles. Proc Natl Acad Sci USA 2005; 102:15545-50.
10. Nguyen T, Nioi P, Pickett C B. The Nrf2-antioxidant response element signaling pathway and its activation by oxidative stress. J Biol Chem 2009; 284:13291-5.
11. Lenka N, Vijayasarathy C, Mullick J, Avadhani N G. Structural organization and transcription regulation of nuclear genes encoding the mammalian cytochrome c oxidase complex. Prog Nucleic Acid Res Mol Biol 1998; 61:309-44.
12. Chen H Z, Tsai S Y, Leone G. Emerging roles of E2Fs in cancer: an exit from cell cycle control. Nat Rev Cancer 2009; 9:785-97.
13. Hock H, Orkin S H. Zinc-finger transcription factor Gfi-1: versatile regulator of lymphocytes, neutrophils and hematopoietic stem cells. Curr Opin Hematol 2006; 13:1-6.
14. Shimizu R, Engel J D, Yamamoto M. GATA1-related leukaemias. Nat Rev Cancer 2008; 8:279-87.
15. Gupta R, Soupir C P, Johari V, Hasserjian R P. Myelodysplastic syndrome with isolated deletion of chromosome 20q: an indolent disease with minimal morphological dysplasia and frequent thrombocytopenic presentation. Br J Haematol 2007; 139:265-8.
16. Han J Y, Theil K S. Karyotypic identification of abnormal clones preceding morphological changes or occurring with no definite morphological features of myelodysplastic syndrome: a preliminary study. Lab Hematol 2007; 13:17-21.
17. Kowaltowski A J, de Souza-Pinto N C, Castilho R F, Vercesi A E. Mitochondria and reactive oxygen species. Free Radic Biol Med 2009; 47:333-43.
18. Wallace D C. Mitochondria and cancer: Warburg addressed. Cold Spring Harb Symp Quant Biol 2005; 70:363-74.
19. Ito K, Hirao A, Arai F, et al. Regulation of oxidative stress by ATM is required for self-renewal of haematopoietic stem cells. Nature 2004; 431:997-1002.
20. Bhatia R, Van Heijzen K, Palmer A, et al. Longitudinal assessment of hematopoietic abnormalities after autologous hematopoietic cell transplantation for lymphoma. J Clin Oncol 2005a; 23:6699-711.
21. Chakraborty S, Sun C L, Francisco L, et al. Accelerated telomere shortening precedes development of therapy-related myelodysplasia or acute myelogenous leukemia after autologous transplantation for lymphoma. J Clin Oncol 2009; 27:791-8.
22. Ebert B L, Pretz J, Bosco J, et al. Identification of RPS14 as a 5q-syndrome gene by RNA interference screen. Nature 2008; 451:335-9.
23. Liu J M, Ellis S R. Ribosomes and marrow failure: coincidental association or molecular paradigm? Blood 2006; 107:4583-8.
24. Fumagalli S, Di Cara A, Neb-Gulati A, et al. Absence of nucleolar disruption after impairment of 40S ribosome biogenesis reveals an rpL11-translation-dependent mechanism of p53 induction. Nat Cell Biol 2009; 11:501-8.
25. Harper J W, Elledge S J. The DNA damage response: ten years after. Mol Cell 2007; 28:739-45.
26. Kastan M B, Bartek J. Cell-cycle checkpoints and cancer. Nature 2004; 432:316-23.
27. Rassool F V, Gaymes T J, Omidvar N, et al. Reactive oxygen species, DNA damage, and error-prone repair: a model for genomic instability with progression in myeloid leukemia? Cancer Res 2007; 67:8762-71.
28. Qian Z, Fernald A A, Godley L A, Larson R A, Le Beau M M. Expression profiling of CD34+ hematopoietic stem/progenitor cells reveals distinct subtypes of therapy-related acute myeloid leukemia. Proc Natl Acad Sci USA 2002; 99:14925-30.
29. Ben-Yehuda D, Krichevsky S, Caspi O, et al. Microsatellite instability and p53 mutations in therapy-related leukemia suggest mutator phenotype. Blood 1996; 88:4296-303.
30. Feldser D M, Greider C W. Short telomeres limit tumor progression in vivo by inducing senescence. Cancer Cell 2007; 11:461-9.
31. Colburn N H, Kensler T W. Targeting transcription factors for cancer prevention—the case of Nrf2. Cancer Prev Res (Phila Pa.) 2008; 1:153-5.

What is claimed is:

1. A signature set of full length complementary DNAs (cDNAs) for predicting risk of developing therapy-related myelodysplasia or acute myeloid leukemia (t-MDS/AML) after autologous hematopoietic cell transplantation (aHCT), wherein the full length cDNAs are amplified from RNA that is expressed by genes present in a biological sample, and are associated with the development of t-MDS/AML, wherein said genes consist of REEP1, ACTL6A, GOLPH3L, CCDC99, PDIA4, GOT1, XPOT, ZYG11B, ARL61P6, NRIP3, NR4A2, FOS, EGR1, CARD6, PEX11B, EGR3, EGR4, MRPL15, SLC7A11, FOSB, GOLGA5, SMAD7, SHMT2, LRPPRC, CDCA4, RTN3, KLF2, JUN, STK17B, PSMC2, LRBA, ZNF137, GEM, PGRMC2, SLC2A3P1, NR4A3, RGS2 and SLC26A2.

* * * * *